US011214835B1

(12) United States Patent
Patel et al.

(10) Patent No.: US 11,214,835 B1
(45) Date of Patent: Jan. 4, 2022

(54) METHODS AND COMPOSITIONS FOR DIAGNOSIS AND MANAGEMENT OF NEURODEGERATIVE DISEASES

(71) Applicants: Niketa A. Patel, Land O' Lakes, FL (US); Jianfeng Cai, Tampa, FL (US)

(72) Inventors: Niketa A. Patel, Land O' Lakes, FL (US); Jianfeng Cai, Tampa, FL (US)

(73) Assignee: UNIVERSITY OF SOUTH FLORIDA, Tampa, FL (US)

( * ) Notice: Subject to any disclaimer, the term of this patent is extended or adjusted under 35 U.S.C. 154(b) by 330 days.

(21) Appl. No.: 16/001,880

(22) Filed: Jun. 6, 2018

Related U.S. Application Data

(60) Provisional application No. 62/515,737, filed on Jun. 6, 2017.

(51) Int. Cl.
| | | |
|---|---|---|
| *C07D 285/00* | (2006.01) | |
| *A61K 45/06* | (2006.01) | |
| *C12Q 1/6883* | (2018.01) | |
| *A61K 31/404* | (2006.01) | |

(52) U.S. Cl.
CPC .......... *C12Q 1/6883* (2013.01); *A61K 31/404* (2013.01); *A61K 45/06* (2013.01); *C12Q 2600/158* (2013.01); *C12Q 2600/178* (2013.01)

(58) Field of Classification Search
CPC ............ C12Q 1/6883; C12Q 2600/158; C12Q 2600/178; A61K 31/404; A61K 45/06
See application file for complete search history.

(56) References Cited

U.S. PATENT DOCUMENTS

2010/0255485 A1  10/2010 Caroni

FOREIGN PATENT DOCUMENTS

| WO | 2003025122 A3 | 3/2003 | | |
|---|---|---|---|---|
| WO | 2006002563 A3 | 1/2006 | | |
| WO | 2015081283 A3 | 6/2015 | | |
| WO | WO-2016089732 A2 * | 6/2016 | ........... | C12Q 1/6883 |
| WO | WO-2017106505 A1 * | 6/2017 | ........... | C12N 15/113 |

OTHER PUBLICATIONS

Buhler, Matthias, et al., "Adipose Tissue Selective Insulin Receptor Knockout Protects against Obesity and Obesity-Related Glucose Intolerance", Developmental Cell, 2002, pp. 25-38, vol. 3, No. 1, PubMed PMID: 12110165.
Zhu, Miaojun, et al., "lncRNA H19/miR-675 axis represses prostate cancer metastasis by targeting TGFBI", the FEBS Journal, 2014, pp. 3766-3775, vol. 281, No. 16, doi: 10.1111/febs.12902, PubMed PMID: 24988946.
Zhao, Qi, et al., "The miR-545/374a Cluster Encoded in the Ftx lncRNA is Overexpressed in HBV-Related Hepatocellular Carcinoma and Promotes Tumorigenesis and Tumor Progression", PLOS One, 2014, pp. 1-11, vol. 9, No. 10, e109782, doi: 10.1371/journal.pone.0109782, PubMed PMID: 25299640, PubMed Central PMID: PMC4192320.
Schmidt, Lars Henning, et al., "Prognostic Impact of Bcl-2 Depends on Tumor Histology and Expression of MALAT-1 lncRNA in Non-Small-Cell Lung Cancer", J Thoracic Oncology, 2014, pp. 1294-1304, vol. 9, No. 9, doi: 10.1097/JTO.0000000000000243, PubMed PMID: 25036876, ISSN: 1556-0864/14/0909-1294.
Qin, Xiaoyong, et al., "LncRNA TSLC1-AS1 is a novel tumor suppressor in glioma", International Journal of Clinical and Experimental Pathology, 2014, pp. 3065-3072, vol. 7, No. 6, www.ijcep.com, ISSN:1936-2625, IJCEP0000334, PubMed PMID: 25031725, PubMed Central PMID: PMC364604.
Coccia, Eliana M., et al., "Regulation and Expression of a Growth Arrest-Specific Gene (gas5) during Growth, Differentiation, and Development", Molecular and Cellular Biology, 1992, pp. 3514-3521, vol. 12, No. 8, PubMed PMID: 1630459, PubMed Central PMID: PMC364604.
Smith, Christine M. and Joan A. Steitz, "Classification of gas5 as a Multi-Small-Nucleolar-RNA (snoRNA) Host Gene and a Member of the 59-Terminal Oligopyrimidine Gene Family Reveals Common Features of snoRNA Host Genes", Molecular and Cellular Biology, 1998, pp. 6897-6909, vol. 18, No. 12, PubMed PMID: 9819378, PubMed Central PMID: PMC109273.
Raho. G., et al., "The gas 5 gene shows four alternative splicing patterns without coding for a protein", Gene, 2000, pp. 13-17, vol. 256, PubMed PMID: 11054530.
Smedley, Damian, et al., "Characterization of Chromosome 1 Abnormalities in Malignant Melanomas", Genes, Chromosomes, & Cancer, 2000, pp. 121-125, vol. 28, PubMed PMID: 10738310.
Qi, Lu, et al., "Association Between a Genetic Variant Related to Glutamic Acid Metabolism and Coronary Heart Disease in Individuals With Type 2 Diabetes", The Journal of the American Medical Association, 2013, pp. 821-828, vol. 310, vol. 8, doi: 10.1001/jama.2013.276305, PubMed PMID: 23982368, PubMed Central PMID: PMC3858847.
Williams, Gwyn T., et al., "A critical role for non-coding RNA GAS5 in growth arrest and rapamycin inhibition in human T-lymphocytes", Biochemical Society Transactions, 2011, pp. 482-486, vol. 39, No. 2, doi: 10.1042/BST0390482, PubMed PMID: 21428924.
Mourtada-Maarabouni, M., et al., "GAS5, a non-protein-coding RNA, controls apoptosis and is downregulated in breast cancer", Oncogene, 2009, pp. 195-208, vol. 28, No. 2, Macmillian Publishers Ltd, doi: 10.1038/onc.2008.373, PubMed PMID: 18826484.
Kino, Tomoshige, et al., "Noncoding RNA Gas5 Is a Growth Arrest- and Starvation-Associated Repressor of the Glucocorticoid Receptor", Science Signaling, 2010, pp. 1-15, vol. 3, No. 108, ra8, doi; 10.1126/scisignal.2000568, PubMed PMID: 20124551, PubMed Central PMID: PMC2819218.

(Continued)

*Primary Examiner* — Kortney L. Klinkel
*Assistant Examiner* — William Y Lee

(57) ABSTRACT

Described herein are assays, methods, and devices for diagnosing/prognosing Alzheimer's disease (AD) and/or a neurodegenerative disease in a subject. The assays, methods, and/or devices described herein can be configured to detect GAS5 long-coding RNAs and/or expression thereof in a sample from a subject.

14 Claims, 24 Drawing Sheets

Specification includes a Sequence Listing.

(56) References Cited

OTHER PUBLICATIONS

Kleiman, E., et al., "Developmentally spliced PKCbII provides a possible link between mTORC2 and Akt kinase to regulate 3T3-L1 adipocyte insulin-stimulated glucose transport", Biochemical and Biophysical Research Communications, 2009, pp. 554-559, vol. 388, No. 3, Elsevier Inc., doi: 10.1016/j.bbrc.2009.08.063, PubMed PMID: 19686698, PubMed Central PMID: PMC3033743.

Elmendorf, Jeffrey S., "Fractionation Analysis of the Subcellular Distribution of GLUT-4 in 3T3-L1 Adipocytes", Methods in Molecular Science, 2003, pp. 105-111, vol. 83, doi: 10.1385/1-59259-377-1:105, PubMed PMID: 12619721.

Tani, Hidenori, et al., "The RNA Degradation Pathway Regulates the Function of GAS5 a Non-Coding RNA in Mammalian Cells", PLOS One, 2013, pp. 1-9, vol. 8, No. 1, e55684, doi: 10.1371/journal.pone.0055684, PubMed PMID: 23383264, PubMed Central PMID: PMC3559549.

Azzalin, Claus M. and Joachim Lingner, "The Human RNA Surveillance Factor UPF1 is Required for S Phase Progression and Genome Stability", Current Biology, 2006, pp. 433-439, vol. 16, No. 4, doi: 10.1016/j.cub.2006.01.018, PubMed PMID: 16488880.

Azzalin, Claus M., "UPF1: A leader at the end of chromosomes", Nucleus, 2012, pp. 16-21, vol. 3, No. 1, doi: 10.4161/nucl.3.1.18929, PubMed PMID: 22156744.

Wu, Haifan, et al., "γ-AApeptide-based small-molecule ligands that inhibit Aβ aggregation", Chemical Communications, 2014, pp. 5206-5208, vol. 50, No. 40, doi: 10.1039/c3cc46685j, PubMed PMID: 24158240.

Teng, Peng, "Identification of novel inhibitors that disrupt STAT3-DNA interaction from a γ-AApeptide OBOC combinatorial library", Chemical Communications, 2014, pp. 8739-8742, vol. 50, No. 63, doi: 10.1039/c4cc03909b, PubMed PMID: 24964402, PubMed Central PMID: PMC4128407.

Tani, Hidenori, et al., "Identification of hundreds of novel UPF1 target transcripts by direct determination of whole transcriptome stability", RNA Biology, 2012, pp. 1370-1379, vol. 9, No. 11, doi: 10.4161/rna.22360, PubMed PMID: 23064114, PubMed Central PMID: PMC3597577.

Kitamura, Tadahiro, et al., "Insulin Receptor Knockout Mice," Annual Review of Physiology, 2003, pp. 313-332, vol. 65.

Wapinski, Orly and Howard Y. Chang, "Long noncoding RNAs and human disease," Trends in Cell Biology, 2011, pp. 354-361, vol. 21, No. 6, doi: 10.1016/j.tcb.2011.04.001.

* cited by examiner

METHODS AND COMPOSITIONS FOR DIAGNOSIS AND MANAGEMENT OF NEURODEGERATIVE DISEASES

CROSS-REFERENCE TO RELATED APPLICATIONS

This application claims the benefit of and priority to U.S. Provisional Patent Application No. 62/515,727, filed on Jun. 6, 2017, entitled "METHODS AND COMPOSITIONS FOR DIAGNOSIS AND MANAGEMENT OF NEURODEGERATIVE DISEASES," the contents of which is incorporated by reference herein in its entirety.

STATEMENT REGARDING FEDERALY SPONSORED RESEARCH OR DEVELOPMENT

This invention was made with government support under grant number 821-MR-EN-20606 awarded by the U.S. Department of Veterans Affairs. The government has certain rights in the invention.

SEQUENCE LISTING

This application contains a sequence listing filed in electronic form as an ASCII.txt file entitled 292105-1560_revised_8-17-2018_ST25.bd, created on Aug. 17, 2018. The content of the sequence listing is incorporated herein in its entirety.

BACKGROUND

Alzheimers Disease (AD) is a neurodegenerative disease that is associated with age and leads to behavior and personality changes, a decline in cognitive abilities and ultimately a severe loss of mental function. These symptoms are correlated to the gradual breakdown of the connections between certain neurons in the brain and their eventual death. AD patients die from complications associated with the loss of neurons.

There is no current medication that can slow the progression of AD. However, there aree four Food and Drug Association approved medications that are used to treat AD symptoms. These drugs are associated with many adverse side effects. As such there exists a need for improved diagnostic, prognostic, preventative, and therapeutic options of prevention and treatment of AD as well as other neurodegenerative diseases and symptoms thereof.

BRIEF DESCRIPTION OF THE DRAWINGS

Further aspects of the present disclosure will be readily appreciated upon review of the detailed description of its various embodiments, described below, when taken in conjunction with the accompanying drawings.

FIG. 10A shows the results of a qPCR analysis of immunoprecipitated DNA. FIG. 10B shows GAS5 levels in the RNA pol II immunoprecipitate as analysed by qPCR. Each experiment was repeated 3 times.

DETAILED DESCRIPTION

Figure 1:
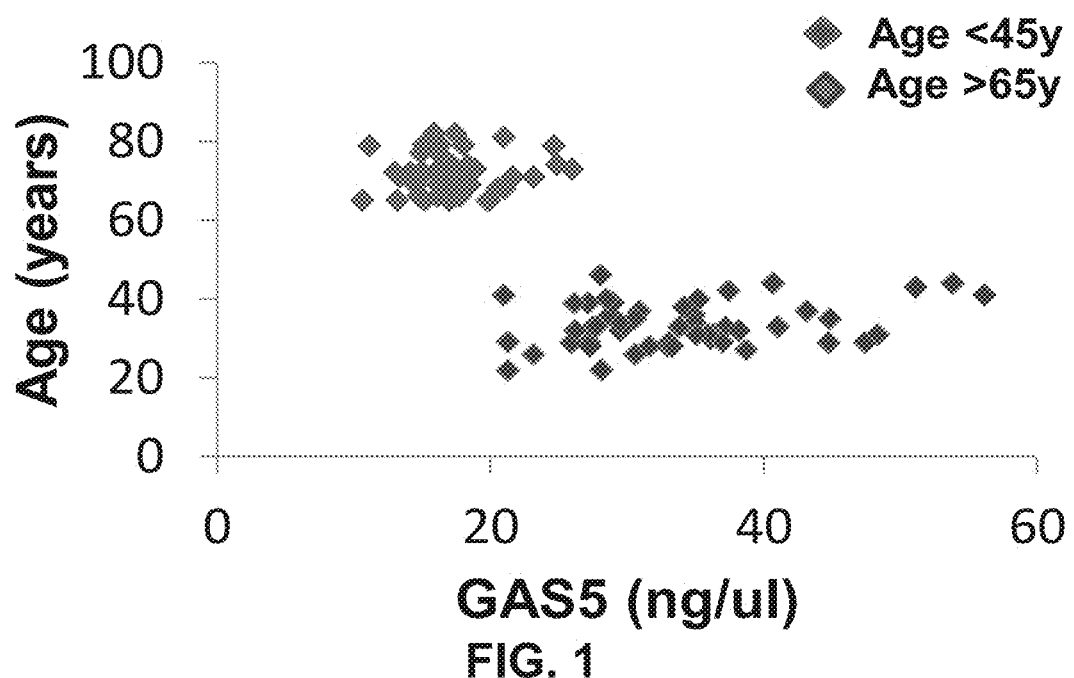
FIG. 1 shows a graph demonstrating the results from a SYBR Green absolute qPCR analysis of GAS5.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are cited to disclose and describe the methods and/or materials in connection with which the publications are cited. All such publications and patents are herein incorporated by references as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant application should not be treated as such and should not be read as defining any terms appearing in the accompanying claims. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

Where a range is expressed, a further aspect includes from the one particular value and/or to the other particular value. Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure. For example, where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

Embodiments of the present disclosure will employ, unless otherwise indicated, techniques of molecular biology, microbiology, nanotechnology, organic chemistry, biochemistry, botany and the like, which are within the skill of the art. Such techniques are explained fully in the literature.

Definitions

The definitions provided here refer to the terms as they are used herein unless otherwise defined herein.

As used herein, "isolated" means separated from constituents, cellular and otherwise, with which the polynucleotide, peptide, polypeptide, protein, antibody, or fragments thereof, are normally associated in nature. A non-naturally occurring polynucleotide, peptide, polypeptide, protein, antibody, or fragments thereof, does not require "isolation" to distinguish it from its naturally occurring counterpart.

As used herein, "specific binding," "specifically bound," and the like, refer to binding that occurs between such paired species as nucleotide/nucleotide, polynucleotide/polynucleotide, enzyme/substrate, receptor/agonist, antibody/antigen, and lectin/carbohydrate that can be mediated by covalent or non-covalent interactions or a combination of covalent and non-covalent interactions. When the interaction of the two species produces a non-covalently bound complex, the binding which occurs is typically electrostatic, hydrogen-bonding, or the result of lipophilic interactions. Accordingly, "specific binding" occurs between a paired species where there is interaction between the two which produces a bound complex having the characteristics of an antibody/antigen or enzyme/substrate interaction. "Specific binding" can be characterized by the binding of one member of a pair to a particular species and to no other species within the family of compounds to which the corresponding member of the binding member belongs. "Specific binding" can also occur when enough binding of one member of a pair to a particular species occurs such that the binding of the member and the particular species can be deemed statistically significant as compared to the amount of binding that occurs between the one member and non-specific binding species. In other words, "specific binding" also refers to the binding between one member of a pair to a particular species that occurs at such a rate or an amount so that the signal to noise ratio allows detection of this binding interaction amongst all other binding interactions that occur with the one member of the pair. Thus, for example, an antibody preferably binds to a single epitope and to no other epitope within the family of proteins or a polynucleotide preferably binding its perfect complementary polynucleotide as opposed to binding a partial complementary polynucleotide.

As used herein, "differentially expressed," refers to the differential production of RNA, including but not limited to mRNA, tRNA, miRNA, siRNA, snRNA, lncRNA, and piRNA transcribed from a gene or non-coding region of a genome or the protein product encoded by a gene as compared to the level of production of RNA or protein by the same gene or regulator region in a normal or a control cell. In another context, "differentially expressed," also refers to nucleotide sequences or proteins in a cell or tissue which have different temporal and/or spatial expression profiles as compared to a normal or control cell.

As used herein, "expression" refers to the process by which polynucleotides are transcribed into RNA transcripts. In the context of mRNA and other translated RNA species, "expression" also refers to the process or processes by which the transcribed RNA is subsequently translated into peptides, polypeptides, or proteins.

As used herein, "peptide" refers to two or more amino acids where the alpha carboxyl group of one amino acid is bound to the alpha amino group of another amino acid. Strings of 10 or more amino acids are also referred to herein as "polypeptides" or "proteins".

As used herein, "polypeptides" or "proteins" are amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

As used herein, "gene" refers to a hereditary unit corresponding to a sequence of DNA that occupies a specific location on a chromosome and that contains the genetic instruction for a characteristic(s) or trait(s) in an organism. "Gene" also refers to the specific sequence of DNA that is transcribed into an RNA transcript that can be translated into a polypeptide or be a catalytic or non-translated RNA molecule including but not limited to tRNA, siRNA, piRNA, miRNA, lncRNA, and shRNA.

As used herein, "deoxyribonucleic acid (DNA)" and "ribonucleic acid (RNA)" generally refer to any polyribonucleotide or polydeoxribonucleotide, which can be unmodified RNA or DNA or modified RNA or DNA. RNA can be in the form of a tRNA (transfer RNA), snRNA (small nuclear RNA), rRNA (ribosomal RNA), mRNA (messenger RNA), anti-sense RNA, RNAi (RNA interference construct), siRNA (short interfering RNA), microRNA (miRNA), long non-coding RNA (lncRNA), or ribozymes.

As used herein, "nucleic acid sequence" and "oligonucleotide" also encompasses a nucleic acid and polynucleotide as defined above.

As used herein, "DNA molecule" includes nucleic acids/polynucleotides that are made of
DNA.

As used herein, "nucleic acid" and "polynucleotide" generally refer to a string of at least two base-sugar-phosphate combinations and refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that can be single-stranded or, more typically, double-stranded or a mixture of single- and double-stranded regions. In addition, polynucleotide as used herein refers to triple-stranded regions comprising RNA or DNA or both RNA and DNA. The strands in such regions can be from the same molecule or from different molecules. The regions can include all of one or more of the molecules, but more typically involve only a region of some of the molecules. One of the molecules of a triple-helical region often is an oligonucleotide. "Polynucleotide" and "nucleic acids" also encompasses such chemically, enzymatically or metabolically modified forms of polynucleotides, as well as the chemical forms of DNA and RNA characteristic of viruses and cells, including simple and complex cells, inter alia. For instance, the term polynucleotide includes DNAs or RNAs as described above that contain one or more modified bases. Thus, DNAs or RNAs comprising unusual bases, such as inosine, or modified bases, such as tritylated bases, to name just two examples, are polynucleotides as the term is used herein. "Polynucleotide" and "nucleic acids" also includes PNAs (peptide nucleic acids), phosphorothioates, and other variants of the phosphate backbone of native nucleic acids. Natural nucleic acids have a phosphate backbone, artificial nucleic acids can contain other types of backbones, but contain the same bases. Thus, DNAs or RNAs with backbones modified for stability or for other reasons are "nucleic acids" or "polynucleotide" as that term is intended herein.

As used herein, "microRNA" refers to a small non-coding RNA molecule containing about 21 to about 23 nucleotides found in organisms, which functions in transcriptional and post-transcriptional regulation of transcription and translation of RNA.

As used herein, "long non-coding RNA" refers to a non-coding RNA molecule containing about 200 or more nucleotides that are not translated to a protein.

As used herein, "purified" is used in reference to a nucleic acid sequence, peptide, or polypeptide or other compound described herein that has increased purity relative to the natural environment.

As used herein, "about," "approximately," and the like, when used in connection with a numerical variable, generally refers to the value of the variable and to all values of the variable that are within the experimental error (e.g., within the 95% confidence interval for the mean) or within ±10% of the indicated value, whichever is greater.

As used herein, "control" is an alternative subject or sample used in an experiment for comparison purposes and included to minimize or distinguish the effect of variables other than an independent variable. A "control" can be a positive control, a negative control, or an assay or reaction control (an internal control to an assay or reaction included to confirm that the assay was functional). In some instances, the positive or negative control can also be the assay or reaction control.

As used herein, "concentrated" used in reference to an amount of a molecule, compound, or composition, including, but not limited to, a chemical compound, polynucleotide, peptide, polypeptide, protein, antibody, or fragments thereof, that indicates that the sample is distinguishable from its naturally occurring counterpart in that the concentration or number of molecules per volume is greater than that of its naturally occurring counterpart.

As used herein, "diluted" used in reference to an amount of a molecule, compound, or composition including but not limited to, a chemical compound, polynucleotide, peptide, polypeptide, protein, antibody, or fragments thereof, that indicates that the sample is distinguishable from its naturally occurring counterpart in that the concentration or number of molecules per volume is less than that of its naturally occurring counterpart.

As used interchangeably herein, "subject," "individual," or "patient," refers to a vertebrate, preferably a mammal, more preferably a human. Mammals include, but are not limited to, murines, simians, humans, farm animals, sport animals, and pets. The term "pet" includes a dog, cat, guinea pig, mouse, rat, rabbit, ferret, and the like. The term farm animal includes a horse, sheep, goat, chicken, pig, cow, donkey, llama, alpaca, turkey, and the like.

As used herein, "biocompatible" or "biocompatibility" refers to the ability of a material to be used by a patient without eliciting an adverse or otherwise inappropriate host response in the patient to the material or an active derivative thereof, such as a metabolite, as compared to the host response in a normal or control patient.

The term "treating", as used herein, can include inhibiting the disease, disorder or condition, e.g., impeding its progress; and relieving the disease, disorder, or condition, e.g., causing regression of the disease, disorder and/or condition. Treating the disease, disorder, or condition can include ameliorating at least one symptom of the particular disease, disorder, or condition, even if the underlying pathophysiology is not affected, such as treating the pain of a subject by administration of an analgesic agent even though such agent does not treat the cause of the pain.

The term "preventing", as used herein includes preventing a disease, disorder or condition from occurring in an animal, which can be predisposed to the disease, disorder and/or condition but has not yet been diagnosed as having it.

As used herein, "mitigate" refers to reducing a particular characteristic, symptom, or other biological or physiological parameter associated with a disease or disorder.

As used herein, "separated" refers to the state of being physically divided from the original source or population such that the separated compound, agent, particle, chemical compound, or molecule can no longer be considered part of the original source or population.

As used herein, "capture molecule" refers to a molecule that is configured to specifically bind one or more biomarker molecules of interest. A capture molecule can be a polynucleotide, antibody, antigen, apatmer, affibody, polypeptides, peptides, or combinations thereof that can specifically bind one or more biomarkers of interest. For example, the capture molecule can be configured to specifically bind a polynucleotide corresponding to gas5 (e.g. a lncRNA having a sequence 95-100% identical to SEQ ID NO: 1). Representative polynucleotide sequences for the aforementioned biomarkers and any other biomarkers described herein are demonstrated herein.

As used herein "essentially discrete" as applied to features of an array refers to the situation where 90% or more of the features of an array are not in direct contact with other features of the same array.

As used herein "attached" as applied to capture molecules of an array refers to a covalent interaction or bond between a molecule on the surface of the support and the capture molecule so as to immobilize the capture molecule on the surface of the support.

As used herein "operatively-linked" as applied to capture molecules of an array refers to a non-covalent interaction between the surface of the support and the capture molecule so as to immobilize the capture molecule on the surface of the support. Such non-covalent interactions include by are not limited to, entrapment by the surface substrate, ionic bonds, electrostatic interactions, van der Walls forces, dipole-dipole interactions, dipole-induced-dipole interactions, London dispersion forces, hydrogen bonding, halogen bonding, electromagnetic interactions, $\pi$-$\pi$ interactions, cation-$\pi$ interactions, anion-$\pi$ interactions, polar $\pi$-interactions, and hydrophobic effects.

As used herein, "biomarker" refers to any measurable molecule, including but not limited to polynucleotides and polypeptides, or compound in a subject whose presence, absolute amount, or relative amount, is indicative of some disease, condition, syndrome, disorder, symptom thereof, or state thereof.

As used herein, "body fluid" refers to any liquid or liquid-like substance that originates in the body of a living organism. "Body fluid" includes, but is not limited to, whole blood, serum, buffy coat of blood or other blood fraction that contains substantially only the white blood cells and platelets, plasma, cerebral spinal fluid, urine, lymph, bile, acites fluid, and saliva.

As used herein, "variant" refers to a polypeptide that differs from a reference polypeptide, but retains essential properties. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide can differ in amino acid sequence by one or more modifications (e.g., substitutions, additions, and/or deletions). A substituted or inserted amino acid residue can or cannot be one encoded by the genetic code. A variant of a polypeptide can be naturally occurring such as an allelic variant, or it can be a variant that is not known to occur naturally.

As used herein, "wild-type" refers to the typical form of an organism, variety, strain, gene, protein, or characteristic as it occurs in nature, as distinguished from mutant forms that can result from selective breeding or transformation with a transgene.

As used herein, "diagnosis" refers to the identification or determination of the nature and circumstances of a disease, disorder, condition, syndrome, or symptom thereof in a subject.

As used herein, "prognose," refers to determining a prognosis for a disease, disorder, condition, syndrome, or symptom thereof.

As used herein, "prognosis" refers to a prediction or forecast of a chance of recovery, complete or partial, from a disease, disorder, condition, syndrome, or symptom thereof.

As used herein, "pre-disposed" refers to an individual having at least one factor known to contribute towards the development of a disease that puts the individual at a greater risk of developing the disease compared a normal (non-predisposed) individual or greater than the average risk of a contemporary population.

As used herein with reference to the relationship between DNA, cDNA, cRNA, RNA, and protein/peptides, "corresponding to" and similar terms refer to the underlying biological relationship between these different molecules. As such, one of skill in the art would understand that operatively "corresponding to" can direct them to determine the possible underlying and/or resulting sequences of other molecules given the sequence of any other molecule which has a similar biological relationship with these molecules. For example, from a DNA sequence an RNA sequence can be determined and from an RNA sequence a cDNA sequence can be determined.

As used herein, "additive effect" can refer to an effect arising between two or more molecules, compounds, substances, factors, or compositions that is equal to or the same as the sum of their individual effects.

As used herein, "derivative" can refer to any compound having the same or a similar core structure to the compound but having at least one structural difference, including As used herein, "active derivative" and the like can refer to a modified compound containing a GAS5 binding compound as provided herein. The term "active derivative" and the like can also refer to an analogue provided herein that retains an ability to bind GAS5 lncRNA. Assays for testing the ability of an active derivative to perform in this fashion are known to those of ordinary skill in the art and provided herein. The assays can include, but are not limited to, quantitative real-time PCR, RNA electrophoretic mobility assay, RNA Fluorescence hybridization, western blot analysis, hybrid systems in yeast and mammalian, RNA-immunoprecipitations.

As used herein, "administering" can refer to any administration route, including but not limited to administration that is oral, topical, intravenous, subcutaneous, transcutaneous, transdermal, intramuscular, intra-articular, parenteral, intra-arterial, intradermal, intraventricular, intracranial, intraperitoneal, intralesional, intranasal, rectal, vaginal, by inhalation, or via an implanted reservoir. The term "parenteral" includes subcutaneous, intravenous, intramuscular, intra-articular, intra-synovial, intrasternal, internasal, intrathecal, intrahepatic, intralesional, and intracranial injections or infusion techniques.

As used interchangeably herein, "biocompatible," "biocompatibility," and "biologically compatible" can refer to materials that are, with any metabolites or degradation products thereof, generally non-toxic to the recipient, and cause no significant adverse effects to the recipient. Generally speaking, biocompatible materials are materials which do not elicit a significant inflammatory or immune response when administered to a patient. In some embodiments, a biocompatible material elicits no detectable change in one or more biomarkers indicative of an immune response. In some embodiments, a biocompatible material elicits no greater than a 10% change, no greater than a 20% change, or no greater than a 40% change in one or more biomarkers indicative of an immune response.

As used herein, "chemotherapeutic" can refer to a chemical compound or agent used to treat, control, or cure a disease or symptoms thereof, particularly cancer.

As used herein, "composition" or "formulation" can refer to a combination of an active agent(s) and another compound or composition, inert (for example, a detectable agent or label) or active, such as an adjuvant.

As used herein, "a compound of formula (1), (2), (3), (4), (6), (7), (8), (9), (10), (11), (12), (13), (14), and so forth and so on," or "a compound having a structure according to formula (1), (2), (3), (4), (6), (7), (8), (9), (10), (11), (12), (13), (14), etc." can include all or any sub-group of solvates, complexes, polymorphs, derivatives thereof (including but not limited to, radiolabeled derivatives (including deuterated derivatives where one or more H are replaced by D)), tautomers, stereoisomers, and optical isomers of the compound of the formulas listed above and salts thereof.

As used herein, "control" can refer to an alternative subject or sample used in an experiment for comparison purposes and included to minimize or distinguish the effect of variables other than an independent variable. A control can be positive or negative.

As used herein, "concentrated" can refer to an amount of a molecule, compound, or composition, including, but not limited to, a chemical compound, polynucleotide, peptide, polypeptide, protein, antibody, or fragments thereof, that indicates that the sample is distinguishable from its naturally occurring counterpart in that the concentration or number of molecules per volume is greater than that of its naturally occurring counterpart.

As used herein, "derivative" can refer to substituting, deleting, and/or adding one or more atoms or functional groups. The term "derivative" does not mean that the derivative is synthesized from the parent compound either as a starting material or intermediate, although this may be the case. The term "derivative" can include salts, prodrugs, or metabolites of the parent compound. Derivatives include compounds in which free amino groups in the parent compound have been derivatized to form amine hydrochlorides, p-toluene sulfonamides, benzoxycarboamides, t-butyloxycarboamides, thiourethane-type derivatives, trifluoroacetylamides, chloroacetylamides, or formamides. Derivatives include compounds in which carboxyl groups in the parent compound have been derivatized to form salts, methyl and ethyl esters, or other types of esters or hydrazides. Derivatives include compounds in which hydroxyl groups in the parent compound have been derivatized to form O-acyl or O-alkyl derivatives. Derivatives include compounds in which a hydrogen bond donating group in the parent compound is replaced with another hydrogen bond donating group such as OH, NH, or SH. Derivatives include replacing a hydrogen bond acceptor group in the parent compound with another hydrogen bond acceptor group such as esters, ethers, ketones, carbonates, tertiary amines, imines, thiones, sulfones, tertiary amides, and sulfides. "Derivatives" also includes extensions of the replacement of the cyclopentane ring with saturated or unsaturated cyclohexane or other more complex, e.g., nitrogen-containing rings, and extensions of these rings with various side groups.

As used herein, "diluted" can refer to an amount of a molecule, compound, or composition including but not limited to, a chemical compound, polynucleotide, peptide, polypeptide, protein, antibody, or fragments thereof, that indicates that the sample is distinguishable from its naturally occurring counterpart in that the concentration or number of molecules per volume is less than that of its naturally occurring counterpart.

As used herein, "effective amount" can refer to an amount sufficient to effect beneficial or desired results. An effective amount can be administered in one or more administrations, applications, or dosages. "Effective amount" can refer to an amount of a compound, derivative, and/or formulation thereof provided herein that can treat or prevent neurodegenerative diseases including, but not limited to, AD. The "effective amount" can also refer to the least amount sufficient to effect beneficial or desired results as described herein.

As used herein, "hydrate" can refer to a compound formed by the addition of water. Typically, but not always, this will be crystalline lattice structures that incorporate water molecules. Hydrates include stoichiometric hydrates, as well as compositions containing variable amounts of water.

As used herein, "mitigate" can refer to reducing a particular characteristic, symptom, or other biological or physiological parameter associated with a disease or disorder.

As used herein, "pharmaceutical formulation" can refer to the combination of an active agent, compound, or ingredient with a pharmaceutically acceptable carrier or excipient, making the composition suitable for diagnostic, therapeutic, or preventive use in vitro, in vivo, or ex vivo.

As used herein "pharmaceutically effective amount", "effective amount" and the like can refer to an amount of a compound or formulation thereof provided herein that can treat or prevent neurodegenerative diseases including, but not limited to, AD. In embodiments, the "pharmaceutically effective amount" can be the least amount of a compound or formulation thereof provided herein needed to treat, prevent, or elicit the desired biological and/or medical effect in the response of a cell, tissue, organ, system, or subject that is being sought by the researcher, veterinarian, medical doctor or other clinician. In some embodiments, the "pharmaceutically effective amount" can be the least amount that can treat or prevent, neurodegenerative diseases including, but not limited to, AD. "Pharmaceutically effective amount" or "pharmaceutically effective dose," can refer to the amount of a compound or formulation thereof provided herein that will elicit the biological and/or medical response of a cell, tissue, organ, system, or subject that is being sought by the researcher, veterinarian, medical doctor or other clinician. The pharmaceutically effective amount can vary depending on the compound, formulation the disorder or condition (normal or abnormal) and its severity, the route of administration, time of administration, rate of excretion, drug or compound, judgment of the researcher, veterinarian, medical doctor or other clinician, dosage form, and the age, weight, general health, sex and/or diet of the subject to be treated.

As used herein, "pharmaceutically acceptable" can refer to compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio, in accordance with the guidelines of agencies such as the Food and Drug Administration.

As used herein, "pharmaceutically acceptable carrier or excipient" can refer to a carrier or excipient that is useful in preparing a pharmaceutical composition that is generally safe, non-toxic and neither biologically nor otherwise undesirable, and includes a carrier or excipient that is acceptable for veterinary use as well as human pharmaceutical use. A "pharmaceutically acceptable carrier or excipient" as used herein also includes both one and more than one such carrier or excipient. Pharmaceutically acceptable carriers include, but are not limited to, diluents, preservatives, binders, lubricants, disintegrators, swelling agents, fillers, stabilizers, and combinations thereof.

As used herein, "pharmaceutically acceptable salt" can refer to any salt derived from organic and inorganic acids of a compound described herein. Pharmaceutically acceptable salt also refers to a salt of a compound described having an acidic functional group, such as a carboxylic acid functional group, and a base. Pharmaceutically acceptable salt also includes hydrates of a salt of a compound described herein.

As used herein, "preventative," "preventing," "prevent" and the like can refer to partially or completely delaying and/or precluding the onset or recurrence of a disorder or conditions and/or one or more of its attendant symptoms or barring a subject from acquiring or reacquiring a disorder or condition or reducing a subject's risk of acquiring or reacquiring a disorder or condition or one or more of its attendant symptoms including, but not limited to, neurodegenerative diseases including, but not limited to AD.

As used herein, "separated" can refer to the state of being physically divided from the original source or population such that the separated compound, agent, particle, chemical compound, or molecule can no longer be considered part of the original source or population.

As used herein, "solvate" refers to a complex of variable stoichiometry formed by a solute (e.g. formulas (1)-(14) or a salt thereof) and a solvent. Pharmaceutically acceptable solvates may be formed for crystalline compounds wherein solvent molecules are incorporated into the crystalline lattice during crystallization. The incorporated solvent molecules can be water molecules or non-aqueous molecules, such as but not limited to, ethanol, isopropanol, dimethyl sulfoxide, acetic acid, ethanolamine, and ethyl acetate molecules.

As used interchangeably herein, "subject," "individual," or "patient," can refer to a vertebrate, preferably a mammal, more preferably a human. Mammals include, but are not limited to, murines, simians, humans, farm animals, sport animals, and pets. The term "pet" includes a dog, cat, guinea pig, mouse, rat, rabbit, ferret, and the like. The term farm animal includes a horse, sheep, goat, chicken, pig, cow, donkey, llama, alpaca, turkey, and the like.

The terms "sufficient" and "effective," as used interchangeably herein, can refer to an amount (e.g. mass, volume, dosage, concentration, and/or time period) needed to achieve one or more desired result(s). For example, a therapeutically effective amount refers to an amount needed to achieve one or more therapeutic effects.

As used herein, "synergistic effect," "synergism," or "synergy" can refer to an effect arising between two or more molecules, compounds, substances, factors, or compositions that that is greater than or different from the sum of their individual effects.

As used herein, "tangible medium of expression" can refer to a medium that is physically tangible and is not a mere abstract thought or an unrecorded spoken word. Tangible medium of expression includes, but is not limited to, words on a cellulosic or plastic material or data stored on a suitable device such as a flash memory or CD-ROM.

As used herein, "therapeutic", "treating", "treat," and the like can refer to include partially or completely delaying, alleviating, mitigating or reducing the intensity of one or more attendant symptoms of a disease or condition including, but not limited to, neurodegenerative diseases including, but not limited to AD.

As used herein, "alkyl" and "alkylene" refer to a saturated hydrocarbon chain having the specified number of member atoms.

The term "alkyl" can also refer to the radical of saturated aliphatic groups (i.e., an alkane with one hydrogen atom removed), including straight-chain alkyl groups, branched-chain alkyl groups, cycloalkyl (alicyclic) groups, alkyl-substituted cycloalkyl groups, and cycloalkyl-substituted alkyl groups. "Alkyl" also refers to a saturated hydrocarbon chain having the specified number of atoms.

The term "alkyl" (or "lower alkyl") as used herein can include both "unsubstituted alkyls" and "substituted alkyls," the latter of which refers to alkyl moieties having one or more substituents replacing a hydrogen on one or more carbons of the hydrocarbon backbone. Such substituents include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, phosphinate, amino, amido, amidine, imine, cyano, nitro, azido, sulfhydryl, alkylthio, sulfate, sulfonate, sulfamoyl, sulfonamido, sulfonyl, heterocyclyl, aralkyl, or an aromatic or heteroaromatic moiety.

Unless the number of carbons is otherwise specified, "lower alkyl" as used herein can refer to an alkyl group, as defined above, but having from one to ten carbons in its backbone structure. Likewise, "lower alkenyl" and "lower alkynyl" have similar chain lengths.

It will be understood by those skilled in the art that the moieties substituted on the hydrocarbon chain can themselves be substituted, if appropriate. For instance, the substituents of a substituted alkyl may include halogen, hydroxy, nitro, thiols, amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Cycloalkyls can be substituted in the same manner.

As used herein, "$C_{1-6}$alkyl" can refer to an alkyl group having any number of member atoms from 1 to 6 member atoms, such as for example 1 to 4 atoms. Other alkyl groups may have any number of member atoms as indicated by the numbers given in the formula, which, like the previous example, can refer to an alkyl group having any number of member atoms within the specified range of member atoms. Alkyl groups may be straight or branched. Representative branched alkyl groups have one, two, or three branches. Alkyl includes methyl, ethyl, propyl (n-propyl and isopropyl), butyl (n-butyl, isobutyl, and t-butyl), pentyl (n-pentyl, isopentyl, and neopentyl), and hexyl.

As used herein, "heterocyclic group" can refer to a non-aromatic ring and having the specified number of member atoms being saturated or having one or more degrees of unsaturation and, unless otherwise specified, containing one or more heteroatoms.

As used herein, "heteroaryl" can refer to an aromatic ring having the specified number of member atoms and, unless otherwise specified, containing one or more heteroatoms. Bicyclic and other polycyclic ring systems having a heteroaryl ring are described as fused systems.

The term "heteroalkyl," as used herein, can refer to straight or branched chain, or cyclic carbon-containing radicals, or combinations thereof, containing at least one heteroatom. Suitable heteroatoms include, but are not limited to, O, N, Si, P, Se, B, and S, wherein the phosphorous and sulfur atoms are optionally oxidized, and the nitrogen heteroatom is optionally quaternized. Heteroalkyls can be substituted as defined above for alkyl groups.

The term "heteroalkyl," as used herein, can refer to straight or branched chain, or cyclic carbon-containing radicals, or combinations thereof, containing at least one heteroatom. Suitable heteroatoms include, but are not limited to, 0, N, Si, P, Se, B, and S, wherein the phosphorous and sulfur atoms are optionally oxidized, and the nitrogen heteroatom is optionally quaternized. Heteroalkyls can be substituted as defined above for alkyl groups.

As used herein, "alkoxyl" or "alkoxy," as used herein, can refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl is an ether or resembles an alkoxyl, such as can be represented by one of —O-alkyl, —O-alkenyl, and —O-alkynyl. The terms "aroxy" and "aryloxy", as used interchangeably herein, can be represented by —O-aryl or O-heteroaryl, wherein aryl and heteroaryl are as defined below. The alkoxy and aroxy groups can be substituted as described above for alkyl.

As used herein, "amine" and "amino" (and its protonated form) are art-recognized and refer to both unsubstituted and substituted amines, e.g., a moiety that can be represented by the general formula:

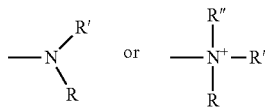

wherein R, R', and R" each independently represent a hydrogen, an alkyl, an alkenyl, —(CH$_2$)$_m$—R$_C$ or R and R' taken together with the N atom to which they are attached complete a heterocycle having from 4 to 8 atoms in the ring structure; R$_C$ represents an aryl, a cycloalkyl, a cycloalkenyl, a heterocycle or a polycycle; and m is zero or an integer in the range of 1 to 8. In some embodiments, only one of R or R' can be a carbonyl, e.g., R, R' and the nitrogen together do not form an imide. In other embodiments, the term "amine" does not encompass amides, e.g., wherein one of R and R' represents a carbonyl. In further embodiments, R and R' (and optionally R") each independently represent a hydrogen, an alkyl or cycloakyl, an alkenyl or cycloalkenyl, or alkynyl. Thus, the term "alkylamine" as used herein means an amine group, as defined above, having a substituted (as described above for alkyl) or unsubstituted alkyl attached thereto, i.e., at least one of R and R' is an alkyl group.

As used herein, "amido" is art-recognized as an amino-substituted carbonyl and includes a moiety that can be represented by the general formula:

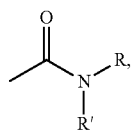

wherein R and R' are as defined above.

As used herein, "Aryl" can refer to C$_5$-C$_{10}$-membered aromatic, heterocyclic, fused aromatic, fused heterocyclic, biaromatic, or bihetereocyclic ring systems. Broadly defined, "aryl", as used herein, includes 5-, 6-, 7-, 8-, 9-, and 10-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine, pyrimidine, and the like. Those aryl groups having heteroatoms in the ring structure may also be referred to as "aryl heterocycles" or "heteroaromatics." The aromatic ring can be substituted at one or more ring positions with one or more substituents including, but not limited to, halogen, azide, alkyl, aralkyl, alkenyl, alkynyl, cycloalkyl, hydroxyl, alkoxyl, amino (or quaternized amino), nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF$_3$, —CN, and combinations thereof.

The term "aryl" can also include polycyclic ring systems having two or more cyclic rings in which two or more carbons are common to two adjoining rings (i.e., "fused rings") wherein at least one of the rings is aromatic, e.g., the other cyclic ring or rings can be cycloalkyls, cycloalkenyls, cycloalkynyls, aryls and/or heterocycles. Examples of heterocyclic rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, and xanthenyl. One or more of the rings can be substituted as defined above for "aryl."

As used herein, "aralkyl," can refer to an alkyl group substituted with an aryl group (e.g., an aromatic or heteroaromatic group).

As used herein, "aralkyloxy" can be represented by —O-aralkyl, wherein aralkyl is as defined above.

As used herein, "carbocycle," can refer to an aromatic or non-aromatic ring(s) in which each atom of the ring(s) is carbon.

As used herein, "heterocycle" or "heterocyclic" can refer to a monocyclic or bicyclic structure containing 3-10 ring atoms, and in some embodiments, containing from 5-6 ring atoms, wherein the ring atoms are carbon and one to four heteroatoms each selected from the following group of non-peroxide oxygen, sulfur, and N(Y) wherein Y is absent or is H, O, (C$_1$-C$_{10}$) alkyl, phenyl or benzyl, and optionally containing 1-3 double bonds and optionally substituted with one or more substituents. Examples of heterocyclic rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxepanyl, oxetanyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydropyranyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, and xanthenyl. Heterocyclic groups can optionally be substituted with one or more substituents at one or more positions as defined above for alkyl and aryl, for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The term "carbonyl" is art-recognized and includes such moieties as can be represented by the general formula:

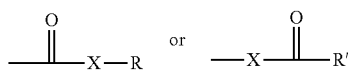

wherein X is a bond or represents an oxygen or a sulfur, and R and R' are as defined above. Where X is an oxygen and R or R' is not hydrogen, the formula represents an "ester". Where X is an oxygen and R is as defined above, the moiety is referred to herein as a carboxyl group, and particularly when R is a hydrogen, the formula represents a "carboxylic acid." Where X is an oxygen and R' is hydrogen, the formula represents a "formate." In general, where the oxygen atom of the above formula is replaced by sulfur, the formula represents a "thiocarbonyl" group. Where X is a sulfur and R or R' is not hydrogen, the formula represents a "thioester." Where X is a sulfur and R is hydrogen, the formula represents a "thiocarboxylic acid." Where X is a sulfur and R' is hydrogen, the formula represents a "thioformate." On the other hand, where X is a bond, and R is not hydrogen, the above formula represents a "ketone" group. Where X is a bond, and R is hydrogen, the above formula represents an "aldehyde" group.

As used herein, "heteroatom" as used herein can refer to an atom of any element other than carbon or hydrogen. Exemplary heteroatoms include, but are not limited to, boron, nitrogen, oxygen, phosphorus, sulfur, silicon, arsenic, and selenium.

As used herein, "nitro" can refer to —NO$_2$; the term "halogen" designates —F, —Cl, —Br, or —I; the term "sulfhydryl" refers to —SH; the term "hydroxyl" refers to —OH; and the term "sulfonyl" refers to —SO$_2$—.

The term "substituted" as used herein, can refer to all permissible substituents of the compounds described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, e.g. 1-14 carbon atoms, and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, amino acid, peptide, and polypeptide groups.

Heteroatoms, such as nitrogen, can have hydrogen substituents and/or any permissible substituents of organic compounds described herein which satisfy the valences of the heteroatoms. It is understood that "substitution" or "substituted" includes the implicit proviso that such substitution is in accordance with permitted valence of the substituted atom and the substituent, and that the substitution results in a stable compound, i.e., a compound that does not spontaneously undergo transformation such as by rearrangement, cyclization, elimination, etc.

As used herein, "suitable substituent" can refer to a chemically and pharmaceutically acceptable group, i.e., a moiety that does not significantly interfere with the preparation of or negate the efficacy of the inventive compounds. Such suitable substituents may be routinely chosen by those skilled in the art. Suitable substituents include but are not limited to the following: a halo, $C_1$-$C_6$ alkyl, $C_2$-$C_6$ alkenyl, $C_1$-$C_6$ haloalkyl, $C_1$-$C_6$ alkoxy, $C_1$-$C_6$ haloalkoxy, $C_2$-$C_6$ alkynyl, $C_3$-$C_8$ cycloalkenyl, ($C_3$-$C_8$ cycloalkyl)$C_1$-$C_6$ alkyl, ($C_3$-$C_8$ cycloalkyl)$C_2$-$C_6$ alkenyl, ($C_3$-$C_8$ cycloalkyl) $C_1$-$C_6$ alkoxy, $C_3$-$C_7$ heterocycloalkyl, ($C_3$-$C_7$ heterocycloalkyl) $C_1$-$C_6$ alkyl, ($C_3$-$C_7$ heterocycloalkyl)$C_2$-$C_6$ alkenyl, ($C_3$-$C_7$ heterocycloalkyl)$C_1$-$C_6$ alkoxyl, hydroxy, carboxy, oxo, sulfanyl, $C_1$-$C_6$ alkylsulfanyl, aryl, heteroaryl, aryloxy, heteroaryloxy, arylalkyl, heteroaralkyl, arylalkoxy, heteroaralkoxy, nitro, cyano, amino, $C_1$-$C_6$ alkylamino, di-($C_1$-$C_6$ alkyl)amino, carbamoyl, ($C_1$-$C_6$ alkyl)carbonyl, ($C_1$-$C_6$ alkoxy)carbonyl, ($C_1$-$C_6$ alkyl)aminocarbonyl, di-($C_1$-$C_6$ alkyl)aminocarbonyl, arylcarbonyl, aryloxycarbonyl, ($C_1$-$C_6$ alkyl)sulfonyl, and arylsulfonyl. The groups listed above as suitable substituents are as defined hereinafter except that a suitable substituent may not be further optionally substituted.

As used herein, "optionally substituted" can indicate that a group may be unsubstituted or substituted with one or more substituents as defined herein.

DISCUSSION

Alzheimers Disease (AD) is a neurodegenerative disease that is associated with age and leads to behavior and personality changes, a decline in cognitive abilities and ultimately a severe loss of mental function. These symptoms are correlated to the gradual breakdown of the connections between certain neurons in the brain and their eventual death. AD patients die from complications associated with the loss of neurons. Although much research effort has been devoted to studying the pathology of AD and other neurological disorders, there remains to be a consensus on the etiology and pathology of AD and many other neurodegenerative diseases. Further, the only drugs that are FDA approved are only effective to manage symptoms to improve the quality of life of the patient and do not address the underlying disorder.

Long non-coding RNAs (lncRNAs) have varied functions including signaling, molecular decoys, scaffolding and guiding ribonucleoprotein complexes. Cellular RNAs are divided into coding (mRNA, 2%) and noncoding RNA (98%). Noncoding RNAs are subdivided into transcription RNAs (rRNA and tRNA), long noncoding RNAs and short noncoding RNAs (miRNA, siRNA, snoRNA, snRNA). LncRNAs are greater than about 200 nucleotides in length and have distinct structural and spatial features which allow it to bind to DNA, RNA, or protein partners. Genome wide association studies done in suggested that lncRNAs are important orchestrators of essential biological networks. For example, lncRNAs are implicated in regulation of genes in cell growth and apoptosis, epigenetic regulation, transcription and translation, and splicing. LncRNAs are transcribed by all cell types but its target and mode of action is specific for that biological system. Currently, the involvement of lncRNAs in the etiology or pathology of AD and other neurodegenerative diseases is not well characterized at best and not known at all at worst.

With that said, described herein are assays and methods for diagnosing/prognosing AD and/or another neurodegenerative disease in a subject. In some embodiments, a lncRNA can be detected and/or quantified in a bodily fluid of a subject having, predisposed to, or suspected of having AD and/or another neurodegenerative disease is made based on the detection and/or quantification of a long non-coding RNA, such as gas5 lncRNA. In some instances, the assays and/or methods can be used to evaluate a response to treatment or management for AD and/or other neurodegenerative diseases in a subject receiving said treatment.

Also described herein are compounds that can bind the GAS5 lncRNA, formulations thereof, and uses thereof. The compounds can be capable of modulating the interaction of GAS5 RNA with other enzymes and compounds such that the amount and/or the activity of the GAS5 lncRNA is altered from its normal or a baseline state. The compounds and formulations thereof provided herein can be administered to a subject in need thereof.

Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

Assays

Described herein are assays for detecting biomarkers of a neurodegerative disease, including but not limited to AD. Also described herein are assays for diagnosing and/or prognosing AD and/or other neurodegenerative diseases. The assays can be used for the diagnosing a AD and/or other neurodegenerative diseases and/or risk of developing AD and/or other neurodegenerative diseases. The assays described herein can also be used for diagnosing a state of AD and/or other neurodegenerative diseases or determining a response to a treatment for AD and/or other neurodegenerative diseases or a symptom thereof. The assays can also be used for diagnosing an early onset AD. Alteration in the normal expression and/or secretion of gas5 (SNHG2), can be be involved in the etiology and/or pathology of AD and/or other neurodegenerative diseases. Alteration of the expression and/or secretion of one or more of the gas5 lncRNA can occur prior to the development of AD and/or neurodegenerative diseases. Therefore, alteration of the expression and/or secretion of one or more of the gas5 lncRNA can indicate and/or characterize the early stage of AD and/or other neurodegenerative diseases. In short, the assays described herein can provide earlier, improved, and/or more accurate diagnosis and/or prognosis of AD and/or other neurodegenerative disease as compared to conventional methods and assays for the diagnosis and/or prognosis of AD and/or other neurodegenerative diseases.

Capture Molecules

Described herein are capture molecules configured to specifically bind a biomarker that can be involved in the pathogenesis of AD and/or other neurodegenerative diseases. The capture molecule can be a polynucleotide. The polynucleotide can be configured to specifically bind to a biomarker as described herein. The polynucleotide can be configured to make a non-covalent bond or a covalent bond with the biomarker. In some embodiments, the capture molecule(s) can be configured to specifically bind GAS5 lncRNA or cDNA thereof. In some embodiments, the capture molecule can be configured to specifically bind a polynucleotide that is 90%-100% identical to SEQ ID NO.: 1. In some embodiments the capture molecule can be a polynucleotide that is 5-10, 20, 30, 40, 50 or more consecutive base pairs that are complementary to SEQ ID NO.: 1. In some embodiments, the capture molecules can have a sequence 95% to 100% identical to any one of SEQ ID NOs.: 2 or 3. The capture molecule can be modified to include a detection molecule, such as, but not limited to, a chromophore, fluorophore, or bioluminescent molecule, that is activated or quenched upon hybridization of the capture molecule to the biomarker. The detection molecule can facilitate measurement and quantification of the biomarker present in a sample.

Biomarkers

The capture molecules described herein can be configured to specifically bind to a biomarker. The biomarker can be involved in the etiology and/or pathology of a neurodegerative disease including, but not limited to AD. The biomarker can be a polynucleotide. In some embodiments, the biomarker is a long non-coding RNA (lncRNA). In other embodiments, the biomarker is a cDNA molecule corresponding to the lncRNA. In some embodiments, the cDNA molecule does not contain intron sequences present in an underlying genomic sequence from which the RNA molecule is transcribed. In some embodiments, the the cDNA can span an intron/exon junction of a coding gene. cDNA can be generated via reverse transcription or any other technique and can be generated as a step in an assay described herein.

In some aspects the biomarker can be can be gas5 (SNHG2). A biomarker as specified herein can have a sequence that is about 50%-100%, about 60%-100%, about 70% to 100%, about 80% to 100%, about 85% to 100%, about 90% to about 100%, about 95% to about 100%, about 99% to about 100% identical to any one of SEQ ID NO: 1. In some embodiments, a biomarker as specified herein can have a sequence that corresponds to a sequence that is about 50%-100%, about 60%-100%, about 70% to 100%, about 80% to 100%, about 85% to 100%, about 90% to about 100%, about 95% to about 100%, about 99% to about 100% identical to SEQ ID NO.: 1.

Assays Using the Capture Molecules

The capture molecules described herein can be used in an assay to detect and/or quantify an amount of one or more biomarkers present in a sample obtained from a subject.

LncRNAs can be present within the cell as well as secreted within exosomes by the cell from which they are made. The biomarker can be present in a tissue, a cell, an exosome, a cell secretion, and/or a bodily fluid, body secretion or bodily excretion. The sample can be obtained from bodily fluid, body secretion or bodily excretion, tissue, organ, cell, an in vitro cell culture, conditioned media from an in vitro cell culture, cell secretion, and/or exosome preparation. The sample or component thereof can be obtained from subject having, predisposed to having, or suspected of having Alzheimer's disease and/or another neurodegenerative disease. In other embodiments, the subject can be obese or aging. In some embodiments, the sample or component thereof can be obtained from a non-obese individual.

The assay can contain the steps of contacting a sample with a capture molecule that is configured to specifically bind to a biomarker and detecting the presence of specific binding of the biomarker by the capture molecule as compared to a control. The control can be a positive control, negative control, or an assay control. In some embodiments, the negative control can include a capture molecule that specifically binds to a molecule not involved in the pathogenesis and/or etiology of AD and/or other neurodegenerative diseases. In some embodiments, the positive control can contain a capture molecule that specifically binds to a molecule known to be involved in the pathogenesis and/or etiology of AD and/or other neurodegenerative diseases. In some embodiments, the negative control can include a sample obtained from a subject not having a neurodegerative disease, including but not limited to AD. In some embodiments, the negative control can include a sample obtained from a subject not predisposed to AD and/or other neurodegenerative diseases. In some embodiments, the positive control can include a sample from a subject known to have AD and/or other neurodegenerative diseases. In other embodiments, the positive control can include a sample obtained from a subject known to be predisposed to AD and/or other neurodegenerative diseases. In some embodiments, the positive control can be cells, such as neurons, over-expressing GAS5 (generated using techniques generally known in the art including, but not limited to, transfection of cells with a GAS5 expression plasmid). In some embodiments, the negative control can be cells having depleted GAS5 (generated using techniques generally known in the art including, but not limited to, transfection of GAS5 siRNA/shRNA/anti-sense oligonucleotide, or other forms of gas5 knock down or knock-out cells, which are generally known in the art). The assay can be configured to aid in the diagnosis, treatment, management, or prognosis of a neurodegerative disease including, but not limited to, AD by the specific capture molecule or combination of capture molecules included in the assay.

The assay can also contain the step of processing the sample prior to contacting the sample with the capture molecule. In steps where the sample is further processed, a part of the further processed sample is contacted with the capture molecule as opposed to the entire unprocessed sample. The step of processing the sample can include processing the sample to obtaining a fraction of the sample that contains the biomarker and/or processing the sample (or fraction thereof) to isolate the type of molecules that include the biomarkers or interest.

Where the sample is a blood sample, processing the sample can include separating the blood sample into a plasma, buffy coat, and/or serum fractions by a suitable method. Suitable methods for processing blood samples are generally known in the art.

Where the sample is a tissue, organ, or cell, the tissue, organ, or cell can be further processed prior to contacting the sample with the capture molecule. The tissue, organ, or cell, can be fixed in a suitable fixing solution, embedded in a suitable material, or frozen prior to contacting the capture molecule with the sample. Suitable fixing solutions and embedding material can work preserve the integrity of the RNA and are generally known in the art. The fixed or frozen tissue, organ, or cell can be sectioned and/or attached to a suitable solid support. Suitable solid supports and methods of attachment are generally known in the art.

Following transcription in the nucleus, the lncRNAs are transported in the cytoplasm in small membrane vesicles of about 40-100 nm secreted by most cells in vivo and in vitro. The exosomes are the smallest vesicles with increasing sizes of microvesicles and multivesicular bodies. Exosomes can be found in bodily fluids, including, but not limited to blood, urine, ascite fluid. LncRNAs can be found within the exosomes. In some embodiments, processing the sample can include isolating the exosomes by a suitable method. Exosomes can be isolated directly from the sample or fraction thereof. Suitable methods for obtaining exosomes circulating in the blood, present in neuronal tissue and/or brain tissue, from a sample are generally known in the art The sample or processed sample can be further processed using any suitable chemical method, physical method, or combinations thereof to release, concentrate, separate and/or isolate the biomarker. In some embodiments, the step of isolating RNA from the sample can include isolating total RNA, mRNA, lncRNA, snRNA, miRNA, or any other particular species or combinations thereof of RNA by a suitable method. Suitable methods for isolating RNA species are generally known in the art.

In some embodiments, the assay also contains the step of making a complementary polynucleotide to one or more RNA molecules and/or one or more DNA molecules within the sample or separated component thereof. cDNA or cRNA can be generated by, for example, reverse-transcription of RNA or in vitro transcription of DNA, respectively.

The assay can also contain the step of quantifying or calculating an amount of a biomarker present in the sample and/or the step of quantifying an amount of biomarker that is specifically bound to a capture molecule. In some embodiments, the amount of biomarker present in the sample is quantified by quantifying the amount of biomarker that is specifically bound to a capture molecule. Specific binding of the biomarker and the capture molecule can result in a measurable, detectable, and/or quantifiable signal. Methods of quantifying the amount of biomarker specifically bound to a capture molecule based on the measureable, detectable, and/or quantifiable signal in a binding assay are generally known in the art.

In some embodiments, the step of detecting the presence of specific binding of the biomarker by the capture molecule and/or the step of detecting, measuring, and/or quantifying the amount of biomarker specifically bound by the capture molecule is performed, at least in part, using a method selected from an array (including microarrays), polymerase chain reaction (PCR), quantitative PCR (qPCR), real-time PCR, real-time qPCR, reverse-transcription PCR (RT-PCR), real-time RT-PCR, RT-qPCR, real-time RT-qPCR, digital PCR (dPCR), RNA flare, (LATE)-PCR, RNA flow cytometry, nucleotide sequencing (including but not limited to transcriptome sequencing and analysis and secretome sequence and analysis, RNASeq), cell-based RNA detection assays, in situ hybridization, northern blot analysis.

The amount of specifically bound biomarker quantified in some of the methods described herein can be an absolute amount of molecules of specifically bound biomarker to a capture molecule or a relative amount of specifically bound biomarker. An absolute amount can be calculated from a standard curve. The relative amount can be determined by normalizing the amount of specifically bound biomarker quantified to an internal standard or reference amount.

The amount of specifically bound biomarker can be about 0% to about 50% less than the control, 50% to 100% less than the control, about 100% to about 500% less than the control, or less than about 500% than the control. The amount of specifically bound biomarker can be about 0% to about 50% greater than the control, about 50% to about 100% greater than the control, about 100% to about 500% greater than the control, or greater than about 500% than the control. Specific binding of the biomarker and the capture molecule can result in a measurable, detectable, and/or quantifiable signal in binding assays, such as immunoassays. Methods of quantifying the amount of biomarker specifically bound to a capture molecule based on a measureable, detectable, and/or quantifiable signal in a binding assay are generally known in the art.

In further embodiments, the assay can contain the steps of contacting a sample or component thereof as described elsewhere herein with one ore more capture molecules and/or a plurality of capture molecules, where each capture molecule is configured to specifically bind to a biomarker that can be involved in the pathogenesis of a neurodegerative disease including, but not limited to, AD, and detecting the presence of specific binding of at least one biomarker by at least one of the capture molecules in the plurality of capture molecules. The biomarker(s) can be, gas5 (SNHG2).

A biomarker as specified herein can have a sequence that is about 50%-100%, about 60%-100%, about 70% to 100%, about 80% to 100%, about 85% to 100%, about 90% to about 100%, about 95% to about 100%, about 99% to about 100% identical to SEQ ID NO.: 1.

In some embodiments, the capture molecule can be configured to bind gas5 lncRNAs (or corresponding cDNA) (e.g. a gas5 biomarker). The biomarker to which the capture molecule can be configured to bind can have a sequence that is about 50%-100%, about 60%-100%, about 70% to 100%, about 80% to 100%, about 85% to 100%, about 90% to about 100%, about 95% to about 100%, about 99% to about 100% identical to SEQ ID NO.: 1.

The assay can also include the step of administering to a subject from which a sample was obtained and used for the assay one or more of the compounds or pharmaceutical formulations described herein. The subject can have or be suspected of having AD and/or diabetes.

Arrays and Fixed Capture Molecule Assays

Also described herein are arrays, including microarrays, and fixed capture molecule assays that can be used to detect one or more molecules of interest (e.g. biomarkers) present in a sample. In an array, one or more capture molecules are attached to or operatively linked to a support in essentially discrete locations on the support. The capture molecules can be as described elsewhere herein. The biomarkers can be as described elsewhere herein.

In arrays, discrete locations on the support where the capture molecule(s) can be attached to or operatively linked are individually referred to herein as a feature of the array and collectively as features. The features can be arranged in any desired arrangement on the support. The arrangement can be such that each feature has its own coordinate so as to allow identification of the capture molecule and/or biomarker detected at any given discrete location in the array according to the coordinate of the feature. These arrays can also be referred to as "ordered arrays". The features can be arranged on the support to be 0.01 nm to 1 cm apart from another feature on the support. A single feature can contain a single capture molecule (singleplex) or can contain more than one capture molecules (multiplex).

In other embodiments, the location of the feature on the support is not important and thus they can be random. These embodiments are referred to as fixed capture molecule assays. In these embodiments, detection can be made based on the knowledge of what feature(s), and some instances how many, are present on the support. For example, capture molecule(s) can be attached to substrate beads, that when a biomarker specifically binds to a capture molecule on the bead, a signal can be produced. The intensity of the signal and/or type of signal produced (e.g. wavelength) can indicate the biomarker bound and/or quantity.

The support can be solid or semi-solid. The support can be rigid or be flexible. The support can contain one or more specialized layers that affect the functionality or performance of the array. The support can be two-dimensional or three-dimensional. The support can be made of glass, such as silicon dioxide or borosilicate; plastic, such as polystyrene, nylon, polyvinylidene difluoride; a fibrous material, such as cellulose, carboxy methyl cellulose, or nitrocellulose; a gel, such as agarose, a hydrogel, or polyacrylamide, The support can be formed into any desired shape, including but not limited to a square, a rectangle, a circle, a cube, a rectangular prism, or other regular or irregular polygonal shape or its corresponding three-dimensional shape. The support can have a length, a width, a height, a radius, and/or a diameter. The length of the support can range from about 1 µm to about 10 cm. The height of the support can range from about 1 µm to about 10 cm. The width of the support can range from about 1 µm to about 10 cm. The radius of the support can range from about 1 µm to about 10 cm. The diameter of the support can range from about 1 µm to about 10 cm.

The support can contain a single layer to which the capture molecule is attached or operatively linked. In these embodiments, the support can also be referred to as the surface layer. In other embodiments, the support can contain more than one layer. In embodiments with more than one layer, the layer to which the capture molecule is attached or operatively linked is referred to as the surface layer. The surface layer can be modified to affect the interaction and/or reduce non-specific binding between a capture molecule and the support and/or the capture molecule and the biomarker. In some embodiments, surface layer is modified to enhance the interaction between the capture molecule and the surface layer and/or the interaction between the capture molecule and its corresponding biomarker. The modification of the surface layer can also reduce non-specific binding by the capture molecule and/or the biomarker.

In some embodiments, the surface layer is modified with a chemical modification. Suitable chemical modifications include, but are not limited to, reactive hydroxide groups, reactive primary, secondary, tertiary, and/or quaternary amine groups, a monolayer of a reactive antibody including but not limited to anti-glutathione S-transferase (anti-GST) antibodies, reactive epoxide groups, reactive methacrylate groups, aldehyde reactive groups, reactive A/G proteins that bind immunoglobulins, and 3-D film coatings, which are polymeric coatings containing activated covalent binding sites. In some embodiments, 3-D film polymeric coatings include, but are not limited to, polysaccharides and hydrophilic polymers. In some embodiments, the 3-D film activated covalent binding sites include, but are not limited to, N-hydroxy succamide esters. The surface layer can be modified to be positively charged, neutral, or negatively charged. The surface layer can be modified to be hydrophilic, hydrophobic, or to contain a mix of hydrophobic and hydrophilic regions. In some embodiments, the modifications are patterned on the surface layer to form discrete functionalized areas to which the capture molecule is attached or operatively-linked. In some embodiments having mixed hydrophobic and hydrophilic regions, the hydrophilic regions are separated by hydrophobic regions. In other embodiments, having mixed hydrophobic and hydrophilic regions, the hydrophobic regions are separated by hydrophilic regions.

In some embodiments, the surface layer is a gel, including but not limited to agarose, a hydrogel, or polyacrylamide. In some embodiments the support contains multiple discrete gel surface layers. These gel surface layers are also referred to as pads and can be arranged on the support in an ordered arrangement such that each gel pad is a feature of the array. In some embodiments, the same capture molecule(s) are attached to or operatively linked to all the gel pads forming the surface layer of the support. In other embodiments, at least two of the gel pads have at least one different capture molecule attached or operatively linked thereto.

The support can be configured to have one or more three dimensional discrete indentations or depressions in the surface layer. The capture molecule(s) can be attached or operatively linked to the indentation. The three dimensional indentions can be square, rectangular, round, or irregular shaped. The three dimensional indentations can form wells or channels. One or more indentations can be connected to another indentation by a three dimensional connector channel extending between the one or more wells. In some embodiments, the connector channel is a microfluidic channel. In some embodiments, the microfluidic channel contains wicking paper. A dimension of the indentation can range from about 1 µm to about 10 cm. In some embodiments, a length of an indentation ranges from about 1 µm to about 10 cm. In further embodiments, a width of an indentation can range from about 1 µm to about 10 cm. In additional embodiments, a height of an indentation can range from about 1 µm to about 10 cm. In other embodiments, the radius of an indentation can range from about 1 µm to about 10 cm. In further embodiments, the diameter of an indentation can range from about 1 µm to about 10 cm. The indentations can be so dimensioned so as to hold a specific volume. In some embodiments, the specific volume ranges from about 1 nL to about 1,000 mL. In a single array, the indentations can all be about the same dimension. In other embodiments, at least two of the indentations differ in at least one dimension. Any surface of an indentation can be modified as described above with respect to modification of the surface layer.

The support can also contain additional layers beneath the surface layer and within the support. The additional layers can be directly beneath the surface layer or contain other layers, such as the support, between the additional layer and the surface layer. The additional layer can improve the signal to noise ratio, affect signal production produced by the binding of a capture molecule to a biomarker or other substrate, and affect other properties or performance parameters of the array. In some embodiments the additional layer is a dielectric layer. The dielectric layer can improve the reflection of the signal produced upon binding of a capture molecule and a biomarker.

In some embodiments, the array can be a tissue microarray, which refers to a block of paraffin or other tissue embedding material that contains at least two tissue samples, where the tissue samples are positioned at discrete locations and arranged in a known order. The tissue samples can be core biopsies. The block can then be sliced and a slice of this block can be attached to or operatively linked to a suitable solid support. Suitable solid supports are described elsewhere herein. The block or slice thereof can then be contacted with a capture molecule and specific binding of a biomarker and the capture molecule can be detected. In some embodiments, more than one slices of the block are attached or operatively linked to the solid support.

In some embodiments, the support having one or more capture molecules attached or operatively linked can be incorporated and/or disposed upon the surface of a device, including without limitation, within a well, chamber, or pizoelectric element, and/or microfluidic channel of of a microfluidic or other device.

Methods of Diagnosing and Prognosing AD and/or other Neurodegenerative Diseases

Also described herein are methods of diagnosing and/or prognosing AD and/or other neurodegenerative diseases in a subject. The methods can also determine the effect of treatment or management on the state of or development of a neurodegerative disease including, but not limited to, AD. The methods of diagnosing and/or prognosing a neurodegerative disease including, but not limited to, AD in a subject can be performed using one or more of the capture molecules, assays, kits, and arrays described herein.

Some methods of diagnosing and/or prognosing AD and/or other neurodegenerative diseases in a subject can include the steps of contacting a sample with a capture molecule configured to bind a biomarker as described herein, detecting the presence or absence of the specific binding of the biomarker by the capture molecule, and diagnosing a neurodegerative disease including, but not limited to, AD when the presence or absence of specific binding of the biomarker by the capture molecule is detected as compared to a control. In some embodiments, gas5 RNA (or corresponding cDNA) can be detected in the sample.

Further methods of diagnosing and/or prognosing AD and/or other neurodegenerative diseases can include the steps of contacting a sample or component thereof with a capture molecule configured to specifically bind a biomarker as described herein, detecting the presence or absence of specific binding of the biomarker by the capture molecule, quantifying an amount of biomarker specifically bound by the capture molecule, and diagnosing and/or prognosing a subject with d AD and/or other neurodegenerative diseases when the amount of specifically bound biomarker is greater than the amount of specifically bound biomarker in a control. In some embodiments, a diagnosis and/or prognosis of AD and/or other neurodegenerative diseases can be made when the amount of specifically bound gas 5 (snhg2) is greater than the amount of specifically bound gas 5 (snhg2), 21A, anti-nos2a, hotair, neat1, lincrna-ror, 7s1, and/or lincrna-vldr RNA (or corresponding cDNA) in the control. In further embodiments, a diagnosis and/or prognosis of AD and/or other neurodegenerative diseases can be made when the amount of specifically bound gas 5 (snhg2) is greater than the amount of specifically bound gas5 (snhg2) in a standard and/or predetermined threshold amount.

The amount of specifically bound biomarker quantified in some of the methods described herein can be an absolute amount of molecules of specifically bound biomarker to a capture molecule or a relative amount of specifically bound biomarker. An absolute amount can be calculated from a standard curve. The relative amount can be determined by normalizing the amount of specifically bound biomarker quantified to an internal standard, reference amount, and/or amount of another biomarker in the same or different sample.

The amount of specifically bound biomarker can be about 0% to about 50% less than the control, 50% to 100% less than the control, about 100% to about 500% less than the control, or less than about 500% than the control. The amount of specifically bound biomarker can be about 0% to about 50% greater than the control, about 50% to about 100% greater than the control, about 100% to about 500% greater than the control, or greater than about 500% than the control. Specific binding of the biomarker and the capture molecule can result in a measurable, detectable, and/or quantifiable signal in binding assays, such as immunoassays. Methods of quantifying the amount of biomarker specifically bound to a capture molecule based on a measureable, detectable, and/or quantifiable signal in a binding assay are generally known in the art.

The sample can be obtained from bodily fluid, bodily secretion, bodily excretion, tissue, organ, cell, an in vitro cell culture, conditioned media from an in vitro cell culture, cell secretion, and/or exosome preparation. The sample or component thereof can be obtained from subject having, predisposed to having, or suspected of having diabetes, metabolic syndrome, Alzheimer's disease, and/or another neurological disorder. In some embodiments, the subject can be obese or aging.

The control can be a positive control, negative control, or an assay control. In some embodiments, the negative control can include a capture molecule that specifically binds to a molecule not involved in the pathogenesis and/or etiology of AD and/or other neurodegenerative diseases. In some embodiments, the positive control can contain a capture molecule that specifically binds to a molecule known to be involved in the pathogenesis and/or etiology of AD and/or other neurodegenerative diseases. In some embodiments, the negative control can include a sample obtained from a subject not having AD and/or other neurodegenerative diseases. In some embodiments, the negative control can include a sample obtained from a subject not predisposed to AD and/or other neurodegenerative diseases. In some embodiments, the positive control can include a sample from a subject known to have AD and/or other neurodegenerative diseases. In other embodiments, the positive control can include a sample obtained from a subject known to be predisposed to AD and/or other neurodegenerative diseases. In some embodiments, the positive control can be cells (e.g. neuronal cells) over-expressing GAS5 (generated using techniques generally known in the art including, but not limited to, transfection of adipocytes with a GAS5 expression plasmid). In some embodiments, the negative control can be celles (e.g. neuronal cells) having depleted GAS5 (generated using techniques generally known in the art including, but not limited to, transfection of GAS5 siRNA/shRNA/anti-sense oligonucleotide).

The method can also include the step of administering to a subject from which a sample was obtained and used for the method one or more of the compounds or pharmaceutical formulations described herein. The subject can have or be suspected of having AD and/or diabetes.

Methods of Treating and/or Preventing AD using a GAS5 Assay

Also provided herein are methods that can include the steps of contacting a sample from a subject or component thereof with a capture molecule, where the capture molecule is configured to specifically bind to a biomarker, where the biomarker is gas5 (SNHG2); detecting specific binding of the biomarker to the capture molecule; quantifying an amount of the biomarker that is specifically bound to the capture molecule; and administering a compound to treat AD or a symptom thereof to the subject when the amount of gas5 is determined to be less than normal (e.g. non-AD or healthy levels), such as that contained in a negative control that is obtained from a subject not having AD. In some embodiments, administering a compound to treat AD or a symptom thereof to the subject is carried out when the amount of gas5 in the sample from the subject is determined to be about the same as in a positive control, which contains the an amount of Gas5 as a sample obtained from a subject having AD or is a sample from one or more subjects having AD. Exemplary AD therapeutic compounds include cholinesterase inhibitors (e.g. Aricept (donepezil), Exelon (rivastigmine), and Razadyne (galantamine)), memantine (Namenda), and a combination of a cholinesterase inhibitor and memantine (e.g. Namzaric).

The method can also include the step of administering to a subject from which a sample was obtained and used for the method one or more of the compounds or pharmaceutical formulations described herein. The subject can have or be suspected of having AD and/or diabetes.

Kits

Also described herein are kits containing one or more capture molecules described herein. In some embodiments, the kit can contain one or more antibodies or fragments thereof configured to specifically bind a biomarker described herein. The kit can contain one or more capture molecules configured to specifically bind one or more biomarkers described herein. In some embodiments, the kit can contain a capture molecule configured to bind to at gas5 (or cDNA thereof). In some embodiments, the one or more capture molecules can be polynucleotides. The kit can contain an array, where one ore more capture molecules are operatively coupled to a surface of the array. The array in the kit can contain one or more capture molecules configured to bind a gas5 biomarker.

The kit can also contain a reagent for performing an array (including microarrays), polymerase chain reaction (PCR), quantitative PCR (qPCR), real-time PCR, real-time qPCR, reverse-transcription PCR (RT-PCR), real-time RT-PCR, RT-q PCR, real-time RT-q PCR, digital PCR (dPCR), RNA flare, (LATE)-PCR, RNA flow cytometry, nucleotide sequencing (including but not limited to transcriptome sequencing and analysis and secretome sequence and analysis, RNASeq), cell-based RNA detection assays, in situ hybridization, northern blot analysis, mass spectrometry, or combinations thereof. The kit can contain instructions fixed in a tangible medium of expression where the instructions provide for diagnosing and/or AD and/or other neurodegenerative diseases. The kit can contain instructions fixed in a tangible medium of expression where the instructions provide for direction to administer a compound for treatment of AD or a symptom thereof to the subject from which the sample was obtained.

GAS5 Binding Compounds and Compositions

GAS5 is a lncRNA having about 651 bp and can have a cDNA sequence that can be 90%-100% identical with SEQ ID NO: 1. FIG. 1 shows the secondary structure of a GAS5 lncRNA according to SEQ ID NO: 1. Turnover of GAS5 can be mediated by enzymes that bind to and otherwise interact with the GAS5 lncRNA. One example of such an enzyme is UPF1, which is involved in mediating nonsense mediated RNA decay. The GAS5 lncRNA has a premature termination codon, which can render the GAS5 lncRNA more susceptible to nonsense mediated RNA decay. It has been demonstrated that when UPF1 is depleted that levels of GAS5 lncRNA increase. Additionally, it has been observed that adipocytes from subjects with DM have increased amounts of UPF1 and concurrent decreased amounts of GAS5 lncRNA as compared to non-DM adipocytes.

Provided herein are compounds that can bind GAS5 lncRNA. In some embodiments, the compounds can specifically bind GAS5 lncRNA. The compounds described herein can directly bind (i.e. not via an intermediate molecule) GAS5 lncRNA. In some embodiments, the compounds that can bind GAS5 lncRNA can de-stabilize and/or inhibit binding of an enzyme to the GAS5 lncRNA. In other embodiments, the compounds that can bind GAS5 lncRNA can stabilize, stimulate, and/or facilitate binding of an enzyme to the GAS5 lncRNA. Binding of the GAS5 lncRNA by the compounds provided herein can be capable of altering the half-life of the GAS5 lncRNA and/or total amount of GAS lnRNA present in a cell and/or subject.

In some embodiments, when the compound that can bind the GAS5 lncRNA de-stabilizes and/or inhibits binding of an enzyme to the GAS5 lncRNA binds the GAS5 mRNA the GAS5 mRNA is not degraded and/or its activity is not interrupted. In some of these embodiments, the overall amount of GAS5 lncRNA can be increased as compared to amount present prior to the exposure of the GAS5 lncRNa to a GAS5 binding compound provided herein. In some embodiments, when the compound that can bind the GAS5 lncRNA stabilizes, stimulates, and/or facilitates binding of an enzyme to the GAS5 lncRNA binds the GAS5 lncRNA the GAS5 lncRNA can be degraded and/or the activity of the GAS5 lncRNA can be inhibited. In some of these embodiments, the overall amount of GAS5 lncRNA can be decreased as compared to the amount of GAS5 lncRNA present prior to exposure of the GAS5 lncRNA to a GAS5 binding compound provided herein.

The compound can have a structure according to Formula 1 or be a derivative thereof,

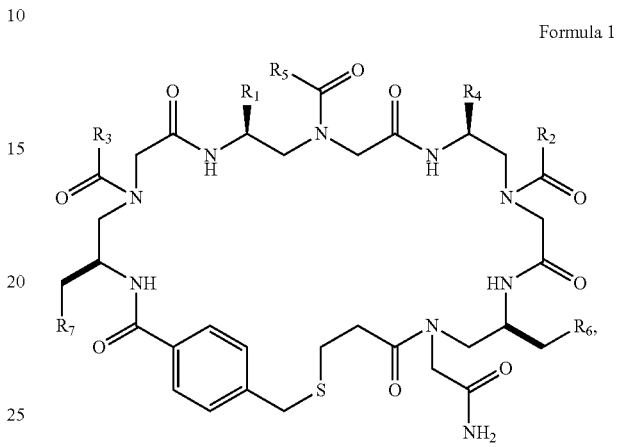

Formula 1 wherein $R_1$ is a methyl, an isobutane, a phenyl, an indole, or a butanamine, wherein $R_2$ is an ethylbenzene, an ethylcyclohexane, an isopentane, a phenyl, a propanamine, or a methylcyclopropane, wherein $R_3$ is a methylcyclopropane, a propionic acid, an ethylbenzene, or a propanamine wherein $R_4$ is a butanamine, a propionic acid, or a phenyl, wherein $R_5$ is a methylcyclopropane, a propionic acid, or an ethylbenzene, wherein $R_6$ is a phenyl, a propionic acid, an isobutene, and wherein $R_7$ is a phenyl, a propionic acid, a butanamine, or a methyl. In some embodiments, the compound can have a structure according to any one of Formulas 3-4, 6-19:

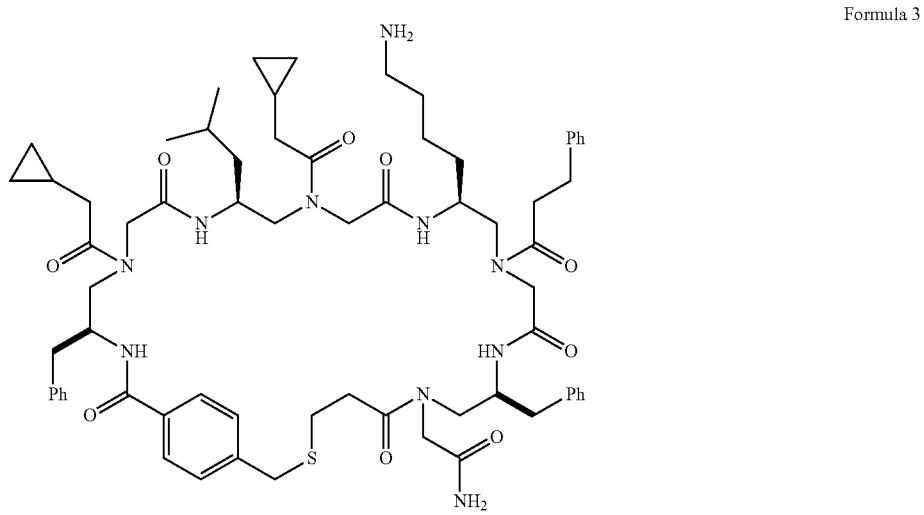

Formula 3

Formula 4
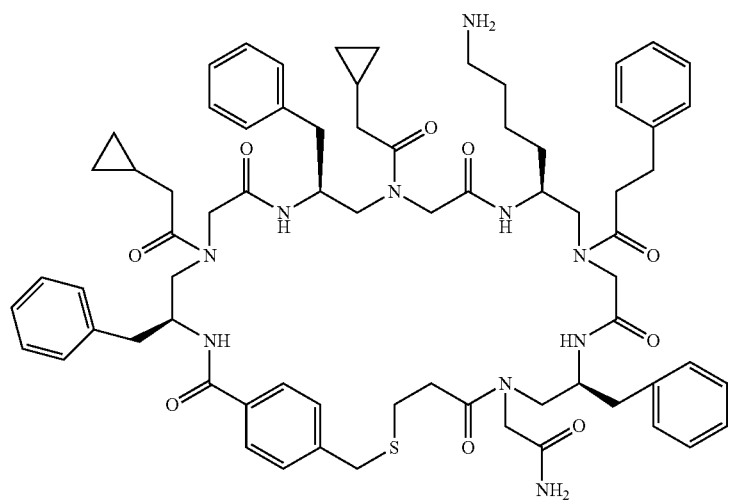
Formula 6
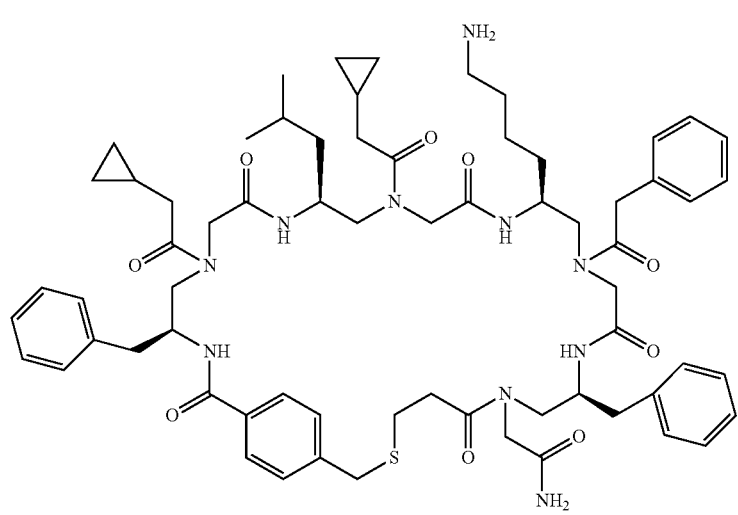
Formula 7
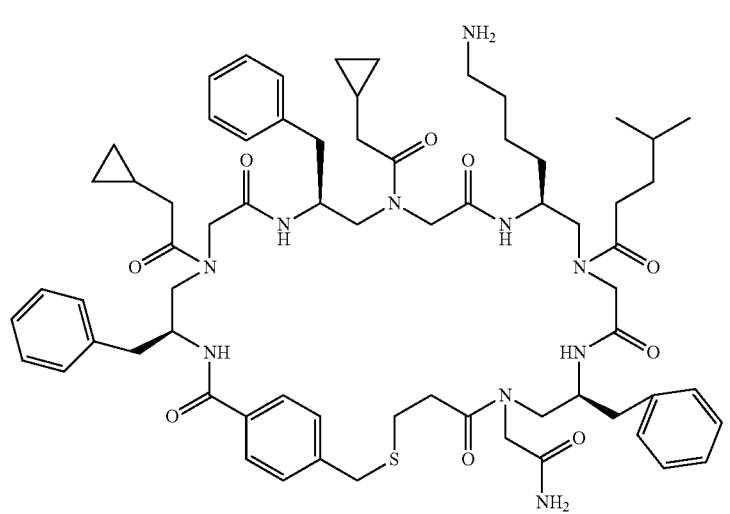

Formula 8
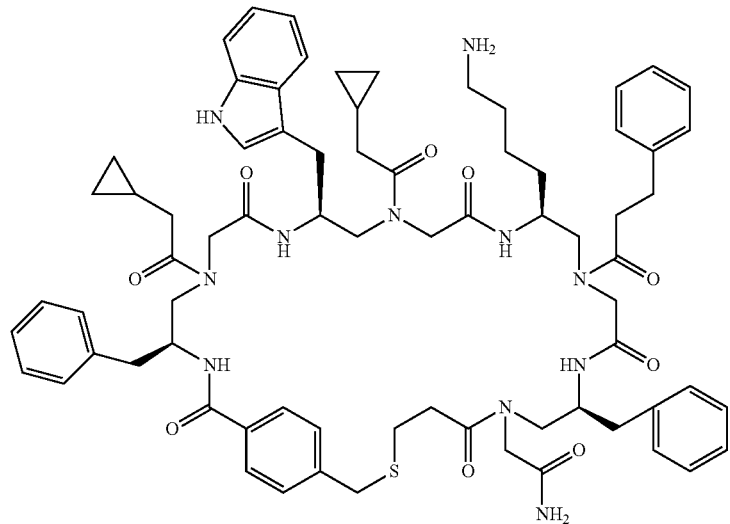
Formula 9
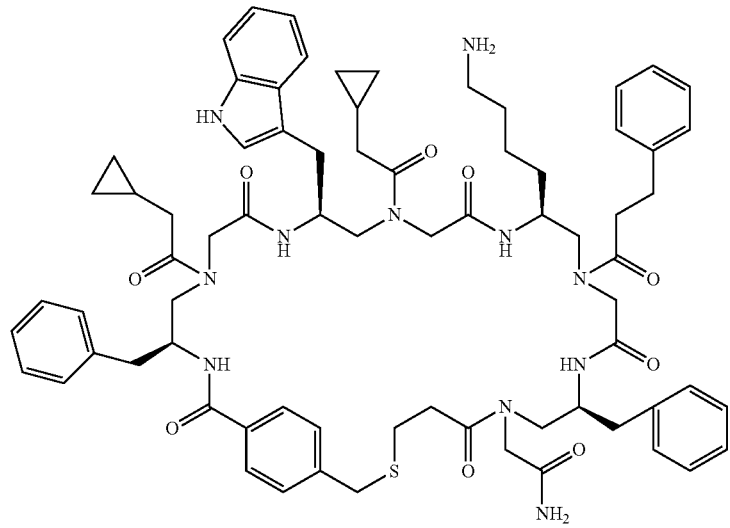
Formula 10
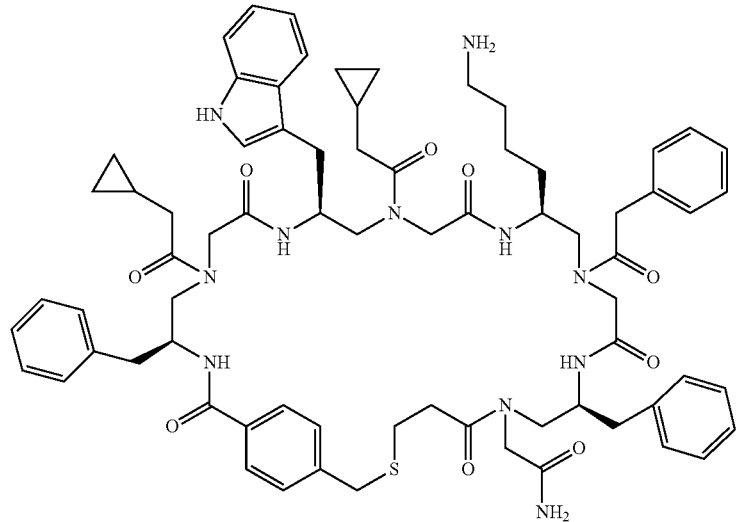

Formula 11
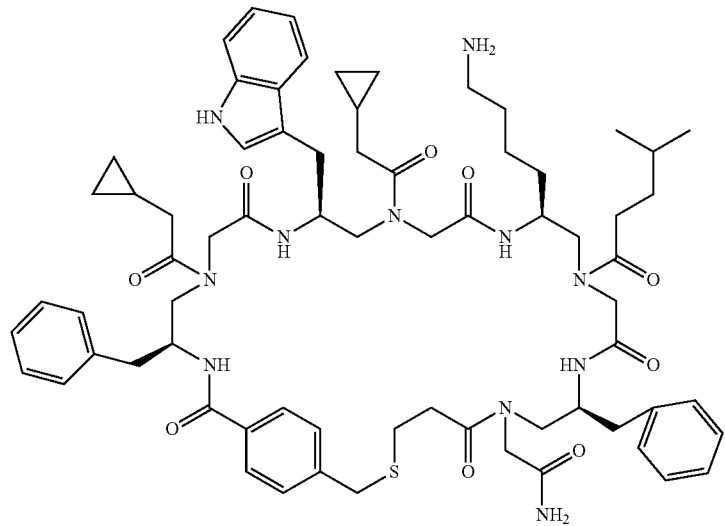
Formula 12
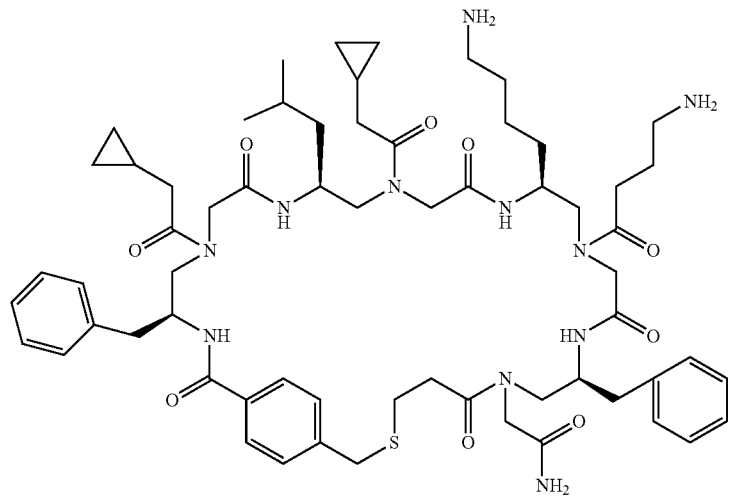
Formula 13
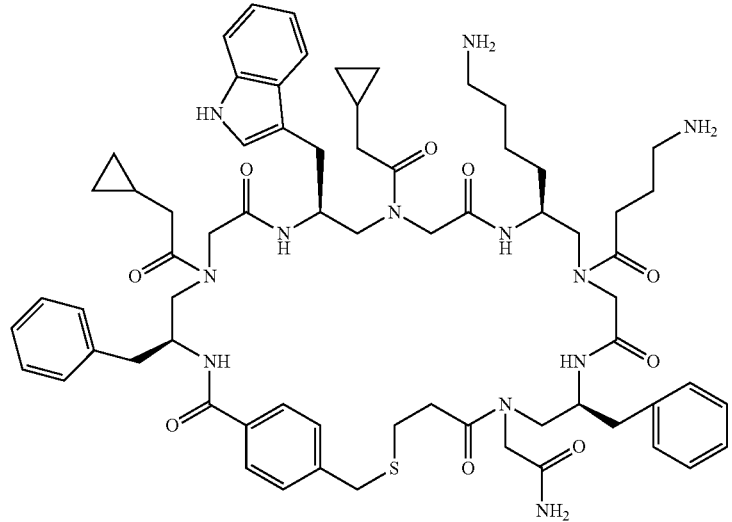

Formula 14
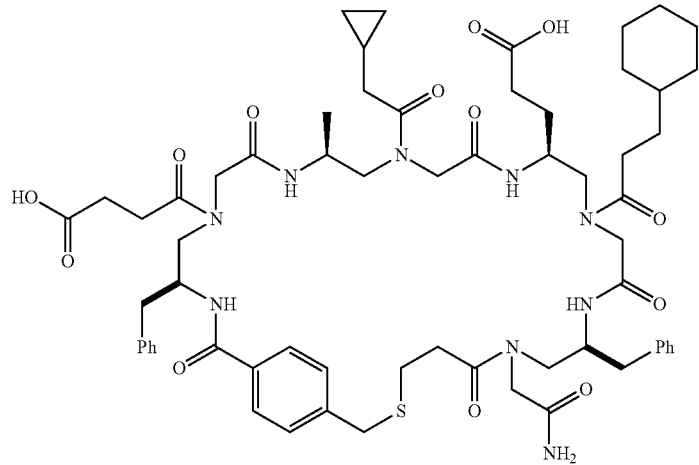
Formula 15
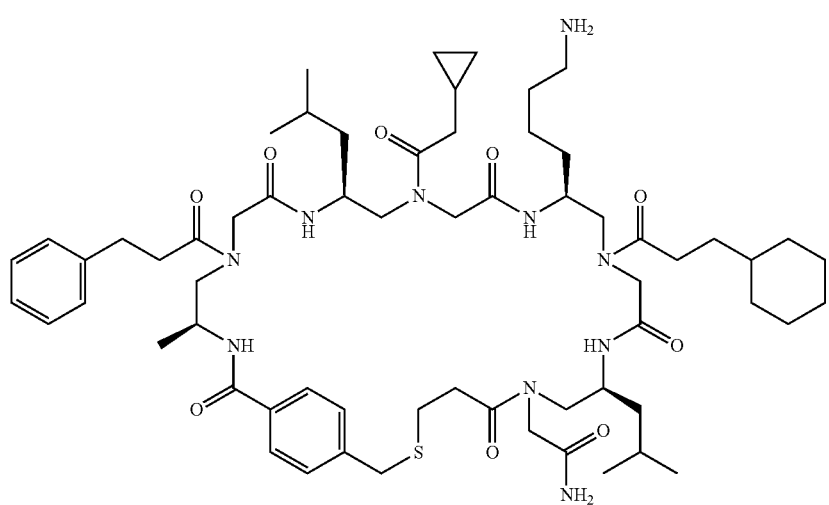
Formula 16
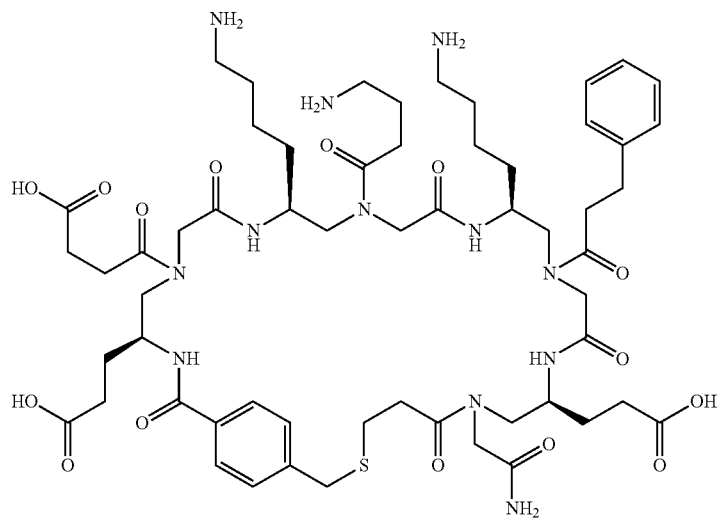

Formula 17
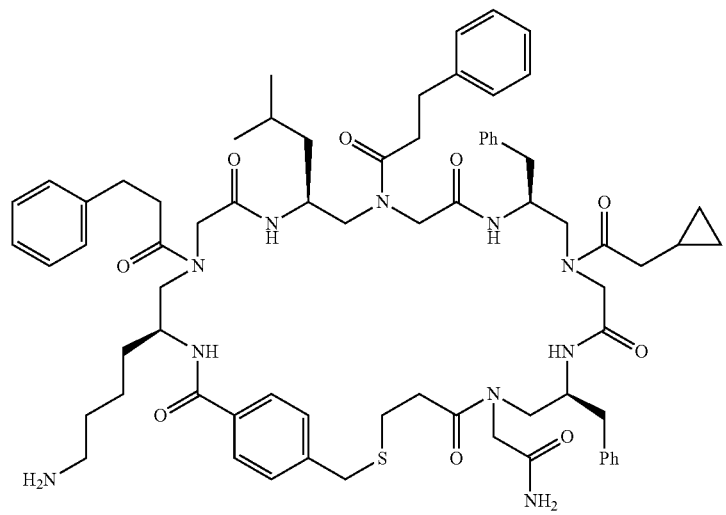
Formula 18
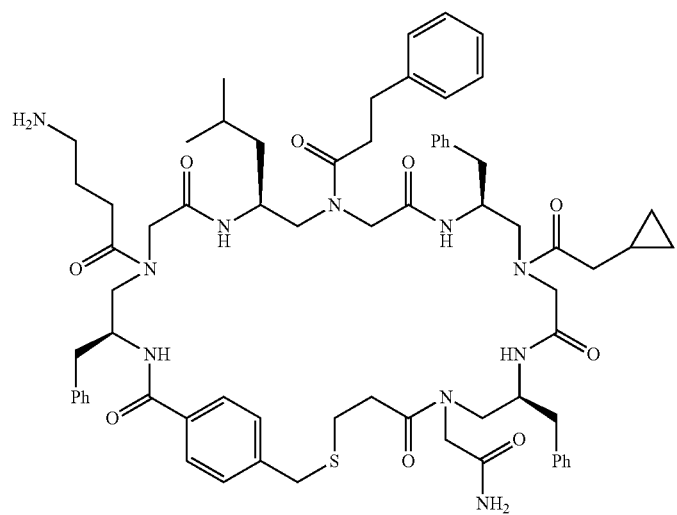

Formula 19

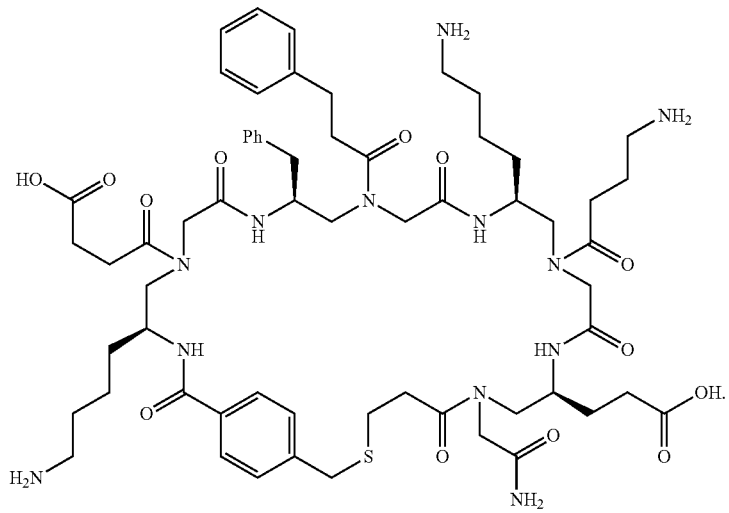

Any compound with a structure according to Formula 1 and any derivative thereof can be substituted with a suitable substituent.

In some embodiments, the compound can have a structure according to Formula 2 or be a derivative thereof, Formula 2

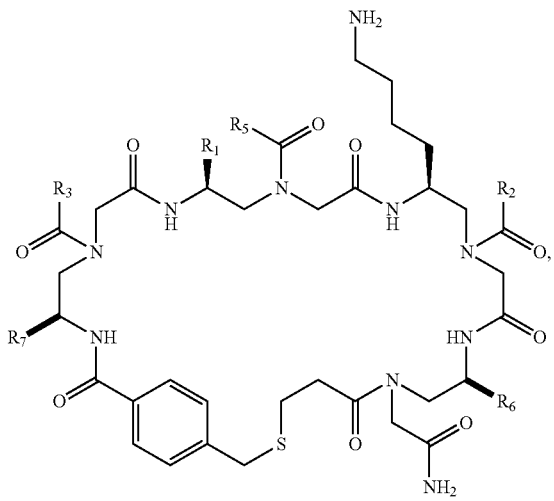

wherein $R_1$ is an isobutane, a phenyl, an indole, or a butanamine, wherein $R_2$ is an ethylbenzene, an ethylcyclohexane, an isopentane, a phenyl, or a propanamine, wherein $R_3$ is a methylcyclopropane, a propionic acid, or an ethylbenzene, wherein $R_5$ is a methylcyclopropane, a propanamine, or an ethylbenzene, wherein $R_6$ is a phenyl, a propionic acid, an isobutene, and wherein $R_7$ is a phenyl, a propionic acid, a butanamine, or a methyl. In some embodiments the compound with a structure according to Formula 2 can have a structure according to any one of Formulas 3, 4, 6, 7, 8, 9, 10, 11, 12, 13, 15, 16, or 19. Any compound with a structure according to Formula 2 and any derivative thereof can be substituted with a suitable substituent.

In some embodiments, the compound can have a structure according to Formula 20 or be a derivative thereof Formula 20

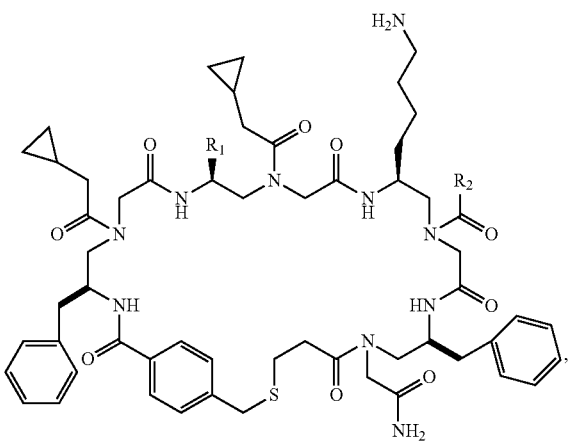

wherein $R_1$ is an isobutene, a phenyl, or an indole and wherein $R_2$ is an ethylbenzene, a phenyl, an isobutene, or a propanamine. In some embodiments the compound with a structure according to Formula 20 can have a structure according to any one of Formulas 3, 4, 6, 7, 8, 9, 10, 11, 12, or 13. Any compound with a structure according to Formula 20 and any derivative thereof can be substituted with a suitable substituent.

In some embodiments, the compound can have a structure according to Formula 21 or be a derivative thereof Formula 21

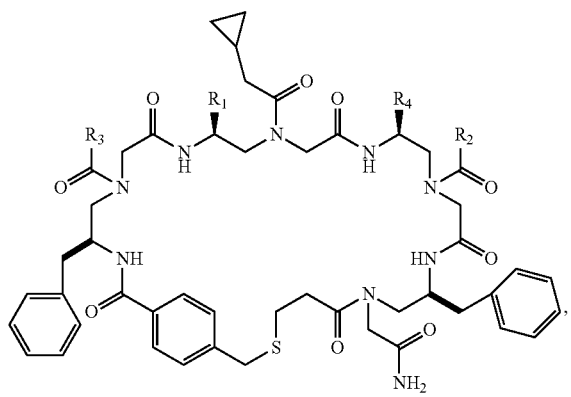

wherein $R_1$ is an isobutene, a phenyl, an indole, or a methyl, wherein $R_2$ is an ethylbenzene, a phenyl, an isobutene, a propanamine, or an ethylcyclohexane, wherein $R_3$ is a methylcyclopropane or a propionic acid, and wherein $R_4$ is a butanamine or a propionic acid. In some embodiments the compound with a structure according to Formula 21 can have a structure according to any one of Formulas 3, 4, 6, 7, 8, 9, 10, 11, 12, 13, or 14. Any compound with a structure according to Formula 21 and any derivative thereof can be substituted with a suitable substituent.

In some embodiments, the compound can have a structure according to Formula 22 or be a derivative thereof Formula 22

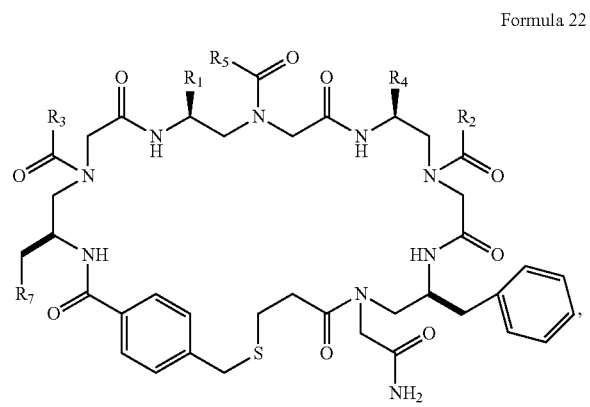

wherein $R_1$ is an isobutene, a phenyl, an indole, or a methyl, wherein $R_2$ is an ethylbenzene, a phenyl, an isobutene, a propanamine, an ethylcyclohexane, or a methylcyclopropane, wherein $R_3$ is a methylcyclopropane, propionic acid, ethylbenzene, or a propanamine, wherein $R_4$, is a butanamine or a propionic acid, and wherein $R_5$ is a methylcyclopropane and ethylbenzene. In some embodiments the compound with a structure according to Formula 22 can have a structure according to any one of Formulas 3, 4, 6, 7, 8, 9, 10, 11, 12, 13, 14, 17, or 18. Any compound with a structure according to Formula 22 and any derivative thereof can be substituted with a suitable substituent.

In some embodiments, the compound can have a structure according to Formula 22 or be a derivative thereof Formula 23

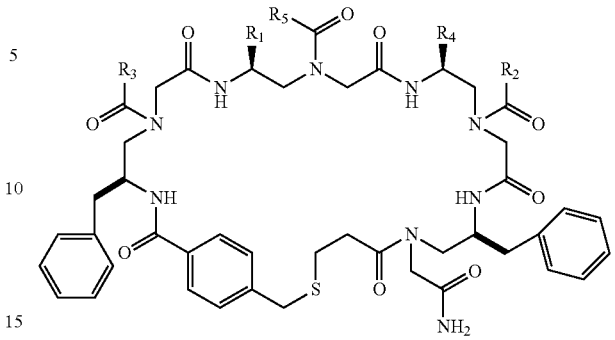

wherein $R_1$ is an isobutene, a phenyl, an indole, or a methyl, wherein $R_2$ is an ethylbenzene, a phenyl, an isobutene, a propanamine, or an ethylcyclohexane, wherein $R_3$ is a methylcyclopropane or a propanamine, wherein $R_4$ is a butanamine or a propionic acid, and wherein $R_5$ is a methyl cyclopropane or an ethylbenzene. In some embodiments the compound with a structure according to Formula 23 can have a structure according to any one of Formulas 3, 4, 6, 7, 8, 9, 10, 11, 12, 13, 14, or 18. Any compound with a structure according to Formula 23 and any derivative thereof can be substituted with a suitable substituent.

Pharmaceutical Formulations

The compounds (e.g. compounds having a structure according to any one of formulas 1-19 and derivatives thereof) described herein can be provided to a subject in need thereof as an ingredient, such as an active ingredient, in a pharmaceutical formulation. As such, also described are pharmaceutical formulations containing one or more of the compounds and salts thereof, or pharmaceutically acceptable salts thereof described herein. Suitable salts include, but are not limited to, sulfate, citrate, acetate, oxalate, chloride, hydrochloride, bromide, hydrobromide, iodide, nitrate, bisulfate, phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, camphorsulfonate, napthalenesulfonate, propionate, malonate, mandelate, malate, phthalate, and pamoate.

The pharmaceutical formulations or salts thereof can be administered to a subject in need thereof. In some embodiments, the subject has and/or is predisposed to developing a neurodegenerative disease such as, but not limited to, AD. In embodiments, the compounds described herein are used in the manufacture of a medicament for the treatment of a neurodegenerative disease, such as but not limited to, AD. In some embodiments, the subject has a lower amount of GAS5 lncRNA as compared to a normal or healthy subject in the blood, population of neuronal cells, brain tissue, and/or other type of tissue or cell.

Pharmaceutically Acceptable Carriers and Auxiliary Ingredients and Agents

The pharmaceutical formulations containing an effective amount of a compound described herein (e.g. compounds having a structure according to any one of formulas 1-19) or a derivative thereof can further include a pharmaceutically acceptable carrier. Suitable pharmaceutically acceptable carriers include, but are not limited to water, salt solutions, alcohols, gum arabic, vegetable oils, benzyl alcohols, polyethylene glycols, gelatin, carbohydrates such as lactose, amylose or starch, magnesium stearate, talc, silicic acid, viscous paraffin, perfume oil, fatty acid esters, hydroxy methylcellulose, and polyvinyl pyrrolidone, which do not deleteriously react with the active composition.

The pharmaceutical formulations can be sterilized, and if desired, mixed with auxiliary agents, such as lubricants, preservatives, stabilizers, wetting agents, emulsifiers, salts for influencing osmotic pressure, buffers, coloring, flavoring and/or aromatic substances, and the like which do not deleteriously react with the active compound.

In addition to the effective amount of a compound and/or derivative thereof, the pharmaceutical formulations can also include an effective amount of auxiliary active agents, including but not limited to, antisense or RNA interference molecules, chemotherapeutics, or antineoplasic agents, hormones, antibiotics, antivirals, immunomodulating agents, antinausea, pain modifying compounds (such as opiates), anti-inflammatory agents, antipyretics, antibiotics, and/or antibodies or fragments thereof.

Effective amounts of the Compounds, Derivatives thereof, and Auxiliary Active Agents The effective amount of the compound ((e.g. compounds having a structure according to any one of formulas 1-19), or derivative thereof contained in the pharmaceutical formulation can range from about 0.001 micrograms to about 1000 grams. In some embodiments, the effective amount of the compound and/or derivative thereof can range from about 0.001 micrograms to about 0.01 micrograms. In other embodiments, the effective amount of compound and/or derivative thereof can range from about 0.01 micrograms to about 0.1 micrograms. In further embodiments, the effective amount of the compound and/or derivative thereof can range from about 0.1 micrograms to about 1.0 grams. In yet further embodiments, the effective amount of the compound and/or derivative thereof can range from about 1.0 grams to about 10 grams. In other embodiments, the effective amount of the compound and/or derivative thereof can range from about 10 grams to about 100 grams. In still other embodiments, the effective amount of the compound and/or derivative thereof can range from about 100 grams to about 1000 grams.

In embodiments where there is an auxiliary active agent contained in the compound or derivative thereof pharmaceutical formulation, the effective amount of the auxiliary active agent will vary depending on the auxiliary active agent. In some embodiments, the effective amount of the auxiliary active agent can range from 0.001 micrograms to about 1000 grams. In other embodiments, the effective amount of the auxiliary active agent can range from about 0.01 IU to about 1000 IU. In further embodiments, the effective amount of the auxiliary active agent can range from 0.001 mL to about 1000 mL. In yet other embodiments, the effective amount of the auxiliary active agent can range from about 1% w/w to about 50% w/w of the total pharmaceutical formulation. In additional embodiments, the effective amount of the auxiliary active agent can range from about 1% v/v to about 50% v/v of the total pharmaceutical formulation. In still other embodiments, the effective amount of the auxiliary active agent can range from about 1% w/v to about 50% w/v of the total pharmaceutical formulation.

The auxiliary active agent can be included in the pharmaceutical formulation or can exist as a stand-alone compound or pharmaceutical formulation that can be administered contemporaneously or sequentially with the compound, derivative thereof, or pharmaceutical formulation thereof. In embodiments where the auxiliary active agent is a stand-alone compound or pharmaceutical formulation, the effective amount of the auxiliary active agent can vary depending on the auxiliary active agent used. In some of these embodiments, the effective amount of the auxiliary active agent can range from 0.001 micrograms to about 1000 grams. In other embodiments, the effective amount of the auxiliary active agent can range from about 0.01 IU to about 1000 IU. In further embodiments, the effective amount of the auxiliary active agent can range from 0.001 mL to about 1000 mL. In yet other embodiments, the effective amount of the auxiliary active agent can range from about 1% w/w to about 50% w/w of the total auxiliary active agent pharmaceutical formulation. In additional embodiments, the effective amount of the auxiliary active agent can range from about 1% v/v to about 50% v/v of the total pharmaceutical formulation. In still other embodiments, the effective amount of the auxiliary active agent can range from about 1% w/v to about 50% w/v of the total auxiliary agent pharmaceutical formulation.

Dosage Forms

In some embodiments, the pharmaceutical formulations described herein can be in a dosage form. The dosage form can be administered to a subject in need thereof. In some embodiments, the subject in need thereof can have or be suspected of having a neurodegenerative disease such as, but not limited to, AD. In some embodiments, the subject can have or be suspected of having diabetes. In some embodiments, the subject can have a lower amount of GAS5 lncRNA as compared to a normal or healthy subject.

The dosage forms can be adapted for administration by any appropriate route. Appropriate routes include, but are not limited to, oral (including buccal or sublingual), rectal, intraocular, inhaled, intranasal, topical (including buccal, sublingual, or transdermal), vaginal, parenteral, subcutaneous, intramuscular, intravenous, internasal, and intradermal. Such formulations can be prepared by any method known in the art.

Dosage forms adapted for oral administration can discrete dosage units such as capsules, pellets or tablets, powders or granules, solutions, or suspensions in aqueous or non-aqueous liquids; edible foams or whips, or in oil-in-water liquid emulsions or water-in-oil liquid emulsions. In some embodiments, the pharmaceutical formulations adapted for oral administration also include one or more agents which flavor, preserve, color, or help disperse the pharmaceutical formulation. Dosage forms prepared for oral administration can also be in the form of a liquid solution that can be delivered as a foam, spray, or liquid solution. The oral dosage form can be administered to a subject in need thereof. In some embodiments, this is a subject having or suspected of having a neurodegerative disease such as, but not limited to, AD. In some embodiments, the subject can have or be suspected of having diabetes. In some embodiments, the subject can have a lower amount of GAS5 lncRNA as compared to a normal or healthy subject.

Where appropriate, the dosage forms described herein can be microencapsulated. The dosage form can also be prepared to prolong or sustain the release of any ingredient. In some embodiments, the compound or derivative thereof is the ingredient whose release is delayed. In other embodiments, the release of an auxiliary ingredient is delayed. Suitable methods for delaying the release of an ingredient include, but are not limited to, coating or embedding the ingredients in material in polymers, wax, gels, and the like. Delayed release dosage formulations can be prepared as described in standard references such as "Pharmaceutical dosage form tablets," eds. Liberman et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et al., (Media, PA: Williams and Wilkins, 1995). These references provide information on excipients, materials, equipment, and processes for preparing tablets and capsules and delayed release dosage forms of tablets and pellets, capsules, and granules. The delayed release can be anywhere from about an hour to about 3 months or more.

Examples of suitable coating materials include, but are not limited to, cellulose polymers such as cellulose acetate phthalate, hydroxypropyl cellulose, hydroxypropyl methylcellulose, hydroxypropyl methylcellulose phthalate, and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Coatings may be formed with a different ratio of water soluble polymer, water insoluble polymers, and/or pH dependent polymers, with or without water insoluble/water soluble non polymeric excipient, to produce the desired release profile. The coating is either performed on the dosage form (matrix or simple) which includes, but is not limited to, tablets (compressed with or without coated beads), capsules (with or without coated beads), beads, particle compositions, "ingredient as is" formulated as, but not limited to, suspension form or as a sprinkle dosage form.

Where appropriate, the dosage forms described herein can be a liposome. In these embodiments, compound, derivative thereof, auxiliary active ingredient, and/or pharmaceutically acceptable salt thereof are incorporated into a liposome. In some embodiments, a compound, derivative thereof, auxiliary active ingredient, and/or pharmaceutically acceptable salts thereof is integrated into the lipid membrane of the liposome. In other embodiments, a compound, derivative thereof, auxiliary active ingredient, and/or pharmaceutically acceptable salt thereof are contained in the aqueous phase of the liposome. In embodiments where the dosage form is a liposome, the pharmaceutical formulation is thus a liposomal formulation. The liposomal formulation can be administered to a subject in need thereof. In some embodiments, this is a subject having or is predisposed to developing a neurodegerative disease such as, but not limited to, AD. In some embodiments, the subject can have a lower amount of GAS5 lncRNA as compared to a normal or healthy subject.

Dosage forms adapted for topical administration can be formulated as ointments, creams, suspensions, lotions, powders, solutions, pastes, gels, sprays, aerosols, or oils. In some embodiments for treatments of the eye or other external tissues, for example the mouth or the skin, the pharmaceutical formulations are applied as a topical ointment or cream. When formulated in an ointment, the compound, derivative thereof, auxiliary active ingredient, and/or pharmaceutically acceptable salt thereof can be formulated with a paraffinic or water-miscible ointment base. In other embodiments, the active ingredient can be formulated in a cream with an oil-in-water cream base or a water-in-oil base. Dosage forms adapted for topical administration in the mouth include lozenges, pastilles, and mouth washes.

Dosage forms adapted for nasal or inhalation administration include aerosols, solutions, suspension drops, gels, or dry powders. In some embodiments, the compound, derivative thereof, auxiliary active ingredient, and/or pharmaceutically acceptable salt thereof in a dosage form adapted for inhalation is in a particle-size-reduced form that is obtained or obtainable by micronization. In some embodiments, the particle size of the size reduced (e.g. micronized) compound or salt or solvate thereof, is defined by a $D_{50}$ value of about 0.5 to about 10 microns as measured by an appropriate method known in the art. Dosage forms adapted for administration by inhalation also include particle dusts or mists. Suitable dosage forms wherein the carrier or excipient is a liquid for administration as a nasal spray or drops include aqueous or oil solutions/suspensions of an active ingredient, which may be generated by various types of metered dose pressurized aerosols, nebulizers, or insufflators. The nasal/inhalation formulations can be administered to a subject in need thereof. In some embodiments, this is a subject having a neurodegerative disease such as, but not limited to AD. In some embodiments, the subject has a lower level of GAS5 lncRNA as compared to a normal or healthy subject.

In some embodiments, the dosage forms are aerosol formulations suitable for administration by inhalation. In some of these embodiments, the aerosol formulation contains a solution or fine suspension of a compound, derivative thereof, auxiliary active ingredient, and/or pharmaceutically acceptable salt thereof a pharmaceutically acceptable aqueous or non-aqueous solvent. Aerosol formulations can be presented in single or multi-dose quantities in sterile form in a sealed container. For some of these embodiments, the sealed container is a single dose or multi-dose nasal or an aerosol dispenser fitted with a metering valve (e.g. metered dose inhaler), which is intended for disposal once the contents of the container have been exhausted.

Where the aerosol dosage form is contained in an aerosol dispenser, the dispenser contains a suitable propellant under pressure, such as compressed air, carbon dioxide, or an organic propellant, including but not limited to a hydrofluorocarbon. The aerosol formulation dosage forms in other embodiments are contained in a pump-atomizer. The pressurized aerosol formulation can also contain a solution or a suspension of a compound, derivative thereof, auxiliary active ingredient, and/or pharmaceutically acceptable salt thereof. In further embodiments, the aerosol formulation also contains co-solvents and/or modifiers incorporated to improve, for example, the stability and/or taste and/or fine particle mass characteristics (amount and/or profile) of the formulation. Administration of the aerosol formulation can be once daily or several times daily, for example 2, 3, 4, or 8 times daily, in which 1, 2, or 3 doses are delivered each time. The aerosol formulations can be administered to a subject in need thereof. In some embodiments, this can be a subject having a neurodegerative disorder, such as but not limited to, AD.

For some dosage forms suitable and/or adapted for inhaled administration, the pharmaceutical formulation is a dry powder inhalable formulations. In addition to the compound, derivative thereof, auxiliary active ingredient, and/or pharmaceutically acceptable salt thereof, such a dosage form can contain a powder base such as lactose, glucose, trehalose, mannitol, and/or starch. In some of these embodiments, the compound, derivative thereof, auxiliary active ingredient, and/or pharmaceutically acceptable salt thereof is in a particle-size reduced form. In further embodiments, a performance modifier, such as L-leucine or another amino acid, cellobiose octaacetate, and/or metals salts of stearic acid, such as magnesium or calcium stearate.

In some embodiments, the aerosol formulations are arranged so that each metered dose of aerosol contains a predetermined amount of an active ingredient, such as the one or more of the compounds described herein.

Dosage forms adapted for vaginal administration can be presented as pessaries, tampons, creams, gels, pastes, foams, or spray formulations. Dosage forms adapted for rectal administration include suppositories or enemas. The vaginal formulations can be administered to a subject in need thereof. In some embodiments, this is a subject having a neurodegerative disease such as, but not limited to, AD. In some embodiments, the subject has a lower level of GAS5 lncRNA as compared to a normal or healthy control.

Dosage forms adapted for parenteral administration and/or adapted for injection can include aqueous and/or non-aqueous sterile injection solutions, which can contain anti-oxidants, buffers, bacteriostats, solutes that render the composition isotonic with the blood of the subject, and aqueous and non-aqueous sterile suspensions, which can include suspending agents and thickening agents. The dosage forms adapted for parenteral administration can be presented in a single-unit dose or multi-unit dose containers, including but not limited to sealed ampoules or vials. The doses can be lyophilized and re-suspended in a sterile carrier to reconstitute the dose prior to administration. Extemporaneous injection solutions and suspensions can be prepared in some embodiments, from sterile powders, granules, and tablets. The parenteral formulations can be administered to a subject in need thereof. In some embodiments, this can be a subject having a neurodegerative disease such as, but not limited to, AD.

For some embodiments, the dosage form contains a predetermined amount of a compound and/or derivative thereof per unit dose. In an embodiment, the predetermined amount of the compound or derivative thereof is an effective amount of the compound and/or derivative thereof to treat, prevent, or mitigate one or more symptoms of a neurodegerative disease, such as but not limited to, AD. In other embodiments, the predetermined amount of the compound and/or derivative thereof can be an appropriate fraction of the effective amount of the active ingredient. Such unit doses may therefore be administered once or more than once a day (e.g. 1, 2, 3, 4, 5, 6, or more times per day). Such pharmaceutical formulations may be prepared by any of the methods well known in the art.

Methods of Making the Compounds and Derivatives Thereof

The compounds (e.g. compounds having a structure according to any one of formulas 1-19) and derivatives thereof can be synthesized via many methods generally known to those of ordinary skill in the art. The present disclosure is not intended to be limited by the particular methods of synthesizing the compounds described herein. The skilled artisan will recognize additional methods of synthesizing the compounds described herein.

Methods of Using the GAS5 Binding Compounds

Any amount of the compounds (e.g. compounds having a structure according to any one of formulas 1-19) or derivatives thereof, pharmaceutical formulations, and/or salts thereof described herein can be administered to a subject in need thereof one or more times per day, week, month, or year. In some embodiments, the amount administered is the effective amount of the compound, derivative thereof, pharmaceutical formulation, and/or salt thereof. For example, the compounds, formulations, or salts thereof, can be administered in a daily dose. This amount may be given in a single dose per day. In other embodiments, the daily dose may be administered over multiple doses per day, in which each containing a fraction of the total daily dose to be administered (sub-doses). In some embodiments, the amount of doses delivered per day is 2, 3, 4, 5, or 6. In further embodiments, the compounds, formulations, or salts thereof are administered one or more times per week, such as 1, 2, 3, 4, 5, or 6 times per week. In other embodiments, the compounds, formulations, or salts thereof are administered one or more times per month, such as 1 to 5 times per month. In still further embodiments, the compounds, formulations, or salts thereof are administered one or more times per year, such as 1 to 11 times per year.

In some embodiments, the subject in need thereof is a subject having or is predisposed to developing a neurodegenerative disease including, but not limited to, AD. In some embodiments the subject in need thereof is a subject having lower GAS5 lncRNA levels as compared to a similar sample obtained from a normal or healthy subject (e.g. one not having a neurodegenerative disease including, but not limited to AD and/or is not predisposed to developing a neurodegenerative disease including, but not limited to AD). In some embodiments, the subject in need thereof has or suspected of having diabetes.

In embodiments where more than one of compounds, formulations, additional therapeutic agents, salts thereof, or pharmaceutically acceptable salts thereof are administered to a subject in need thereof sequentially; the sequential administration may be close in time or remote in time. For example, administration of the second compound, formulation, or other therapeutic agent can occur within seconds or minutes (up to about 1 hour) after administration of the first agent (close in time). In other embodiments, administration of the second compound, formulation, or other therapeutic agent occurs at some other time that is more than an hour after administration of the first agent.

The amount of compounds, formulations, salts thereof (including pharmaceutically acceptable formulations and salts thereof) described herein can be administered in an amount ranging from about 0.01 mg to about 1000 mg per day, as calculated as the free or unsalted compound.

The compounds and formulations described herein can be administered in combinations with or include one or more other auxiliary agents. Suitable auxiliary agents include, but are not limited to antisense or RNA interference molecules, chemotherapeutics, anti-neoplasmic agents, hormones, antibiotics, antivirals, immunomodulating agents, anti-nausea, pain modifying compounds (such as opiates), anti-inflammatory agents, antipyretics, antibiotics, and/or antibodies or fragments thereof. The compound(s), and/or formulation(s), and/or additional therapeutic agent(s) can be administered simultaneously or sequentially by any convenient route in separate or combined pharmaceutical formulations. The additional therapeutic agents can be provided in their optically pure form or a pharmaceutically acceptable salt thereof.

Kits Containing a GAS5 Binding Compound

The compounds (e.g. compounds having a structure according to any one of formulas 1-19, including derivatives thereof) and pharmaceutical formulations described herein can be presented as a combination kit. As used herein, the terms "combination kit" or "kit of parts" refers to the compounds, or pharmaceutical formulations and additional components that are used to package, sell, market, deliver, and/or administer the combination of elements or a single element, such as the active ingredient, contained therein. Such additional components include but are not limited to, packaging, syringes, blister packages, bottles, and the like. When one or more of the components (e.g. active agents) contained in the kit are administered simultaneously, the combination kit can contain the active agents in a single pharmaceutical formulation (e.g. a tablet) or in separate pharmaceutical formulations.

When the agents are not administered simultaneously, the combination kit can contain each agent in separate pharmaceutical formulations. The separate pharmaceutical formulations can be contained in a single package or in separate packages within the kit.

In some embodiments, the combination kit also includes instructions printed on or otherwise contained in a tangible medium of expression. The instructions can provide information regarding the content of the compound or pharmaceutical formulations contained therein, safety information regarding the content of the compound(s) or pharmaceutical formulation(s) contained therein, information regarding the dosages, indications for use, and/or recommended treatment regimen(s) for the compound(s) and/or pharmaceutical formulations contained therein. In some embodiments, the instructions provide directions for administering the compounds, compositions, pharmaceutical formulations, or salts thereof to a subject having, suspected of having, or predisposed to developing a neurodegenarative disease including, but not limited to AD, or a symptom thereof. In some embodiments, the instructions provide directions for administering the compounds, compositions, pharmaceutical formulations, or salts thereof to a subject having, suspected of having, or predisposed to developing diabetes or a symptom thereof. In some embodiments, the instructions provide directions for administering compounds, compositions, pharmaceutical formulations, or salts thereof to a subject having lower GAS5 levels than that of a similar sample obtained from a normal or healthy subject.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

Example 1

The importance of noncoding RNA is an exciting and emerging field in gene regulation. Long noncoding (lnc) RNAs are >200 nt in length and have distinct structural and spatial features which allow it to bind to DNA, RNA or protein partners. LncRNAs are important orchestrators of essential biological networks and are implicated in regulation of genes in cell growth and apoptosis, epigenetic regulation, transcription and translation, splicing and are linked to human diseases. Multiple lines of evidence pointed to the role of insulin signaling in the onset of sAD.

Figure 8:
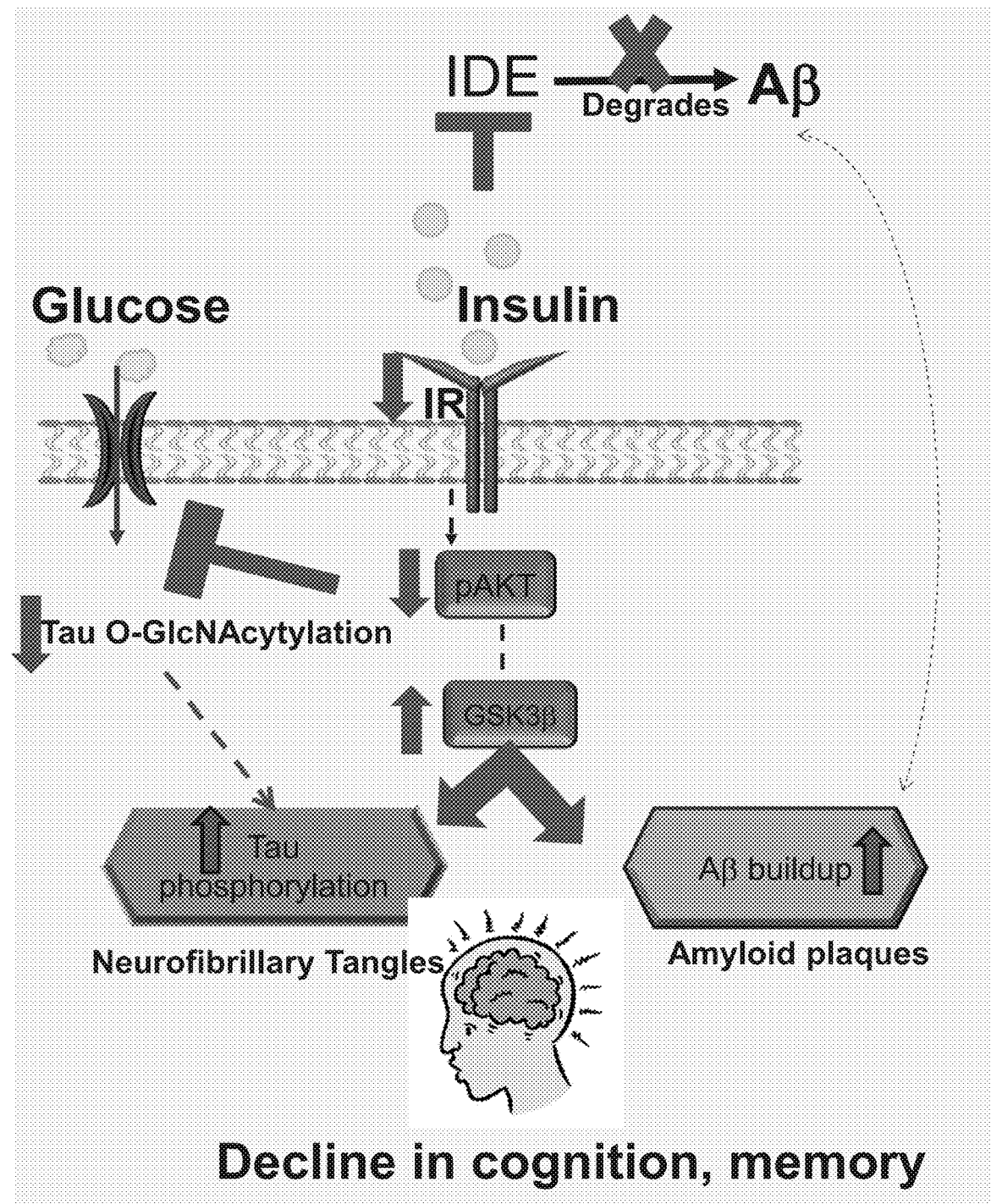
FIG. 8. shows a schematic of insulin receptor signaling. The arrows and lines indicate events that occur when insulin receptor levels decrease.

As shown in FIG. 8, decreased IR expression leads to decrease in PI3K→AKT which affects two crucial pathways: (1) decreases glucose transporters GLUT 1/3 thereby reducing glucose uptake and (2) decreases the phosphorylation of GSK3β which leads to its hyperactivation. This increased activity of GSK3β increases phosphorylation of tau culminating in neurofibrillary tangles as well as accumulation of amyloid-β (Aβ) peptides which form plaques. Furthermore, decreased glucose intake in the brain decreases Tau O-GlcNAcylation which also promotes hyperphosphorylation of tau. Separately, since insulin is not efficiently taken up due to decreased IR expression, excess extracellular insulin inhibits insulin degrading enzyme (IDE). IDE also functions to degrade Aβ and inhibition of IDE results in further accumulation of Aβ. Separately, in events leading to decreased insulin signaling via its receptors, Aβ oligomers activate TNFα/JNK pathway to phosphorylate IRS1 which leads to further inhibition of physiological phosphorylation of IRS1. These events taken together finally culminate in the clinical diagnosis of AD with decreased cognition and neuronal function as its hallmarks.

Figure 2:
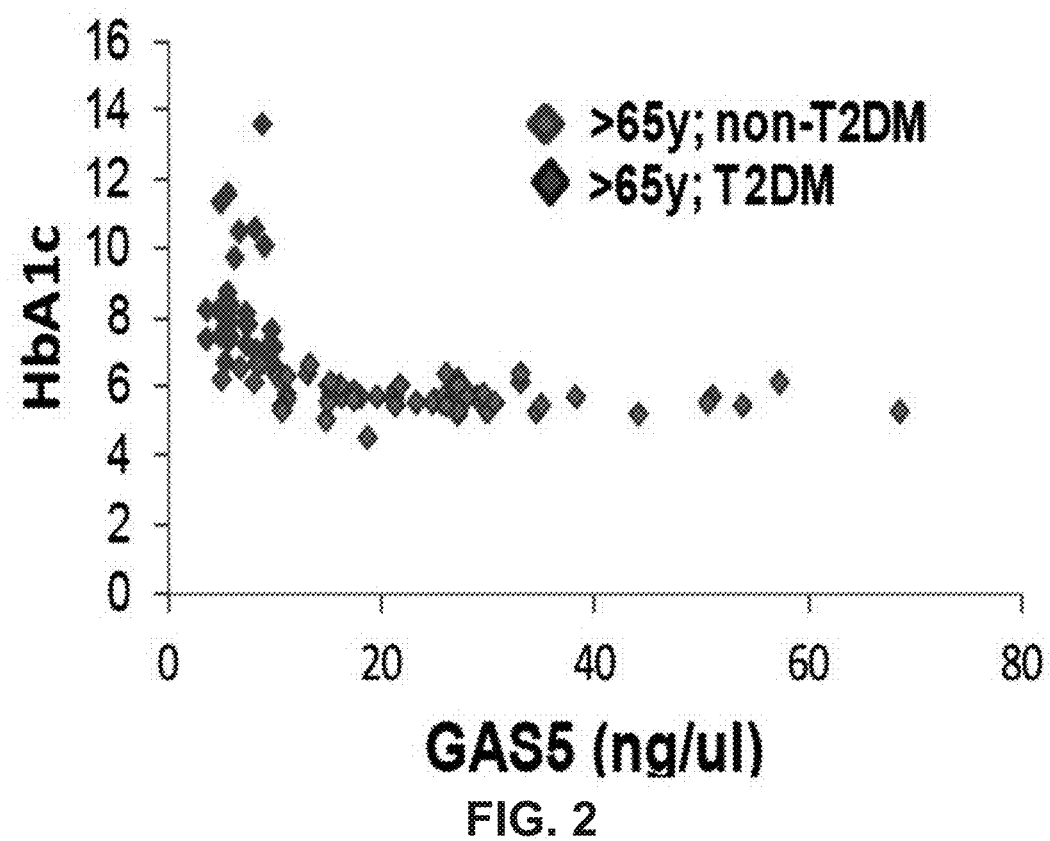
FIG. 2 shows a graph demonstrating the results from a SYBR Green absolute qPCR analysis of GAS5.

In this Example a transcriptomics approach was used to screen lncRNA levels in older patients (ages >65 years; total 96 patients) compared to younger (<45 y) patients (n=45). 47 of the older patients had type 2 diabetes mellitus (T2DM). These cohorts of patients had no forms of cancer (IRB #Pro00015802, serum from the research biospecimen repository (RBR) at the JAH VA Hospital). Total RNA was isolated using RNABee LS (specific formulation for isolating RNA from liquids and serum) and repeated using MagnaLA automated RNA isolation system (Roche). 1 μg of RNA was used to generate the cDNA using Superscript and screen with human LncProfiler (SABiosciences) array comprising of 84 lncRNAs with rigorous controls. Amongst the consistently detected lncRNAs across all samples, except for GAS5, other lncRNAs did not change significantly[27]. The levels of GAS5 in younger patients (<45 years) compared to older (>65 y) was determined. Our results show that older (>65 y) patients had a marked decrease in GAS5 expression compared to younger patients (no cancer, no T2DM) (FIG. 1). Comparing over 65 y T2DM to young, the T2DM patients had GAS5 levels less than 10 ng/μl (FIG. 2, HbA1c>6.5 is diabetic) indicating that lower GAS5 levels are correlated to increasing age and insulin resistance.

The lncRNA growth-arrest specific transcript 5 (GAS5) is a 5'-terminal oligopyrimidine class of gene shown to regulate cell growth, proliferation and survival. The biogenesis of GAS5 is established. GAS5 gene transcribes several snoRNAs as well as four splice variants of GAS5 mRNA. However, due to presence of STOP codon, none of the transcripts are transcribed into protein and degrade via the nonsense-mediated decay (NMD) pathway when translation is initiated. The RNA levels of GAS5 are regulated by its degradation instead of regulation at its transcriptional level. GAS5 is encoded at 1q25, a locus displaying abnormalities in a number of cancers and associated with retinopathy and CHD. It is down-regulated in breast cancer. GAS5 acts as a riborepressor by repressing transcription of glucocorticoid receptor. GAS5 levels are decreased in the hippocampus of rats with cognitive decline and is associated with the aging brain. However, the role of lncRNAs affecting insulin resistance and specifically the role of lncRNA GAS5 in Alzheimer's disease is unknown.

Figure 3A:
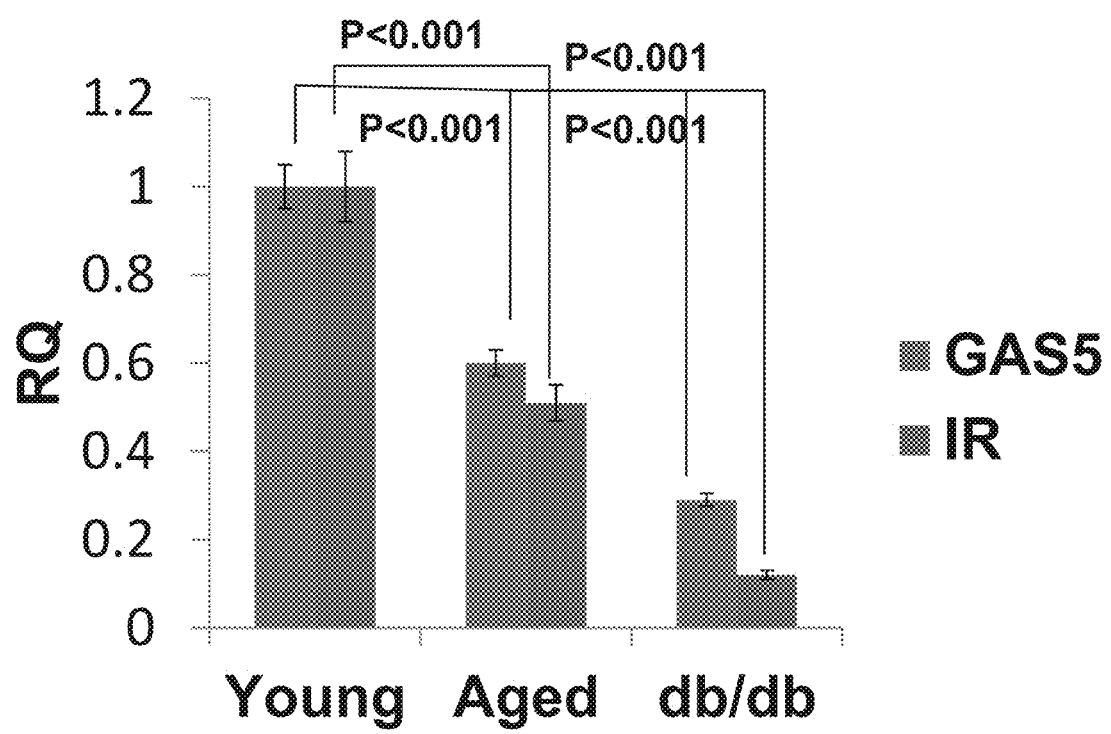
FIGS. 3A-3C show graphs demonstrating the results from a SYBR Green absolute qPCR analysis of GAS5 in various samples (FIG. 3A) and the RAWM post intranasal insulin treatment in aged normal and db/db mice (N=8 in each group) (FIGS. 3B and 3C).

Diabetes increases the risk for impaired cognitive function and dementia by 47%. Patients with T2DM have cognitive deficits affecting verbal and nonverbal memory, attention, information processing speed, and executive function. To assess the cognitive function with respect to insulin resistance in vivo, aged diabetic mice BKS.Cg-+ Lepr$^{db}$/+ Lepr$^{db}$/OlaHsd (Older db/db mice from Harlan were used; 11 months—as this mouse model has lower life span) along with their normal age-matched controls. We measured the levels of GAS5 and insulin receptor (IR) in young (4 months) and db/db mice along with their age-matched control mice. The hippocampi of the mice were collected and SYBR Green qPCR was performed. Results indicated that GAS5 and IR levels were lower in aged or aged, diabetic mice than in younger mice (FIG. 3A). Intranasal insulin delivery is a noninvasive method that bypasses the blood-brain barrier and delivers insulin to the brain and the spinal cord. Biologically effective concentrations of insulin can be achieved without systemic side effects.

Figure 3B:
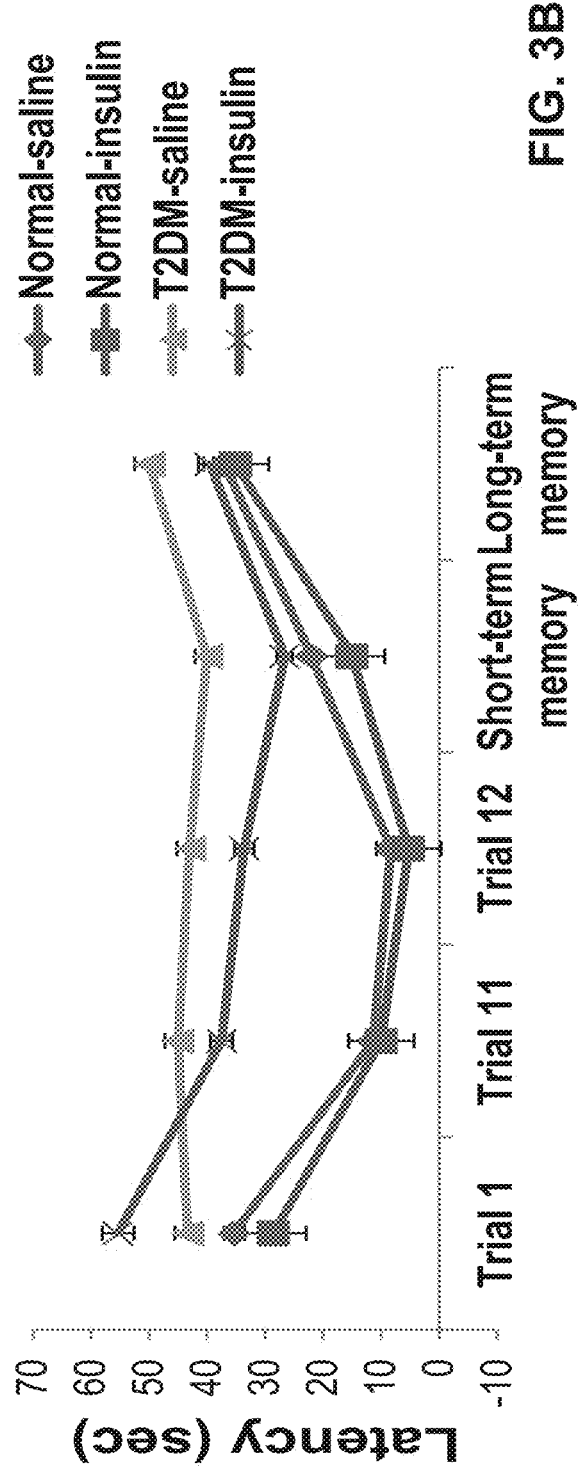
Figure 3C:
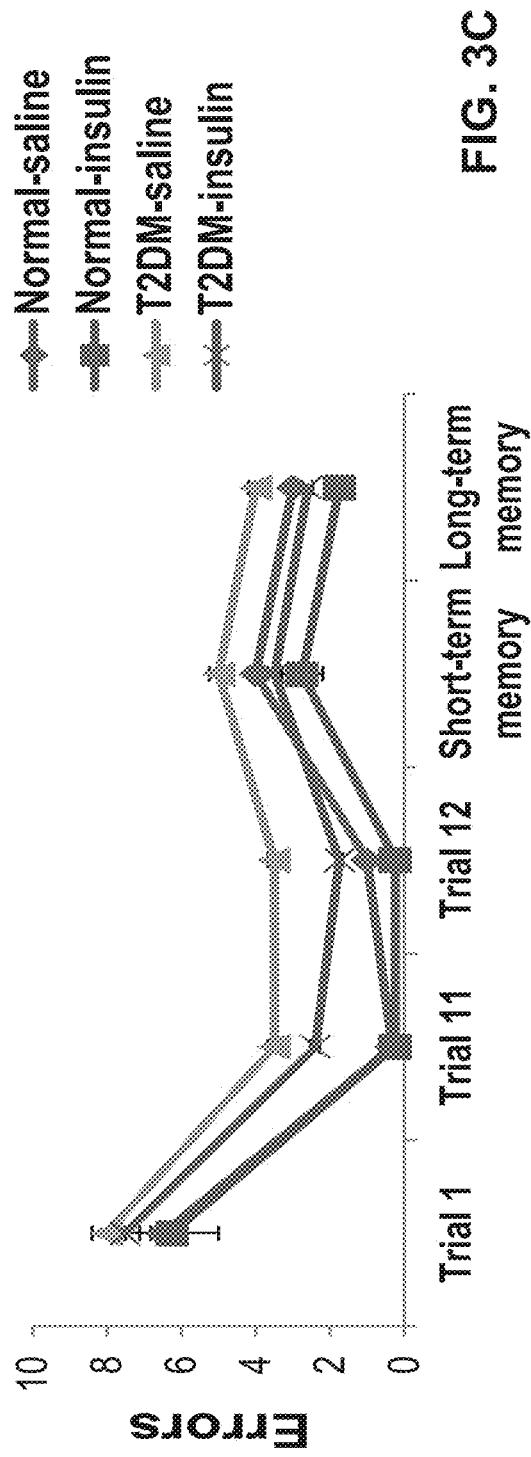
Figure 4A:
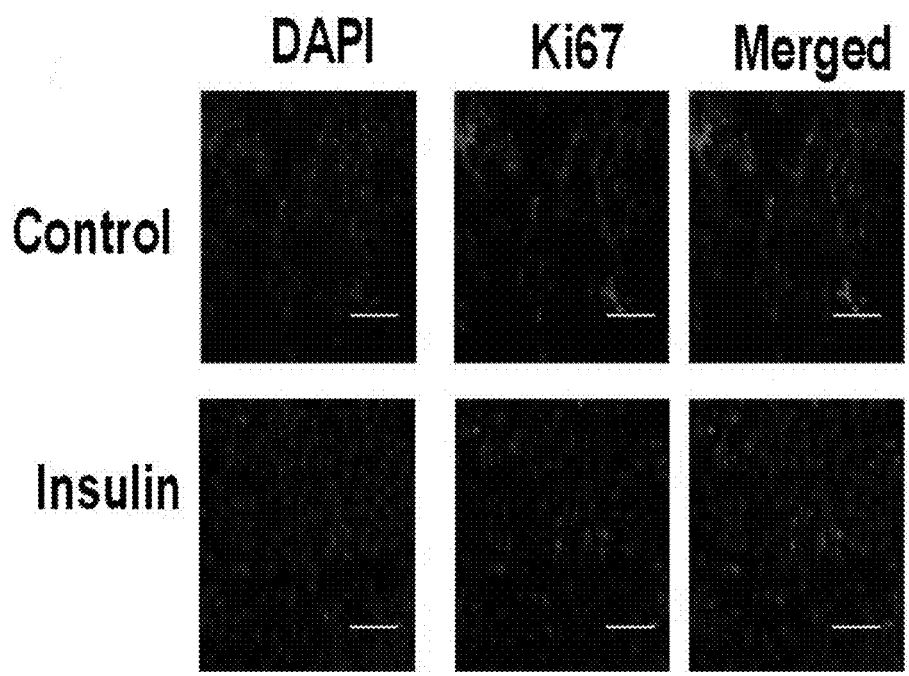
FIGS. 4A-4B show panels fluorescent microscopic images of the results from Immuno histochemical analysis post insulin treatment in neron cells. The bar in the images of the panel of FIG. 4B is 20 μm.
Figure 4B:
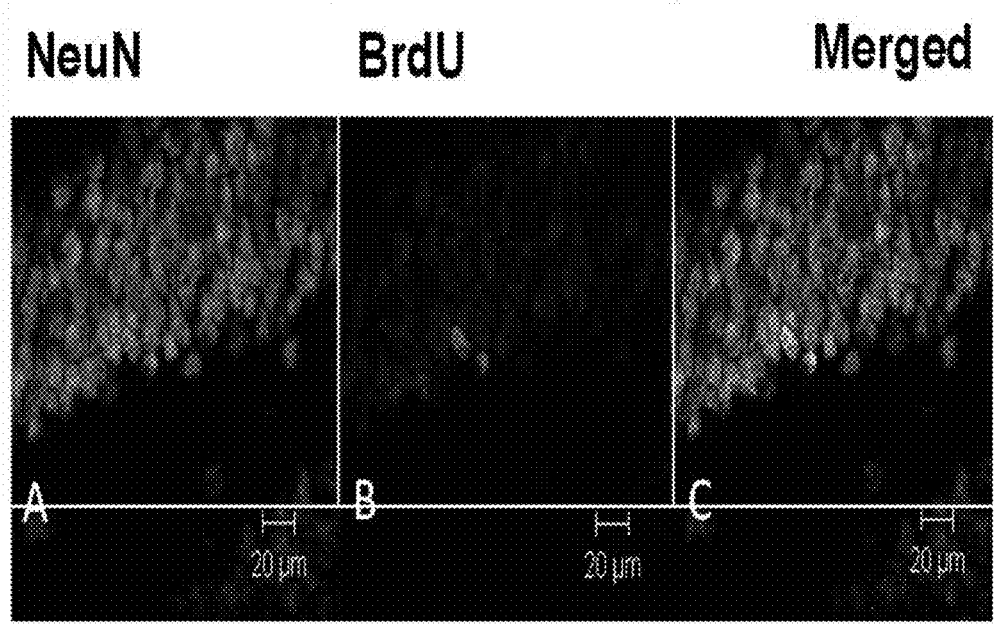

After intranasal administration, insulin and peptide analogues begin to accumulate in the CSF within 30 minutes. Intranasal insulin directly improves learning and memory and has no effect on circulating blood glucose levels. Thus, the effects may reflect activation of neuronal insulin signaling pathways. The age-matched control and db/db mice cohorts were treated with intranasal insulin (1 unit/ml, daily for 3 weeks) and the radial arm water maze (RAWM) was used for cognitive assessment. Errors (incorrect arm choices) and escape latency were recorded for each daily trial (FIGS. 3B-3C). The aged diabetic mice had a marked decline in memory and cognition, as compared to aged non-diabetic mice. Administration of intranasal insulin improved the cognitive performance of both normal aged and aged diabetic mice. Insulin treatment did not increase the levels of IR but using immunohistochemistry, our results show that insulin treatment increased neuronal proliferation (FIG. 4A) and neurogenesis (FIG. 4B).

Figure 5:
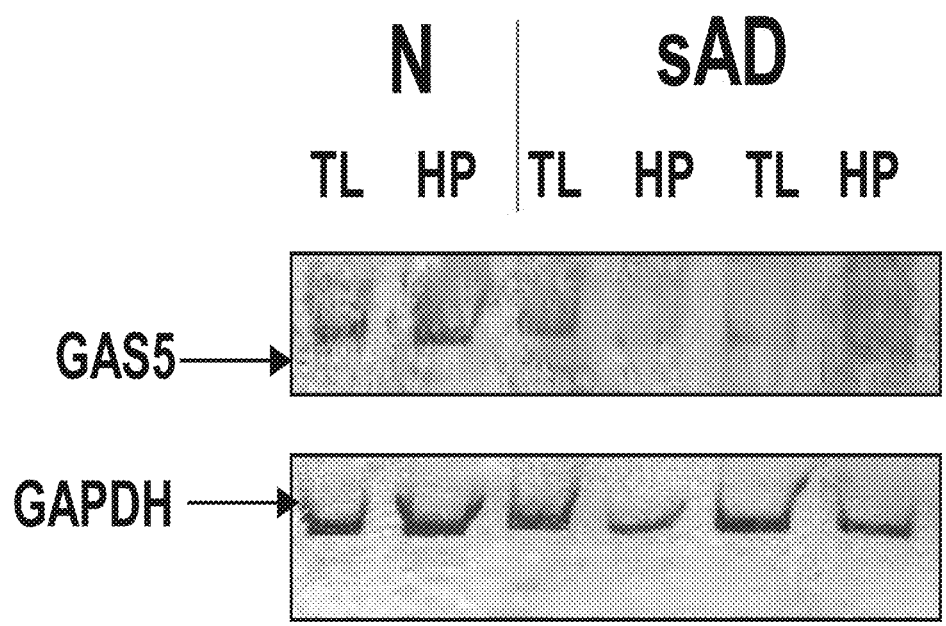
FIG. 5 shows an image of a representative silver stained PCR gel of AD brain samples. The assay was performed in triplicate.
Figure 6:
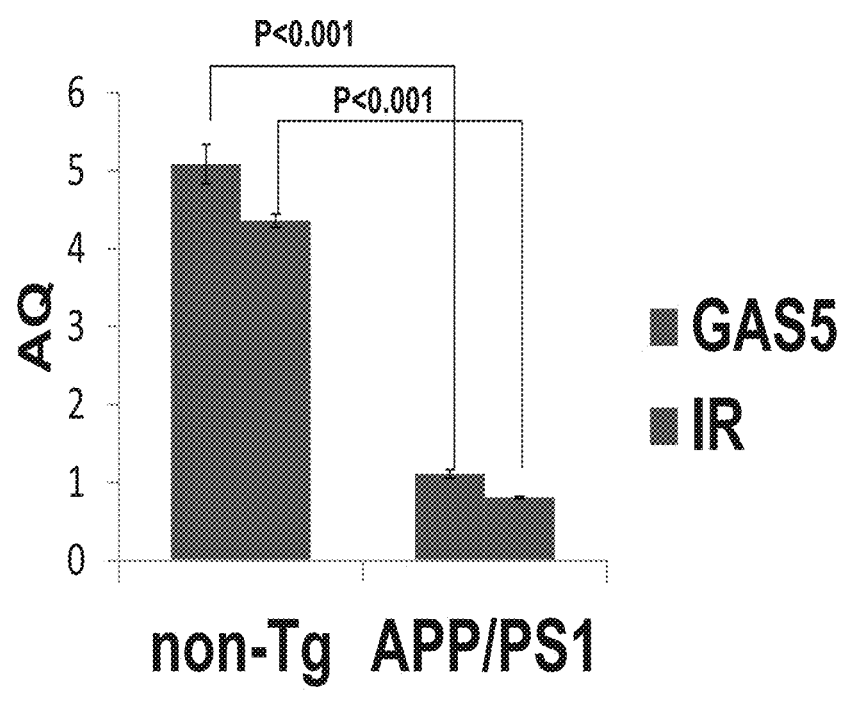
FIG. 6 shows a graph demonstrating the results of a SYBR Green absolute qPCR analysis of GAS5 and IR in various samples. n=8.

To assess the levels of GAS5 in Alzheimer's disease, human brain samples (from temporal lobe (TL) and hippocampus (HP)) from sAD patients or matched normal were analyzed. Results show decreased GAS5 levels in sAD brain (FIG. 5). Next, cerebral cortex from 20 month transgenic APPswe/PS1dE9 mice were analyzed as this mouse model shows amyloid deposition and neuropathology seen in Alzheimer's disease. The age-matched non-transgenic littermates served as control (n=8 in each cohort). Using SYBR Green absolute qPCR (run in triplicate with standard curve), the results show a dramatic decrease in GAS5 and IR levels in APP/PS1 mice, $p<0.001$ highly significant unpaired Student's t-test significant unpaired Student's t-test (FIG. 6).

Figure 7A:
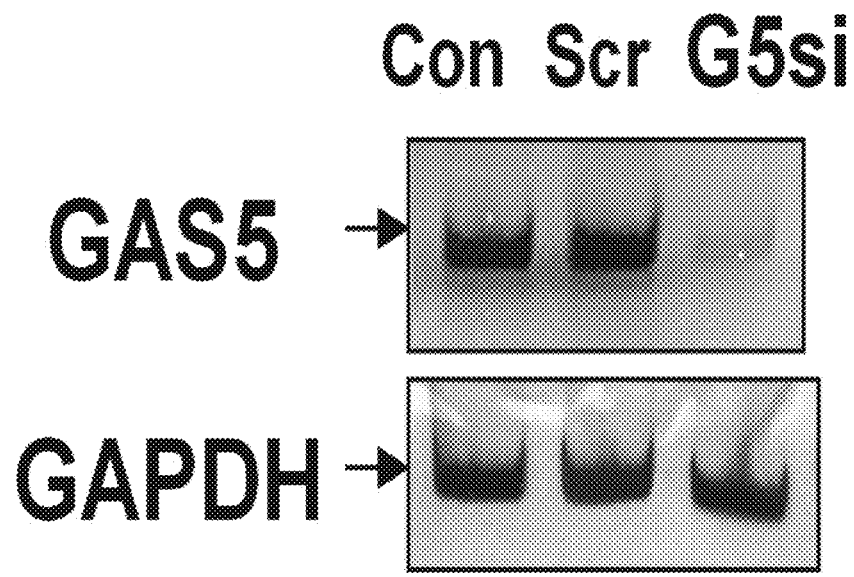
FIGS. 7A-7D show images of representative silver stained PCR gel of GAS5 siRNA depleted NC (Scr=scrambled siRNA) (FIG. 7A), western blot anlaysis using phosphor-tau cocktail anitbodies (Ab)(FIG. 7C), and immunoblot demonstrating GLUT3 translocation post insulin treatment, and a graph (FIG. 7B) demonstrating the results of a glucose uptake assay.
Figure 7B:
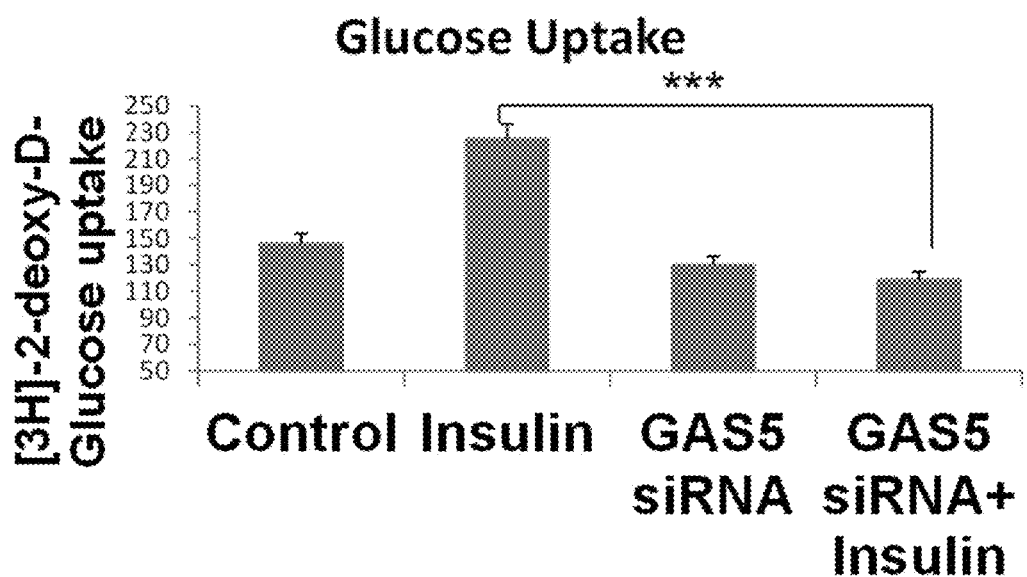
Figure 7C:
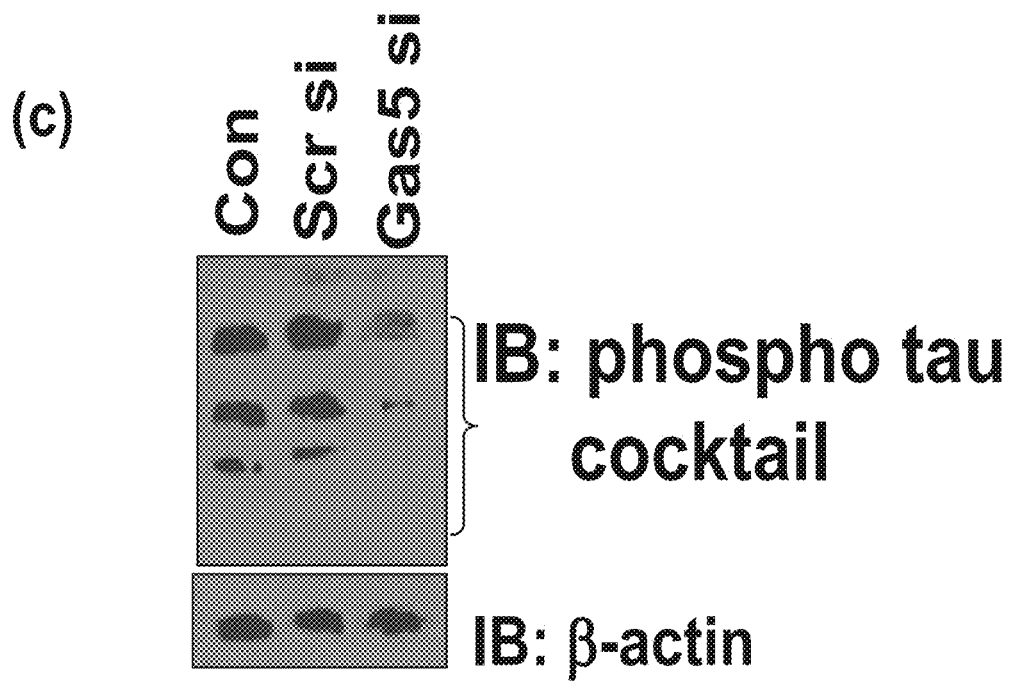

The hippocampus is important for memory and cognition. Hence, primary neuronal cells (NC) derived from adult mouse hippocampus were established in culture. These experiments were also repeated with HT22 and SH-SY5Y cell lines with similar results. GAS5 siRNA (10 nM, Ambion 332778, validated; scrambled siRNA as control) was transfected in NC (Nucelofector, Amaxa program A-023) for 48 h and knockdown confirmed by GAS5 PCR using primers for GAS5 and product separated on PAGE, silver stained for visualization (FIG. 7A). We determined the effect of GAS5 depletion on glucose uptake in NC. Glucose uptake assay was performed. Cells were serum starved, 10 nM insulin was added to cells for 30 minutes and [$^3$H]-deoxy-2-D-Glucose uptake was measured. Results (FIG. 7B) indicated a decrease in glucose uptake in GAS5 depleted NC (***$p<0.001$, highly significant using two-tailed students t-test). These results indicate that GAS5 levels influence glucose uptake. Separately, cell lysates were collected for western blot analysis. The results show decreased tau phosphorylation with depletion of GAS5 (FIG. 7C).

Figure 7D:
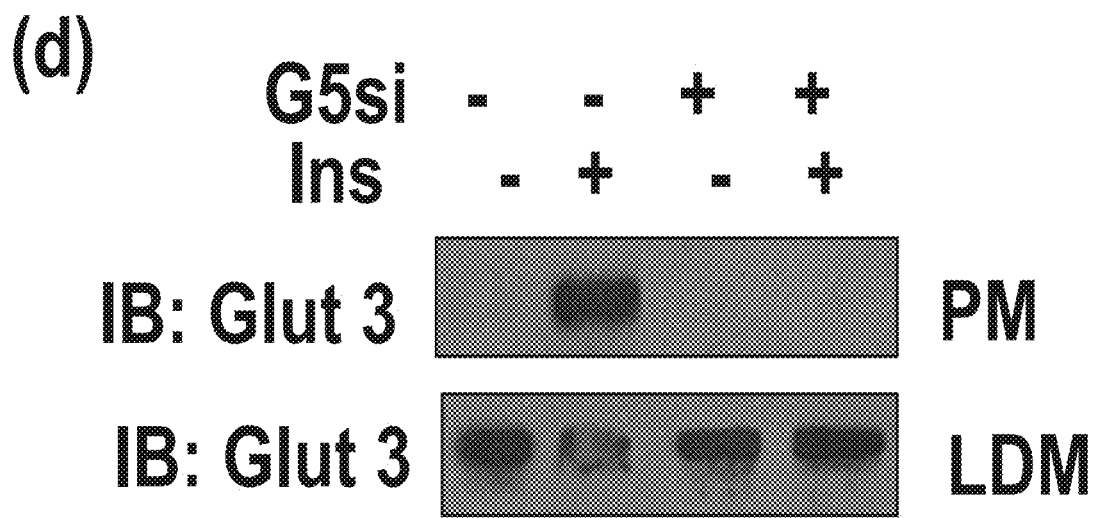

In the neurons, the primary glucose transporter is GLUT3 (with lower expression of GLUT1,2,4,5 and 8). Hence, subcellular fractionation was performed to determine translocation of Glut3 to plasma membrane in GAS5siRNA treated NC. The results (FIG. 7D) show depletion of GAS5 inhibited insulin mediated GLUT3 translocation.

Since the data showed that GAS5 depletion decreased glucose uptake, we evaluated the genes involved in glucose metabolism that may be affected by depletion of GAS5. Customized human glucose metabolism array (Qiagen) was used to screen for expression of 84 genes related to the glucose metabolism and insulin resistance. NC were depleted using GAS5 siRNA as above. The array results showed that GAS5 depletion resulted in dramatic inhibition of insulin receptor (IR). These results were individually verified using SYBR Green qPCR (FIG. 9, NC— control set as reference in calculating RQ in qPCR; $p<0.001$ highly significant using two-tailed Student's t-test).

LncRNAs have structural and spatial features which allow it to bind to DNA, RNA or protein partners thereby regulating transcription of genes. Since our data showed GAS5 depletion significantly inhibited insulin receptor IR (IR-A predominantly expressed in the brain), we hypothesized that GAS5 may regulate transcription of IR and not alternative splicing or other post-transcriptional mechanism. Hence, we performed a computational analysis (LaserGene™ program) to determine whether GAS5 may bind to the promoter region of IR. The analysis showed that the sequence "aacgtttttat" on IR promoter region (at −826 bp) is 100% complementary to a sequence on GAS5 DNA binding domain.

Figures 10A, 10B:
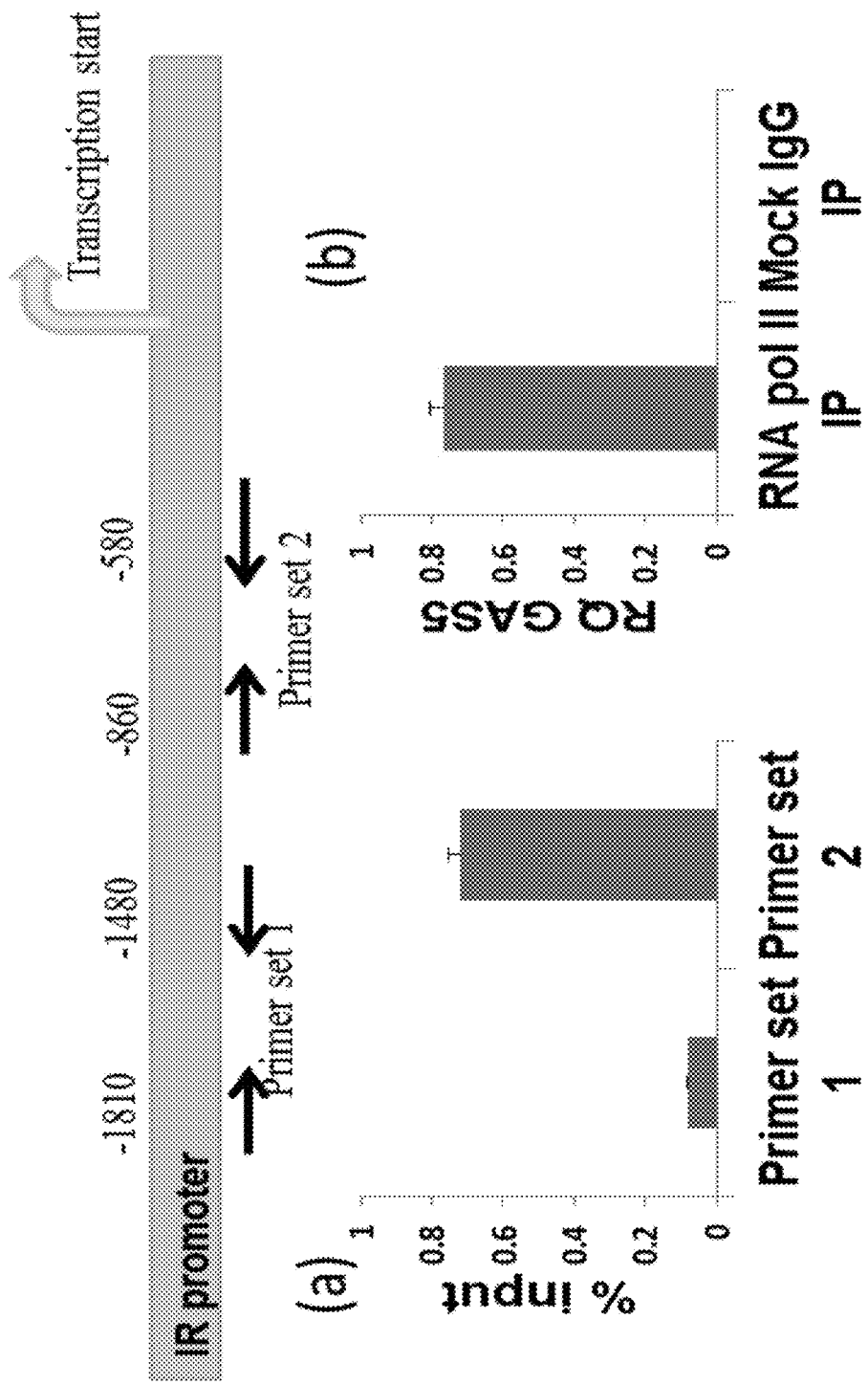
FIGS. 10A and 10B show the results from a ChRIP assay.

It was next investigated whether GAS5 could bind to IR promoter and sequester RNA polymerase II for transcription initiation. The Chromatin-RNA immunoprecipitation (Ch-RIP) assay was performed in NC. Following chromatin fixation, immunoprecipitations performed with anti-RNA polymerase II (IgG IP serves as control). (i) Immunoprecipitated DNA was analyzed by semi-quantitative PCR using primers amplifying two regions on the IR promoter: −580 to −860 bp; −1480 to −1810 bp. These regions were assessed as putative GAS5 binding regions based on computational analysis for complementary sequence. Input DNA (1:10 of released chromatin) was included in PCRs. (ii) the cross linking was reversed, RNA was isolated from the immunoprecipitated complex and GAS5 was detected using qPCR. These results (FIGS. 10A-10B) indicate that GAS5 binds to the IR promoter between −580 to −860 bp simultaneously in a complex with RNA polymerase II. The data can indicate that GAS5 acts as a riboactivator and promotes transcription of insulin receptor (IR).

Example 2

Multiple defects in insulin signaling including insulin receptor (IR) number and insulin receptor kinase activity contribute to insulin resistance in the brain. Given that glucose uptake may be mediated via insulin-independent pathways too, this Example examines the effect of GAS5 on relevant metabolic pathways in the brain.

The mammalian target of rapamycin (mTOR) is a serine/threonine protein kinase. mTOR which is a cytoplasmic kinase known to regulate cell growth and metabolism in response to inter-cellular signals such as insulin, cytokines, IGF-I, TNF and VEGF, has been correlated with an increased risk of insulin resistance. mTOR signaling plays a central role in the aging brain. mTOR is central to two large multi-protein complexes mTOR complex 1 and 2 (mTORC1 and mTORC2). mTORC1 mediated activation of S6 kinase (S6K), subsequently causes phosphorylation and degradation of insulin receptor substrates 1 and 2. On the other hand, mTORC2 activation results in increased AKT mediated glucose transporter translocation into the cellular membrane. Sirt-1 (Silent information regulator factor 2-related enzyme 1) is a nicotinamide adenine dinucleotide-dependent class III histone deacetylase that is involved in an array of functions such as cell longevity, genomic stability and gene silencing. Sirt-1 has been shown to inhibit the function of mTORC1 by an upstream activation of the TSC1/TSC2 complex that further inhibits Rheb, an activator of mTORC1. Furthermore, the downregulation of sirt-1 results in downregulation of the mTORC2 complex since it controls the expression of Rictor, a component of the mTORC2 complex, by interacting with NRF1 on the NRF1-binding sites of Rictor promotor region.

Figure 11A:
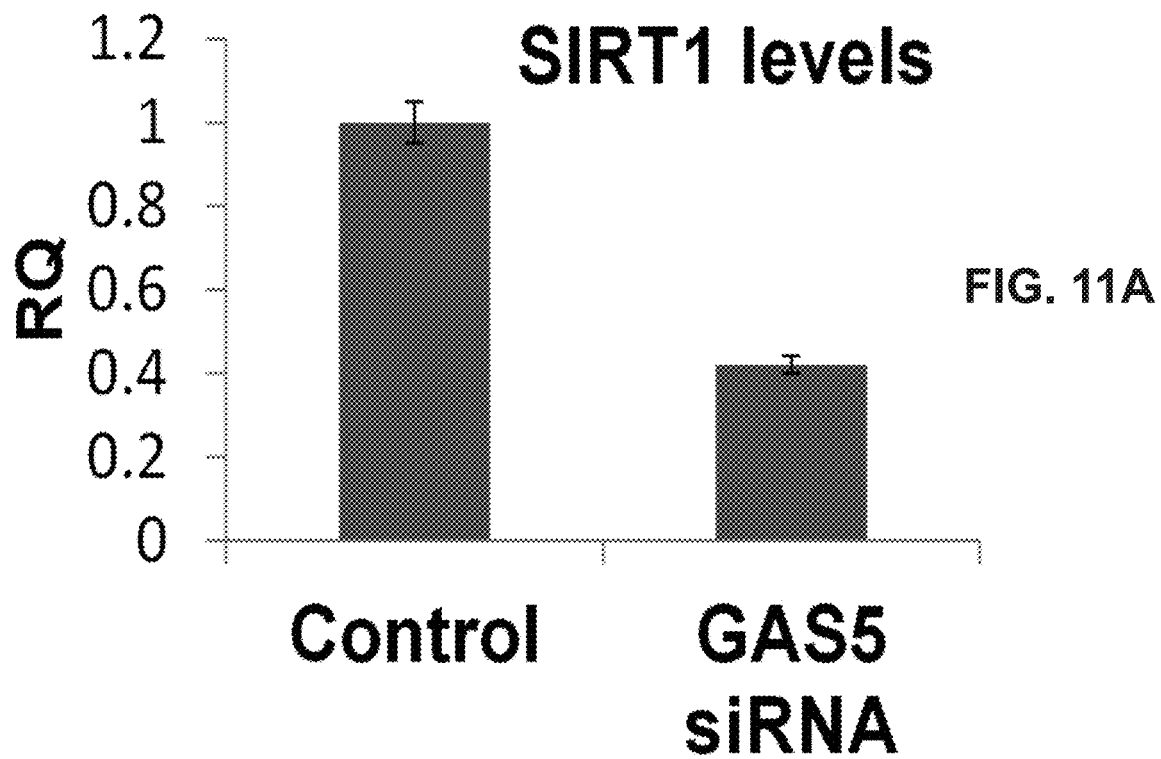
FIGS. 11A-11B show the results of a SYBR Green qPCR analysis of SIRT1 in GAS5 depleted cells (FIG. 11A) and an image of a representative immunoblot with mTOR and Rictor following immuno-precipitation (FIG. 11B). Experiment results were repeated thrice with similar results.
Figure 11B:
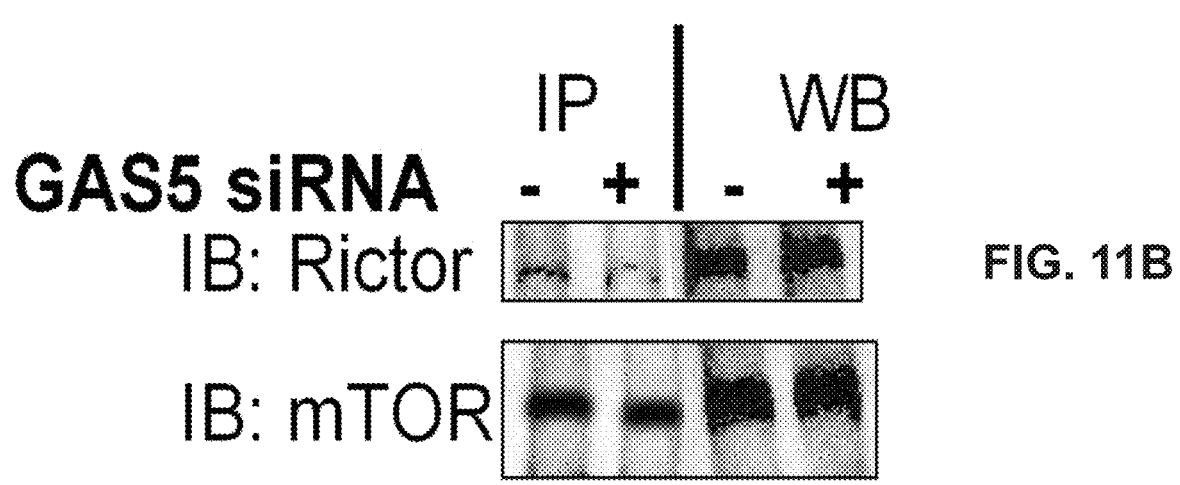

SIRT1 mediates mTOR signaling in glucose metabolism and is decreased in insulin resistant state. Hence, the levels of SIRT1 upon GAS5 depletion was evaluated. GAS5 siRNA was transfected (as described above) in NC and SYBR Green qPCR was used to evaluate SIRT1 levels. The results show decrease in SIRT1 in GAS5 depleted NC (FIG. 11A). Separately, cell lysates were immunoprecipitated with mTOR and immunoblotted with Rictor (component of mTORC2). The results show decreased association of mTOR with Rictor in GAS5 depleted NC (FIG. 11B). Similar results obtained with HT22 and SHSY5Y cell lines.

Example 3

Figure 12:
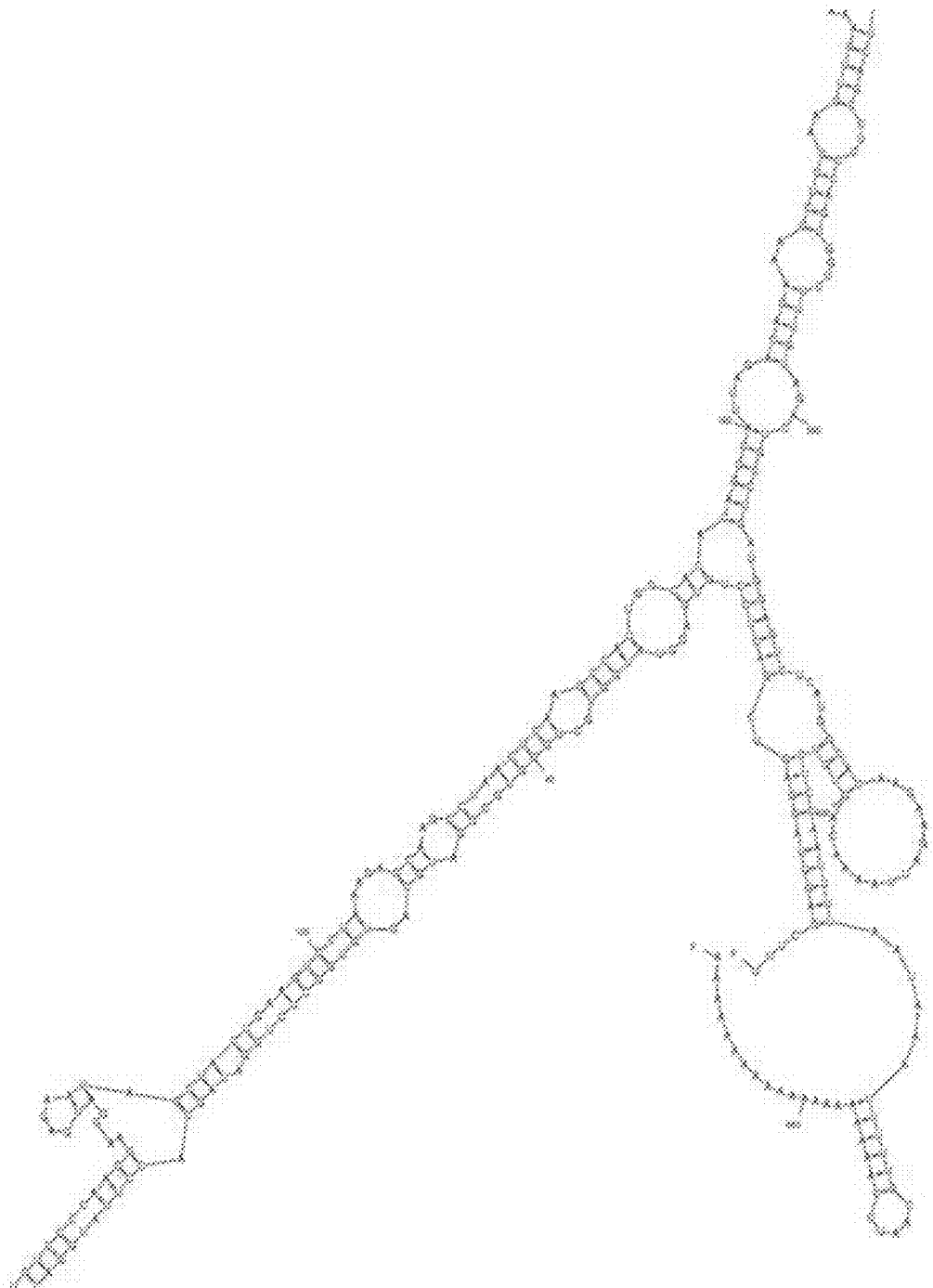
FIG. 12 shows the secondary structure of GAS 5 lncRNA according to SEQ ID NO: 1.

RNA folds and has secondary structures. Usually the stem-loop structures recruit & bind to proteins. The TAA is part of stem-loop structure that can be involved in recruiting proteins and allow for nonsense mediated decay. This Example can at least demonstrate the design of a compound that can bind to this region and block its turnover. This can increase GAS5 levels in diseases such as diabetes. The secondary structure of GAS5 is demonstrated in FIG. 12.

Strategy for compound design: GAS5 transcript may be targeted to faster turnover by nonsense mediated RNA decay. GAS5 transcript has a premature termination codon which renders greater susceptibility for nonsense mediated RNA decay. It was demonstrated that GAS5 levels were increased when UPF1, an essential component of nonsense mediated RNA decay, was depleted (Tani, H., Torimura, M., and Akimitsu, N. (2013) The RNA degradation pathway regulates the function of GAS5 a non-coding RNA in mammalian cells. *PloS One* 2013; 8(1):e55684. doi: 10.1371/journal.pone.0055684). This demonstrated an inverse relationship of UPF1 and GAS5. Amongst known UPF1 targets are genes associated with diabetes (COIL, ITPR3, TRIM32) which were upregulated when UPF1 was depleted (Tani, H., Imamachi, N., Salam, K. A., Mizutani, R., Ijiri, K., Irie, T., Yada, T., Suzuki, Y., and Akimitsu, N. (2012) Identification of hundreds of novel UPF1 target transcripts by direct determination of whole transcriptome stability. *RNA biology* 9, 1370-1379). GAS5 and UPF1 levels were measured in NDM and DM adipocytes. The data indicated that GAS5 levels were low in DM adipocytes concurrent with increased expression of UPF1 compared to NDM adipocytes (FIG. 3A).

The results using AHD-058-6 showed that inhibiting UPF1 in DM increased GAS5 levels (not shown due to page constraints). However, it is not advisable to inhibit UPF1 since it is integral to nonsense mediated decay, which is an important surveillance mechanism to reduce errors in gene expression. Additionally in humans, UPF1 is used for S phase progression and genome stability (Azzalin C M, Lingner J. The human RNA surveillance factor UPF1 is important for S phase progression and genome stability. Curr Biol. 2006; 16(4):433-9. doi: 10.1016/j.cub.2006.01.018. PubMed PMID: 16488880 and Azzalin CM. UPF1: a leader at the end of chromosomes. Nucleus. 2012; 3(1):16-21. PubMed PMID: 22156744.) A strategy was designed to disrupt the binding of UPF1 to GAS5 thereby inhibiting GAS5 turnover. GAS5 has premature stop codons UAA upstream of the poly(A) tail. UPF1 binds to this region and tags it for nonsense mediated decay (Tani H, Torimura M, Akimitsu N. The RNA degradation pathway regulates the function of GAS5 a non-coding RNA in mammalian cells. PloS one. 2013; 8(1):e55684. Epub 2013/02/06. doi: 10.1371/journal.pone.0055684. PubMed PMID: 23383264; PubMed Central PMCID: PMC3559549).

Figure 13:
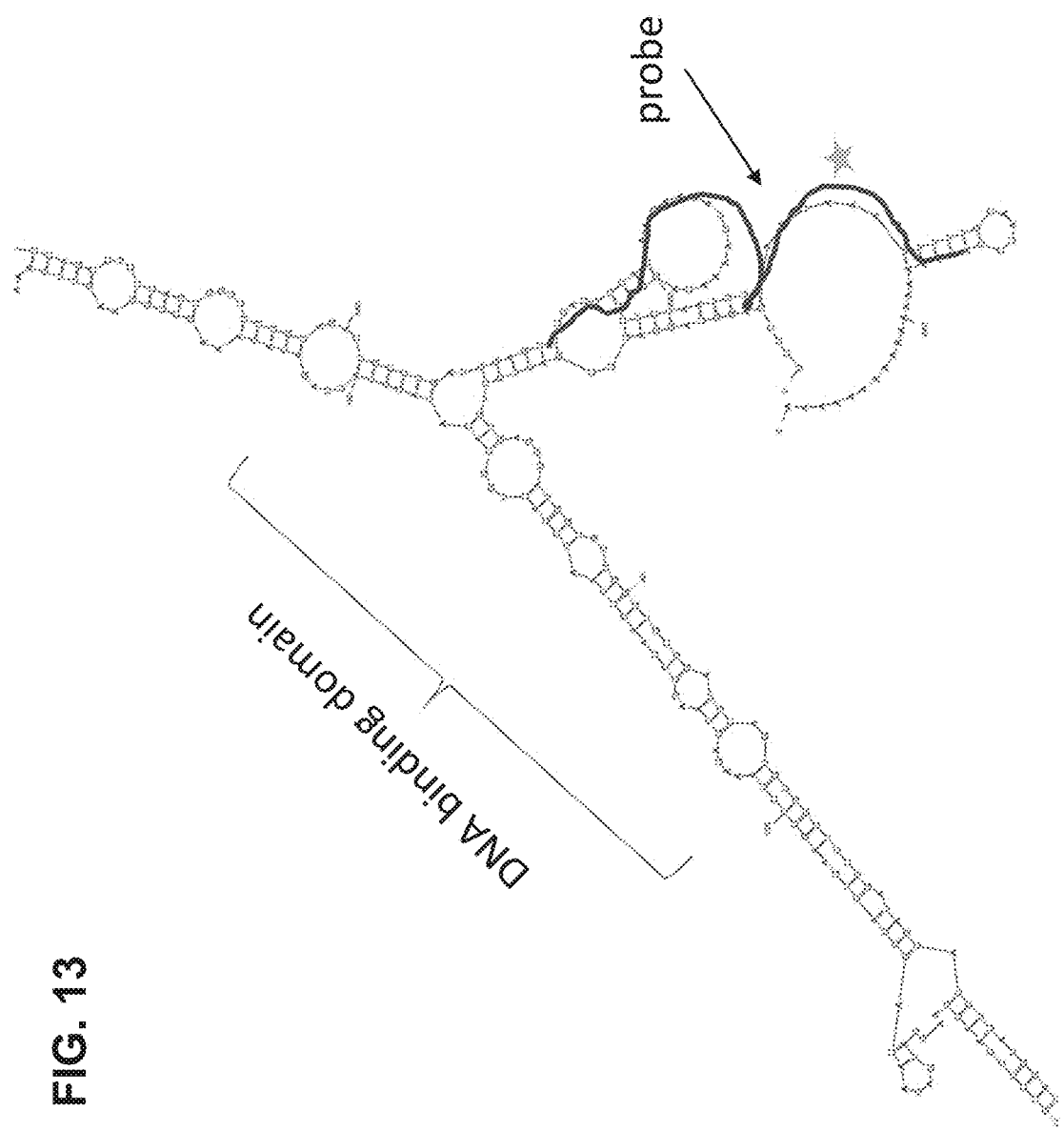
FIG. 13 shows the secondary structure of GAS 5 lncRNA and relevant protein and DNA binding site(s) and binding of a GAS5 lncRNA fluorescently labeled probe.

The interaction between UPF1 and GAS5 was disrupted using a γ-AApeptide based one-bead-one-compound (OBOC) combinatorial library (Wu H, Li Y, Bai G, Niu Y, Qiao Q, Tipton J D, Cao C, Cai J. gamma-AApeptide-based small-molecule ligands that inhibit Abeta aggregation. Chemical communications. 2014; 50(40):5206-8. doi: 10.1039/c3cc46685j. PubMed PMID: 24158240). The γ-AApeptide is a peptidomimetic with side chains for chemical diversity and are resistant to proteolytic cleavage. To screen the compound library, a probe that contained a fluorescein tagged oligonucleotide was synthesized. The probe spanned 30 nucleotides on either side of the UAA sequences on GAS5 (FIG. 13) The fluorescein was attached to the 5'end (beginning of oligonucleotide probe sequence). The nucleotide sequence within the GAS5 lncRNA that the oligonucleotide probe binds to can be about 100% identical to CTCCCAGTGGTCTTTGTAGACTGCCTGATG-GAGTCTCATGGCACAAGAAGAT<u>TAA</u>AACAGT GTCTCCAATTT <u>TAATAAA</u>TTTTTGCAATCCAAAAAAAAAAAAAAA AAAAA (SEQ ID NO: 4), which is nucleotides 541 to 651 of SEQ ID NO: 1. The underlined regions indicate the UAA that is the target regions. As such, the oligonucleotide probe was designed to flank both sides of these target regions.

This is at the 3' end of the transcript (near poly(A) tail) and does not interfere with 5' DNA binding domain of GAS5, which interacts with the insulin receptor. The length of oligonucleotide was required to maintain stem loop structure to specifically bind to GAS5. Further, we modeled the oligonucleotide (RNAfold software) to evaluate its folding and verified absence of any unwanted secondary structures. The backbone was modified by 2'-MOE (2'-O-methoxyethylribose), which protects it from degradation and a fluoroscein tag was attached to the 5'end to aid in screening. The oligonucleotide probe was used to screen 160,000 molecules in the combinatorial library using tRNA as control (as tRNA has similar stem loop secondary structures). Four positive beads were identified which demonstrated the stringent conditions and high specificity of binding. These compounds were tested in vitro for their ability to disrupt binding of UPF1 to GAS5 thereby protecting it from turnover via nonsense mediated decay. Compounds have a structure according to Formula 3 (also referred to herein as G5-1397), derivatives thereof and Formula 14 were identified and validated as being able to bind GAS5. The compound having a structure according to Formula 3 was determined to have a chemical formula of $C_{68}H_{92}N_{10}O_9S$, a mass of about 1224.6769, and a molecular weight of 1225.6050. The compound having a structure according to Formula 14 was determined to have a chemical formula of $C_{63}H_{85}N_9O_{13}S$, a mass of about 1207.5988, and a molecular weight of 1208.4830.

Figure 14A:
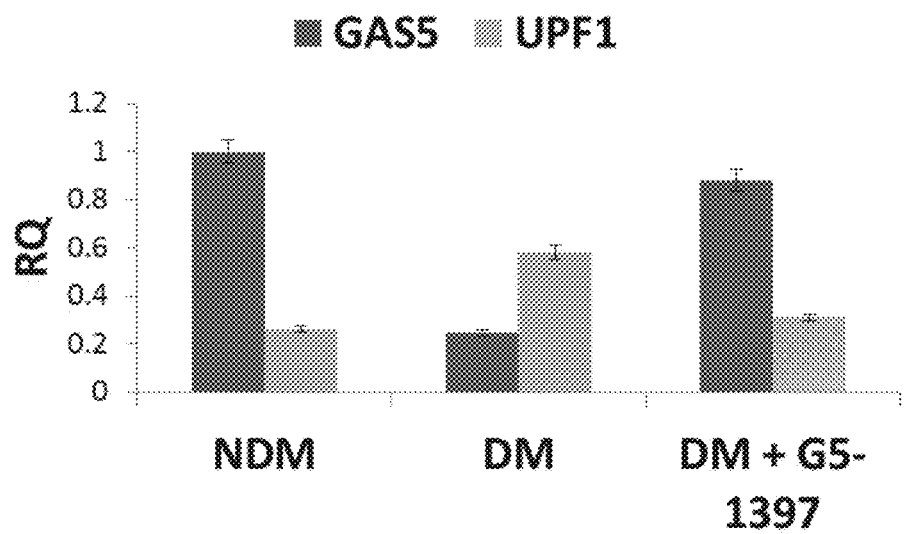
FIGS. 14A and 14B show graphs demonstrating the results from a qPCR of GAS5 and UPF1 (n=4) (FIG. 14A) and results from a cell viability assay after treatment with compound G5-1397 (also referred to herein as Formula 3) (FIG. 14B).
Figure 14B:
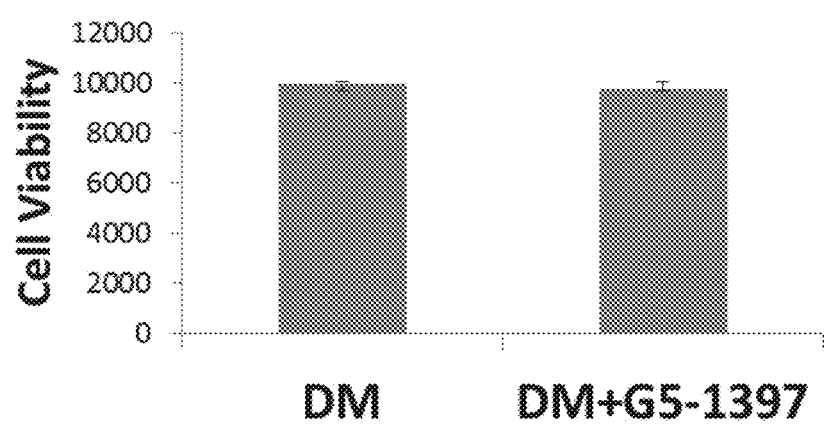

DM adipocytes were treated with G5-1397 (20 nM) for about 24 hours. GAS5 levels were measured using SYBR Green qPCR. The results show G5-1397 substantially increases GAS5 levels in DM adipocytes (FIGS. 14A-14B). Further, G5-1397 increased GAS5 without causing cell toxicity.

RNA-EMSA was performed as previously described (see e.g. Apostolatos, H., Apostolatos, A., Vickers, T., Watson, J.

E., Song, S., Vale, F., Cooper, D. R., Sanchez-Ramos, J., and Patel, N. A. (2010) Vitamin A metabolite, all-trans-retinoic acid, mediates alternative splicing of protein kinase C deltaVIII (PKCdeltaVIII) isoform via splicing factor SC35. *J Biol Chem* 285, 25987-25995 and Patel, R. S., Carter, G., Cooper, D. R., Apostolatos, H., and Patel, N. A. (2014) Transformer 2beta homolog (*Drosophila*) (TRA2B) regulates protein kinase C deltaI (PKCdeltaI) splice variant expression during 3T3L1 preadipocyte cell cycle. *J Biol Chem* 289, 31662-31672

Figure 15:
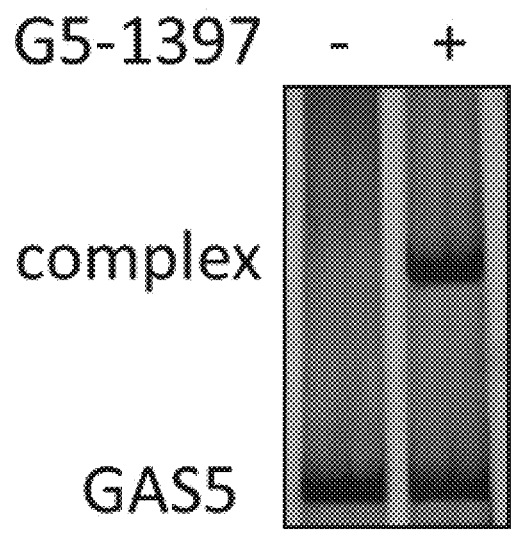
FIG. 15 shows an image of the results from an REMSA demonstrating GAS5 transcript binding to compound G5-1397 (also referred to herein as Formula 3) (n=3).

Briefly, GAS5 was cloned in TOPO vector which has the T7 promoter. In vitro transcription assay was performed with biotin-label using RiboScribe kit using T7 RNA polymerase at 37° C. for 2 h in the presence of nucleotides, RNase inhibitor, and 5× transcription buffer. 0.1 nM of transcribed, biotin-labeled GAS5 was incubated with 10 nM G5-1397 in presence of 10U yeast tRNA and 10 units of RNase inhibitor in a final volume of 10 µl of RNA shift buffer for 20 min at room temperature and detected using Biotin Chromogenic Detection kit (ThermoFisher). The results with RNA-EMSA demonstrate that G5-1397 bound to GAS5 transcript (FIG. 15). Using the same assay, compounds according to Formulas 4, 6-19 were also observed to bind GAS5 long non-coding RNA.

Example 4

Introduction. The number of Americans living with Alzheimer's disease (AD) is escalating rapidly with an increase in aging population. In 2016, 5.4 million people have AD and this number is expected to triple by 2050 (Alzheimer's Association). AD costs the nation $236 billion and is expected to reach 1 trillion by 2050. AD is the most common form of dementia seen in the elderly population. 5% AD patients have early onset AD with genetic mutations (onset age <60 y) while 90-95% AD cases are sporadic, late-onset AD (sAD). The major risk factors contributing to sAD are aging, type 2 diabetes and ApoE4 alleles. In the last decade, extensive research revealed accumulation of AR plaques and neurofibrillary tangles as hallmarks of end stages of sAD. However, understanding the early metabolic and molecular pathways in the brain contributing to sAD are fundamental not only to elucidate sAD pathology but also to develop innovative therapy to halt the onset or progression of sAD.

It is becoming increasingly clear that noncoding transcripts such as long noncoding (lnc) RNAs play an integral part in manifestation of human diseases. GAS5 lncRNA were identified using a transcriptomics screen and can demonstrate that GAS5 it mediates tau phosphorylation and APP levels in neurons. Alterations in lncRNA mediating metabolic pathways not only affects neurofibrillary tangles and AR levels but also increases the oxidative stress and inflammation in neurons. GAS5 stabilizing compounds described herein can treat and/or prevent sAD pathology.

Results

As is also described elsewhere herein, a transcriptomics approach was used to screen lncRNA levels in older patients (ages >65 years; total of 96 patients) compared to younger (<45 years; total of 45 patients. See e.g. FIG. 1. 47 of the older patients had type 2 diabetes mellitus (T2DM). These cohorts of patients had no forms of cancer (IRB #Pro00015802, serum from the research biospecimen repository (RBR) at the JAH VA Hospital). Total RNA was isolated and cDNA used to screen with human LncProfiler (SABiosciences) array comprising of 84 lncRNAs with rigorous controls. Amongst the consistently detected lncR-NAs across all samples, except for GAS5, other lncRNAs did not change significantly. See e.g. Carter, G., Miladinovic, B., Patel, A. A., Deland, L., Mastorides, S. and Patel, N. A. Circulating long noncoding RNA GAS5 levels are correlated to diabetes mellitus. BBA Clinical, 2015 doi: 10.1016/j.bbacli.2015.09.001

The results show that older (>65 y) patients had a decrease in GAS5 expression compared to younger patients (no cancer, no T2DM) (FIG. 1). Comparing over older >65 y, T2DM to normal, the T2DM patients had GAS5 levels less than 10 ng/µl (FIG. 2, HbA1c>6.5 is diabetic) indicating that lower GAS5 levels are correlated with increasing age and insulin resistance.

The lncRNA growth-arrest specific transcript 5 (GAS5) is a 5'-terminal oligopyrimidine class of gene shown to regulate cell growth, proliferation and survival (Coccia E M, Cicala C, Charlesworth A, et al. Regulation and expression of a growth arrest-specific gene (gas5) during growth, differentiation, and development. Molecular and Cellular Biochemistry. 1992; 12(8):3514-21.; and Smith C M and Steitz J A. Classification of gas5 as a multi-small-nucleolar-RNA (snoRNA) host gene and a member of the 5'-terminal oligopyrimidine gene family reveals common features of snoRNA host genes. Molecular and Cellular Biochemistry. 1998; 18(12):6897-909. The biogenesis of GAS5 is established. GAS5 gene transcribes several snoRNAs as well as four splice variants of GAS5 mRNA. However, due to presence of STOP codon, none of the transcripts are transcribed into protein and degrade via the nonsense-mediated decay (NMD) pathway when translation is initiated. The RNA levels of GAS5 are regulated by its degradation instead of regulation at its transcriptional level. GAS5 is encoded at 1q25, a locus displaying abnormalities in a number of cancers (Smedley D. et al. Characterization of chromosome 1 abnormalities in malignant melanomas. Genes Chromosomes Cancer. 2000; 28(1):121-5) and associated with retinopathy and CHD (Qi L, Qi Q, Prudente S, et al. Association between a genetic variant related to glutamic acid metabolism and coronary heart disease in individuals with type 2 diabetes. JAMA. 2013; 310(8):821-8). It is downregulated in breast cancer (Mourtada-Maarabouni M, Pickard M R, et al. GAS5, a non-protein-coding RNA, controls apoptosis and is downregulated in breast cancer. Oncogene (s). 2009; 28(2):195-208.) GAS5 acts as a riborepressor by repressing transcription of glucocorticoid receptor (Kino T. et al. Noncoding RNA gas5 is a growth arrest- and starvation-associated repressor of the glucocorticoid receptor. Science signaling. 2010; 3(107):ra8). GAS5 levels are decreased in the hippocampus of rats with cognitive decline and is associated with the aging brain (See Lee S Y, Hwang Y K, et al. Decreased levels of nuclear glucocorticoid receptor protein in the hippocampus of aged Long-Evans rats with cognitive impairment. Brain research. 2012; 1478: 48-54; Grammatikakis I, Panda A C, et al. Long noncoding RNAs(lncRNAs) and the molecular hallmarks of aging. Aging. 2014; 6(12):992-1009; and Malkki H. Alzheimer disease: Insulin resistance could be linked to risk of AD via reduced glucose uptake. Nature reviews Neurology. 2015; 11(9):485. The role of lncRNAs affecting metabolic pathways in the brain, including lncRNA GAS5 in AD is unknown.

Epidemiological and clinical studies have overwhelmingly confirmed that defective insulin signaling in the brain plays a central role in the early stages of sAD pathology (Id.) Diabetes increases the risk for impaired cognitive function and dementia by 47% (Sebastiao I, Candeias E, et al. Insulin as a Bridge between Type 2 Diabetes and Alzheimer Disease—How Anti-Diabetics Could be a Solution for Dementia. Frontiers in endocrinology. 2014; 5:110; Takeda S, Sato N, et al. Molecular mechanisms linking diabetes mellitus and Alzheimer disease: beta-amyloid peptide, insulin signaling, and neuronal function. Molecular bioSystems. 2011; 7(6):1822-7; Sato N, Takeda S, et al. Role of insulin signaling in the interaction between Alzheimer disease and diabetes mellitus: a missing link to therapeutic potential. Current aging science. 2011; 4(2):118-27. Schrijvers E M, Witteman J C, et al. Insulin metabolism and the risk of Alzheimer disease: the Rotterdam Study. Neurology. 2010; 75(22):1982-7; Matsuzaki T, Sasaki K, et al. Insulin resistance is associated with the pathology of Alzheimer disease: the Hisayama study. Neurology. 2010; 75(9):764-70; Correia S C, Santos R X, et al. Insulin-resistant brain state: the culprit in sporadic Alzheimer's disease? Ageing research reviews. 2011; 10(2):264-73; and Lu F P, Lin K P, et al. Diabetes and the risk of multi-system aging phenotypes: a systematic review and meta-analysis. PLoS ONE. 2009; 4(1):e4144.

Figure 16A:
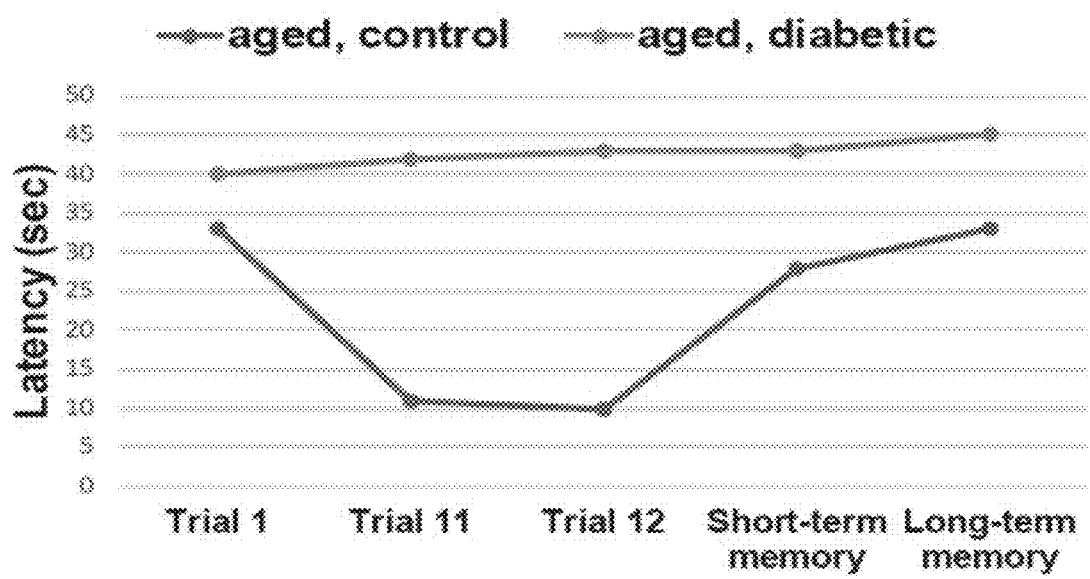
FIGS. 16A-16B show graphs that can demonstrates RAWM in aged-normal and db/db mice. n=8 in each group.
Figure 16B:
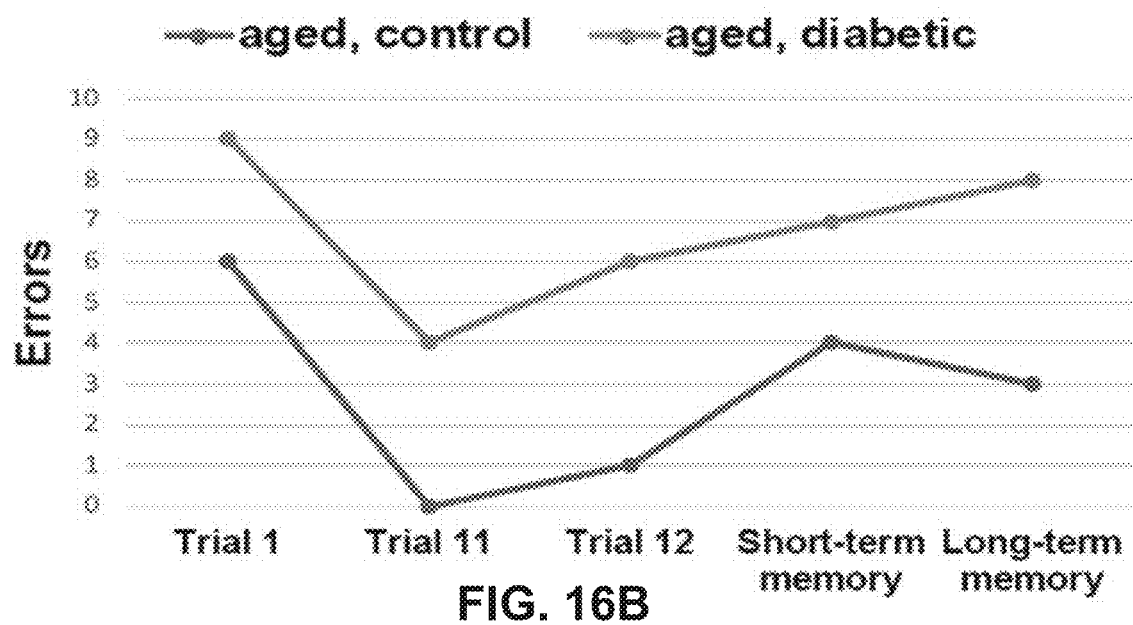

Patients with T2DM have cognitive deficits affecting verbal and nonverbal memory, attention, information processing speed, and executive function (J S R-F, Sa-Roriz T M, et al. (Pre)diabetes, brain aging, and cognition. Biochim Biophys Acta. 2009; 1792(5):432-43). To assess the cognitive function with respect to insulin resistance in vivo, aged diabetic mice BKS.Cg-+ Leprdb/+ Leprdb/OlaHsd (Older db/db mice from Harlan; 11 months—as this mouse model has lower life span) were used along with the normal, age-matched controls and young (4 months) mice. The radial arm water maze (RAWM) was used for cognitive assessment. Errors (incorrect arm choices) and escape latency were recorded for each daily trial (FIGS. 16A-16B). The aged diabetic mice had a marked decline in memory and cognition, as compared to aged non-diabetic mice. The hippocampi of the mice were collected and SYBR Green qPCR was performed. Results indicated that GAS5 and IR levels were lower in aged or aged, diabetic mice than in younger mice (FIG. 3A).

Figure 17:
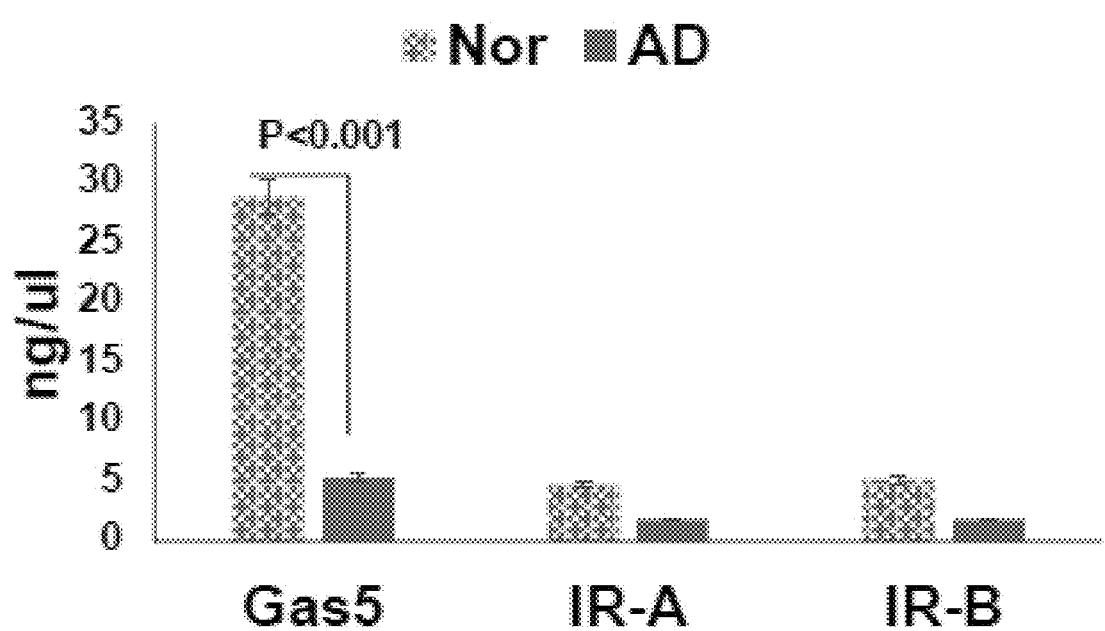
FIG. 17 shows a graph demonstrating absolute qPCR results of normal and AD human brain samples using SYBR green.

To assess the levels of GAS5 in Alzheimer's disease, human brain samples (from temporal lobe) from sAD patients or matched normal (no cancers; 70-85 y; M/F; n=9 each) were analyzed. Results show decreased GAS5 levels with a concurrent decrease in insulin receptors in sAD brain (FIG. 17). This shows expression of GAS5 in aging brain but its expression is significantly decreased in AD.

Figure 18:
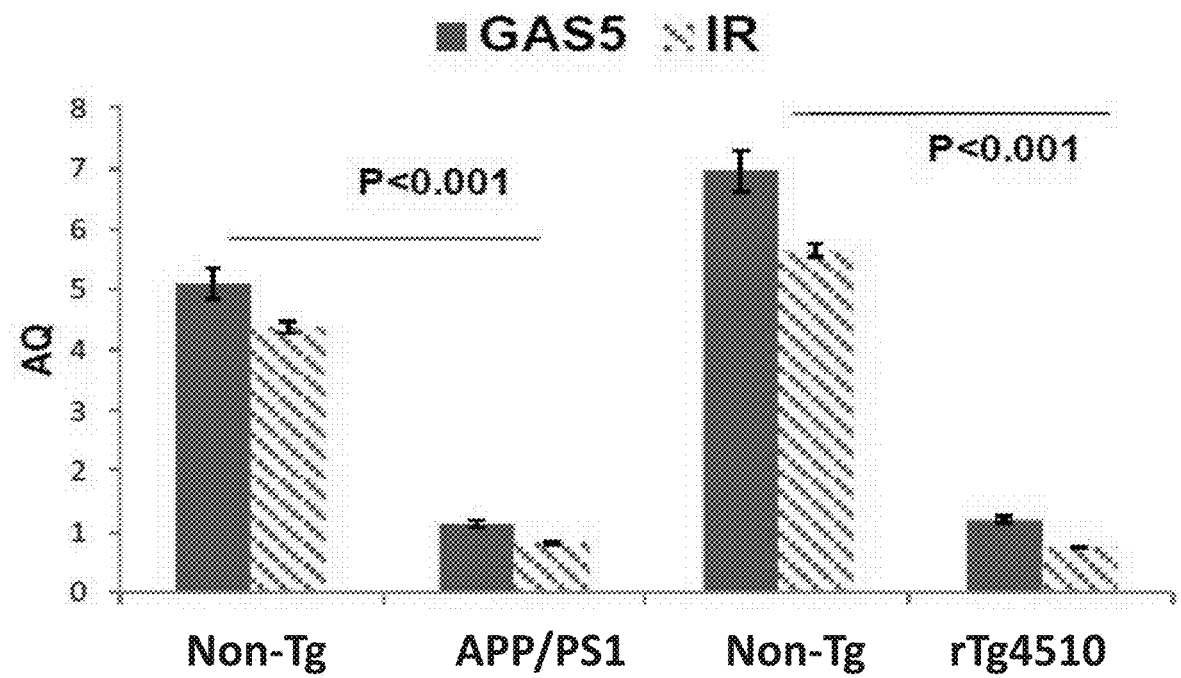
FIG. 18 shows a graph demonstrating absolute qPCR results of cerebral cortex samples from non-transgenic (non-Tg) and 20 month transgenic APPswe/PS1dE9 mice (APP/PS1) and 10 month transgenic rTg4510 mice (rTg4510) for GAS5 and IR (insulin receptor).

Next, cerebral cortex from 20 month transgenic APPswe/PS1dE9 mice and 10 month transgenic rTg4510 mice were analyzed as these mouse model shows amyloid deposition and neuropathology seen in AD (Sanchez-Lopez E, Ettcheto M, et al. New potential strategies for Alzheimer's disease prevention: pegylated biodegradable dexibuprofen nanospheres administration to APPswe/PS1dE9. Nanomedicine: nanotechnology, biology, and medicine. 2016). The age-matched non-transgenic littermates served as control (n=12 in each cohort). Using SYBR Green absolute qPCR (run in triplicate with standard curve), the results show a dramatic decrease in GAS5 and IR levels in APP/PS1 and Tg4510 mice, p<0.001 highly significant unpaired Student's t-test (FIG. 18).

Figure 19A:
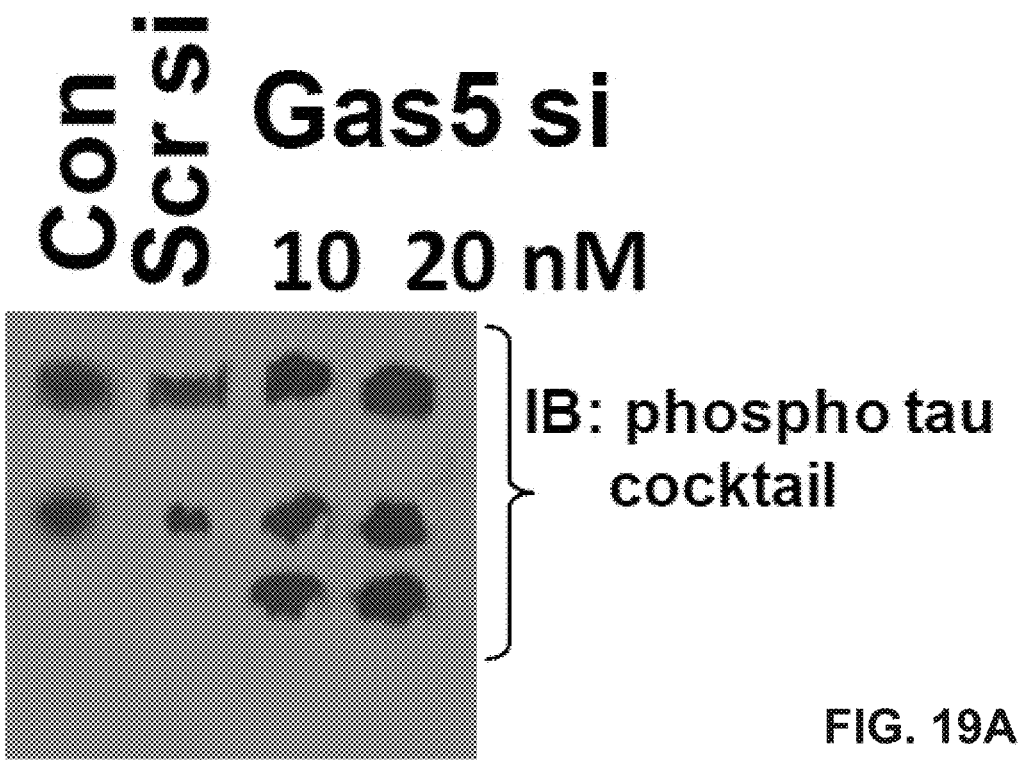
FIGS. 19A-19B show results from a Western blot analysis using (FIG. 19A) phosphor-tau cocktail of antibodies and (FIG. 19B) conditioned media (CM) with anti-APP antibodies (n=3).
Figure 19B:
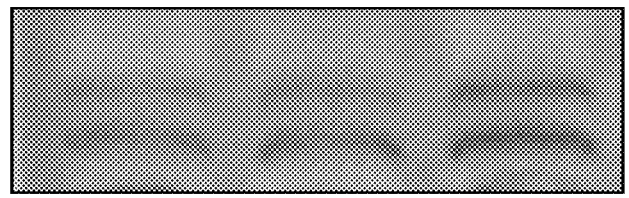
Figure 19B:

The hippocampus is important for memory and cognition. Primary neuronal cells (NC) derived from adult mouse hippocampus were established in culture. These experiments were also repeated with HT22 and SH-SY5Y cell lines with similar results. GAS5 siRNA (10 nM, Ambion 332778, validated using 4 siRNAs to distinct sequences on GAS5 for specificity and efficacy; scrambled siRNA as control) was transfected in NC (Nucelofector 4D, Lonza program E158) for 48 h and knockdown confirmed by GAS5 PCR and product separated on PAGE, silver stained for visualization (FIG. 7A). Separately, cell lysates or conditioned media (CM-collected after 3 days) were collected for western blot analysis. Our results show increased tau phosphorylation and APP levels with depletion of GAS5 (FIG. 19A-19B).

Efficacy of Small-Molecule Compounds in vivo in AD mouse models. The prior results can demonstrate that GAS5 levels are decreased in the AD brain (see e.g. FIGS. 17-18) and in vitro depletion of GAS5 in neurons increases increases phosphorylation of tau and APP accumulation (FIGS. 7A and 19A-19B). Without being bound by theory, it is hypothesized that GAS5 lncRNA can modulate pathways in the etiopathology of AD. As such, a compound capable of binding and/or increasing levels of GAS5 in the brain could be used to treat and/or prevent AD.

Figure 20:
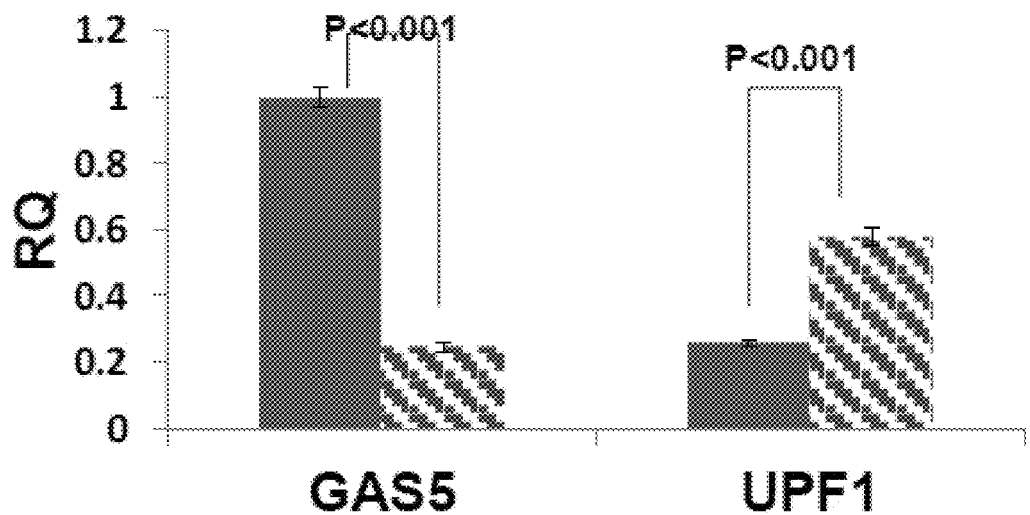
FIG. 20 shows a graph that can demonstrate relative qPCR results of GAS5 and UPF1 in non-transgenic (non-Tg) and APP/PS1 transgenic mice.

The levels of GAS5 are regulated by its degradation instead of regulation at its transcriptional level (Raho G, Barone V, et al. The gas 5 gene shows four alternative splicing patterns without coding for a protein. Gene. 2000; 256(1-2):13-7). Gas5 transcript has a premature termination codon which renders greater susceptibility for nonsense mediated RNA decay. Without being bound by theory, it is hypothesized that GAS5 transcript may be targeted to faster turnover by nonsense mediated RNA decay in sAD consistent with this observation. It was demonstrated that GAS5 levels were increased when UPF1, an essential component of nonsense mediated RNA decay, was depleted (Tani H, Torimura M, et al. The RNA degradation pathway regulates the function of GAS5 a non-coding RNA in mammalian cells. PIoS one. 2013; 8(1):e55684). This demonstrated an inverse relationship of UPF1 and GAS5. Amongst known UPF1 targets are genes associated with glucose metabolism (COIL, ITPR3, TRIM32) which were upregulated when UPF1 was depleted (Tani H, Imamachi N, et al. Identification of hundreds of novel UPF1 target transcripts by direct determination of whole transcriptome stability. RNA biology. 2012; 9(11):1370-9). Since lncRNAs are transcribed but not translated (e.g. no protein is formed), we evaluated whether a deficiency in the transcription machinery assembly in the promoter region inhibits transcription of GAS5. An inhibition of GAS5 transcription in neurons was not observed. The mechanisms of aberrant expression of UPF1 or biogenesis of GAS5 in sAD is not within scope of this grant. GAS5 and UPF1 levels in APP/PS1 mice and its non-Tg littermates (N=8 each) was measured. The data indicated that GAS5 levels were low concurrent with increased expression of UPF1. P<0.001 highly significant between non-Tg and APP/PS1 mice using student's t-test (FIG. 20).

However, it is not advisable to inhibit UPF1 since it is integral to nonsense mediated decay, a crucial surveillance mechanism to reduce errors in gene expression. Additionally, in humans, UPF1 is required for S phase progression and genome stability (Azzalin C M, Lingner J. The human RNA surveillance factor UPF1 is required for S phase progression and genome stability. Curr Biol. 2006; 16(4): 433-9; and Azzalin CM. UPF1: a leader at the end of chromosomes. Nucleus. 2012; 3(1):16-21. Hence, compounds were designed that can disrupt the binding and/or interaction of UPF1 to GAS5 thereby inhibiting GAS5 turnover. GAS5 has premature stop codons UAA upstream of the poly(A) tail. UPF1 binds to this region and tags it for nonsense mediated decay (Tani H, Torimura M, et al. The RNA degradation pathway regulates the function of GAS5 a non-coding RNA in mammalian cells. PIoS one. 2013;

8(1):e55684). A γ-AApeptide based one-bead-one-compound (OBOC) combinatorial library has been developed (Wu H, Li Y, et al. gamma-AApeptide-based small-molecule ligands that inhibit Abeta aggregation. Chemical communications. 2014; 50(40):5206-8). The γ-AApeptide is a peptidomimetic with side chains for chemical diversity and are resistant to proteolytic cleavage. Using this library, a drug has been developed and identified which interrupts STAT3-DNA interaction (Teng P, Zhang X, et al. Identification of novel inhibitors that disrupt STAT3-DNA interaction from a gamma-AApeptide OBOC combinatorial library. Chemical communications. 2014; 50(63):8739-42).

Figure 21:
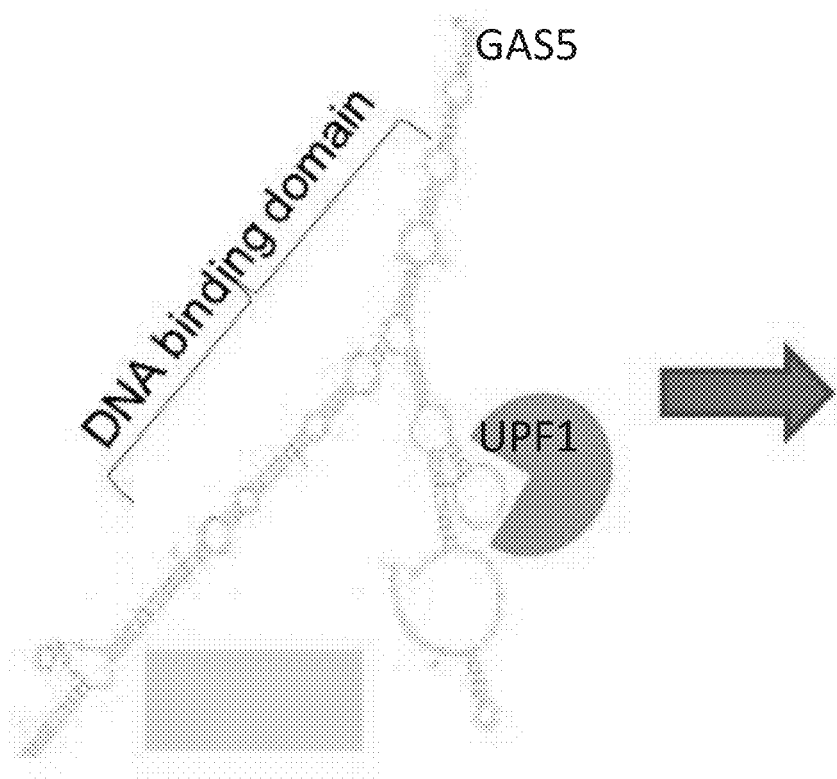
FIG. 21 shows a schematic of G5-1397 (also referred to herein as Formula 3) masking the binding site of UPF1 thereby inhibiting GAS5 transcript turnover via NMD (NMD—nonsense mediated decay).
Figure 21:
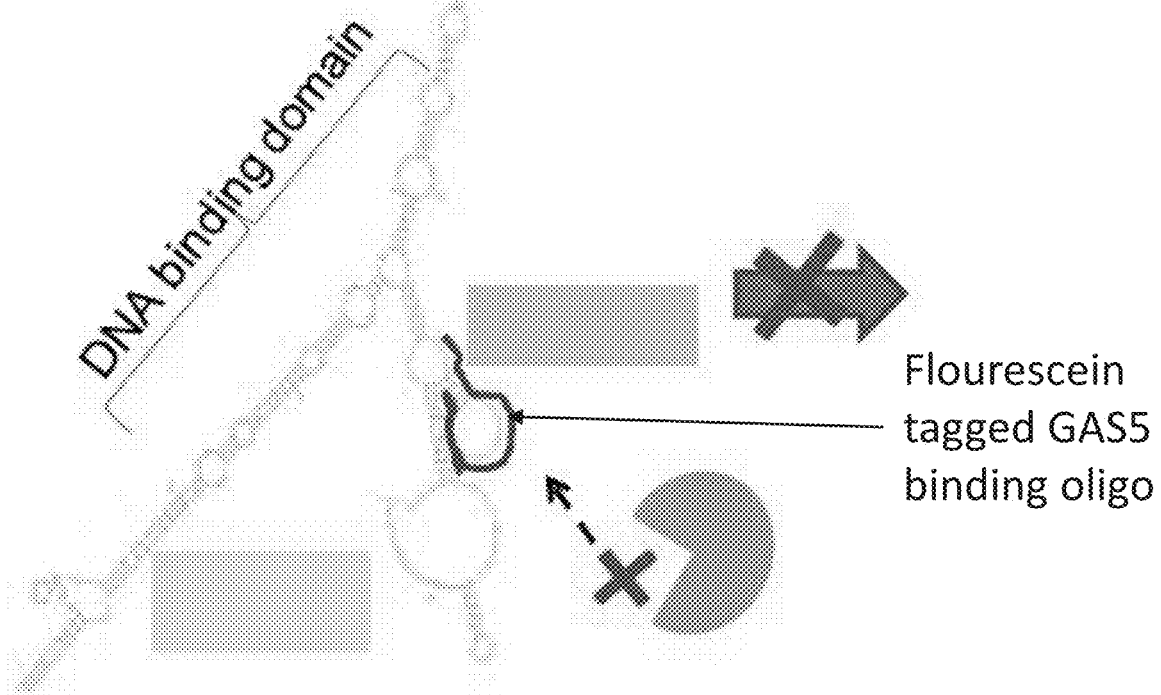

A fluorescein tagged oligonucleotide which spanned 30 nucleotides on either side of the UAA sequences on GAS5 was developed. This is at the 3' end of the transcript (near poly(A) tail) and does not interfere with 5' DNA binding domain of GAS5 through which it interacts with the insulin receptor (FIG. 21]). The length of oligonucleotide was required to maintain stem loop structure to specifically bind to GAS5. Further, the oligonucleotide was molded (using RNAfold software) to evaluate its folding and verified absence of any unwanted secondary structures. The backbone was modified by 2'-MOE which protects it from degradation and a fluorescein tag was attached to the 5'end to aid in screening. The oligonucleotide was used to screen 160,000 molecules in a combinatorial library using tRNA as control (as tRNA has similar stem loop secondary structures). Four positive beads were identified which demonstrated the stringent conditions and high specificity of binding. These compounds have a synthesized RNA-binding domain which is complementary to GAS5-specific oligonucleotide. The compound with strongest binding profile of the four was further modified at its side chain. The modifications were made for high stability and robust binding to GAS5. The compound was tested in vitro for its ability to disrupt binding of UPF1 to GAS5 thereby protecting it from turnover via nonsense mediated decay. These experiments identified a lead small molecule compound (NPG567, which is also referred to herein as Formula 16) that can bind GAS5.

Figure 22:
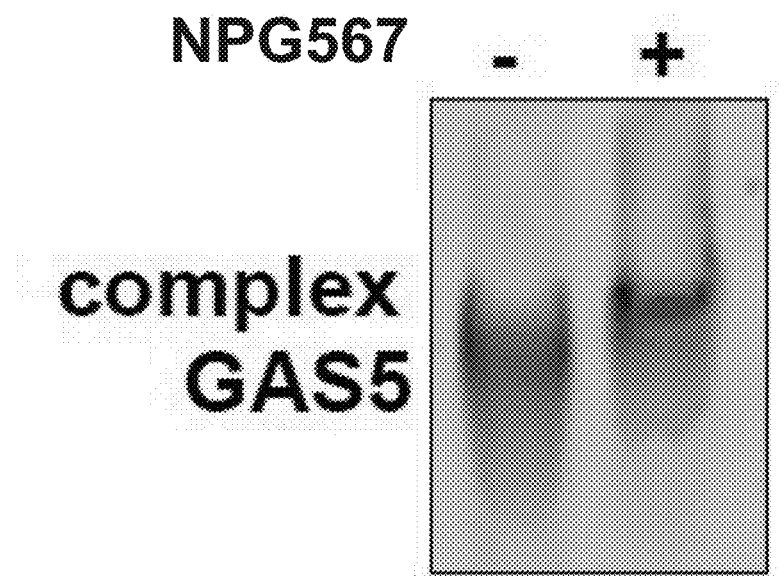
FIG. 22 shows an image demonstrating the results of REMSA of the GAS5 transcript binding to G5-1397 (also referred to herein as Formula 3).
Figure 23A:
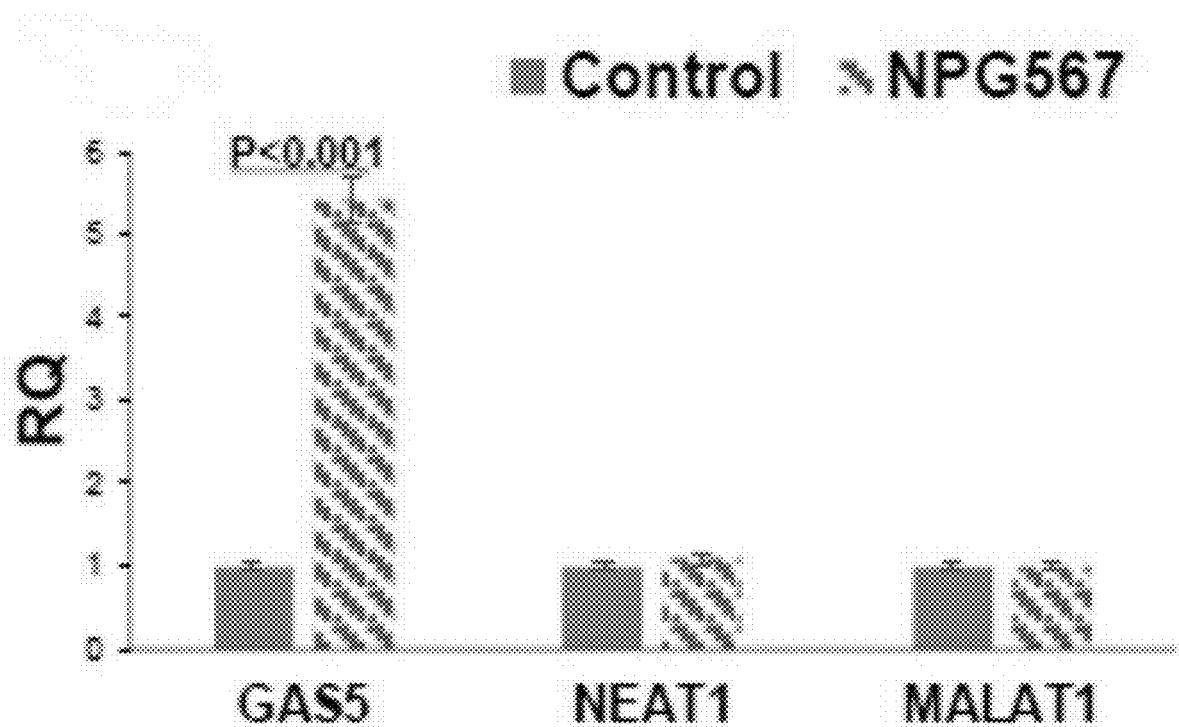
FIG. 23A-23C shows graphs that can demonstrate (FIG. 23A) qPCR using SYBR green (n=4) results with control set as the reference, (FIG. 23B) cell viability assay results with NPG567 (n=4), and (FIG. 23C) SYBR green qPCR of GAS5 and UPF1 (n=4) results.
Figure 23B:
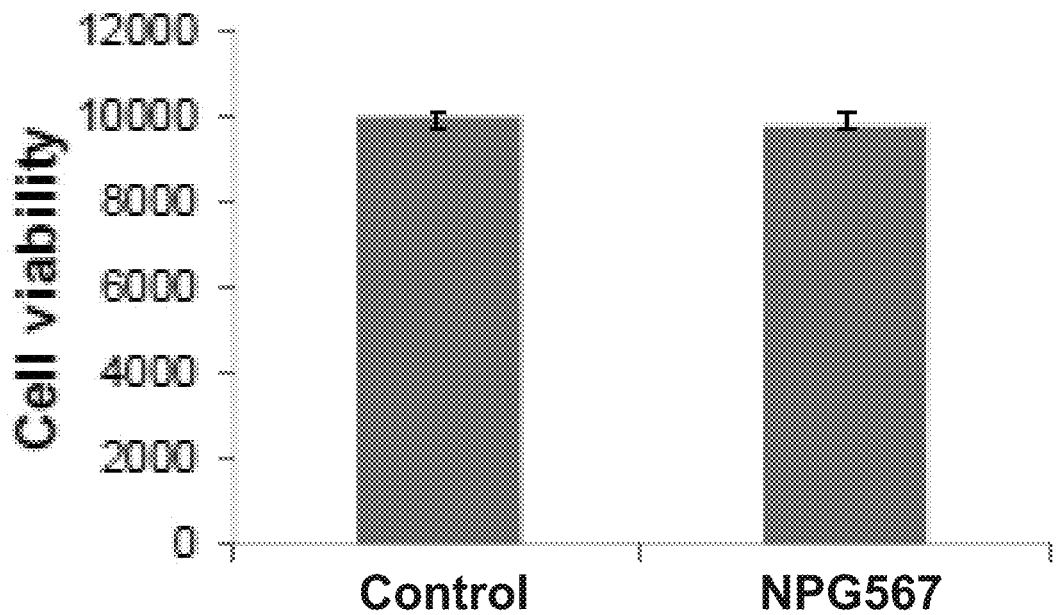
Figure 23C:
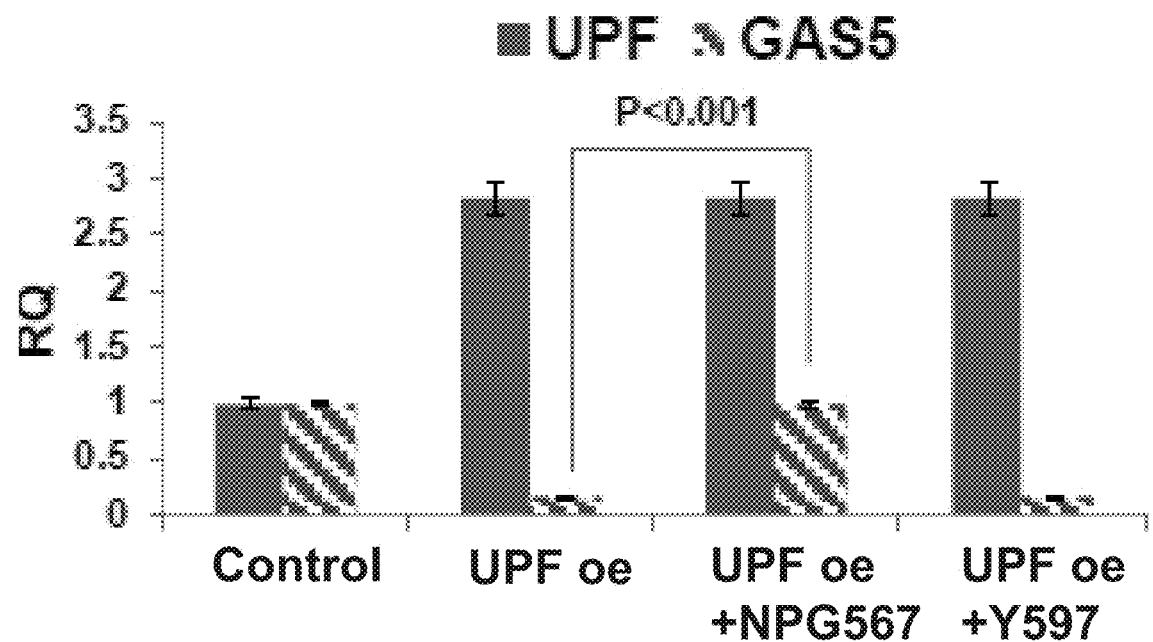

As the compound(s) were designed to bind to GAS5 such that it would disrupt binding to UPF1, the compound(s) ability to bind to GAS5 was examined. RNA-EMSA (RE-MSA) was performed as previously described. Briefly, GAS5 was cloned in TOPO vector which has the T7 promoter. In vitro transcription assay was performed with biotin-label using RiboScribe kit using T7 RNA polymerase at 37° C. for 2 h in the presence of nucleotides, RNase inhibitor, and 5× transcription buffer. 0.1 nM of transcribed, biotin-labeled GAS5 was incubated with 10 nM NPG567 in presence of 10U yeast tRNA and 10 units of RNase inhibitor in a final volume of 10 μl of RNA shift buffer for 20 min at room temperature, detected using Biotin Chromogenic Detection kit (ThermoFisher). The results demonstrate that NPG567 can bind to GAS5 transcript (FIG. 22). NPG567 (10 nM) was observed to be efficiently taken up by NC to increase GAS5 and did not affect levels of other lncRNAs NEAT1, MALAT1 present in neurons (FIG. 23A). NPG567 does not cause cellular toxicity (FIG. 23B) measured using WST-1 assay (Roche). Next, it was evaluated whether NPG567 could stabilize GAS5 in HT22 cells over-expressing UPF1 (from Addgene). UPF1 was transiently transfected for 24 h (UPF oe) or pre-treated with NPG567 (10 nM) for 1 hour followed by transfection of UPF1 for 24 hours. GAS5 levels were measured using SYBR Green qPCR. The results show NPG567 increases GAS5 levels in NC (FIG. 23C). Y59 is a structural analog of NPG567 and was used as control to eliminate non-specific activity.

Figure 24:
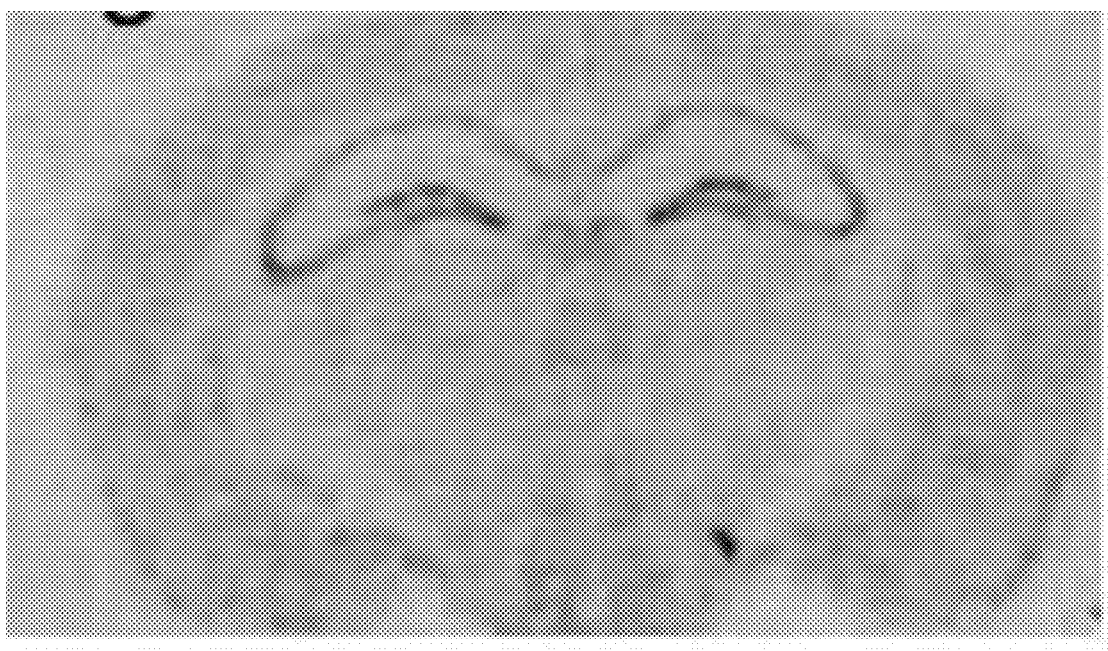
FIG. 24 shows results from in situ hybridization for GAS5 results.

In vivo, GAS5 is present in the brain and particularly in the hippocampus (CA1, CA3, DG) as demonstrated by in-situ hybridization (FIG. 24). Based on this data the impact NPG567 in vitro and in vivo in etiopathology of AD can be evaluated as is discussed below.

In vitro Evaluation of Compound Efficacy. HT22 cells can be treated with NPG567 (10 nM to 500 nM dose curve for 24 h to 72 h for time curve) and expression of GAS5 can be evaluated. $LD_{50}$ using nonlinear regression curve fitting can be determined. A cell toxicity assay (WST1, Roche) can be performed per manufacturer instruction). Viability assays using flow cytometry for Annexin V and propidium iodide staining can be performed. Live cell imaging for apoptosis using CAS-MAP from Vergent Biosciences can be performed. The genetic profiles of GAS5, IR-A and —B, Glut1/3/4, tau, Aβ and UPF1 can be generated using qPCR. Western blot for phospho-tau, total tau, APP, Aβ total, Aβ1-40, Aβ1-42, PHF1, IRS, AKT, PI3K, SIRT1, GSK3β, mTOR can also be performed. Pharmacokinetics (PK; NPG567 concentration (nM) vs time (hour)) and pharmacodynamics (PD; NPG567 effect (on genes) vs time (hour)) can be first established for NPG567 in vitro using techniques and methodologies generally known in the art. The PK/PD results can be mathematically modeled in vitro in HT22 to verify optimal dose ranges and/or efficacious doses and therapeutic index thereby predicting animal dose ranges and minimizing animal numbers. The output of PK/PD study is to calculate Emax (maximum effect) and $EC_{50}$ (drug concentration that causes 50% $E_{max}$).

In vivo Evaluation of Compound Efficacy. The compound (s) including NPG567 will be thoroughly validated as described above. Additionally, derivatives of a lead compound (e.g. YS-D-67 through YS-D-70, which correspond respectively to Formula 15 (YS-D-66), Formula 16 (YS-D-67), Formula 17 (YS-D-68), Formula 18 (YS-D-69), and Formula 19 (YS-D-70), in which the side chain is modified have been generated. Preliminary data showed that they were not toxic to HT22 cells and bound efficiently to GAS5. Depending on the results of the safety, efficacy and distribution in this evaluation, derivatives of NPG567 can be also analyzed using the same assays and methods described herein.

In vivo Saftey and Efficacy Evaluation. Healthy control C57BL/6J mice can be used to evaluate safety and metabolic changes with NPG567 or any other compound described herein treatment and delivery to the brain. Mice can be acclimated to the facility for 1 week prior to treatments. Based on preliminary in vitro PK/PD, NPG567 at 10 nM, 50 nM or 100 nM NPG567 will be administered via 2 routes (Route 1) Intranasal delivery, which is an efficient delivery method to the brain (previously used successfully in other contexts (Apostolatos A, Song S, et al. Insulin promotes neuronal survival via the alternatively spliced protein kinase CdeltaII isoform. J Biol Chem. 2012; 287(12):9299-310), and (Route 2) via subcutaneous pellet (to avoid everyday delivery or daily gavage which may cause distress to rodents in long-term studies; (previously used successfully in other contexts (Nicholson T M, Uchtmann K S, et al. Renal capsule xenografting and subcutaneous pellet implantation for the evaluation of prostate carcinogenesis and benign prostatic hyperplasia. Journal of visualized experiments: JoVE. 2013(78)) and used in AD mice (Baglietto-Vargas D, Medeiros R, et al. Mifepristone alters amyloid precursor protein processing to preclude amyloid beta and also reduces tau pathology. Biol Psychiatry. 2013; 74(5):357-66) and/or via custom subcutaneous pellets from Innovative Research of America) for 3 months to mice (equal M/F, 10 weeks age).

The customized pellets containing the different doses of NPG567 have a biodegradable matrix that continuously releases the drug for 90 days and is implanted into the scruff of the neck.

The increasing doses of the compound(s) can determine the optimum dose and toxicity levels of NPG567 in vivo. The doses are calculated by guidelines from NIH based on NTP, NICEATM. The $LD_{50}$ and $IC_{50}$ derived from in vitro cytotoxicity tests were used to calculate regression within the Fg range. The cohorts are (1) Control (2) 10 nM NPG567 (3) 50 nM NPG567 (4) 100 nM NPG567 (5) 300 nM NPG567 (which is 3 times greater than the calculated highest dose- to determine drug efficacy) (6) vehicle. Mice can be monitored daily for these studies. The mice can be randomly assigned (maintaining equal M/F ratio) to the above groups. The number of animals per group required to detect a difference of 25 to 30% was determined to be 14 at a power of 0.8 by power analysis based on the known variances and the anticipated group mean differences.

After safety evaluation, mice can be housed in metabolic cages (Phenomaster™) for 24 h. Urine and feces can be collected separately in these cages to determine absorption and excretion of NPG567 or other compound(s) described herein. Metabolism can be continuously monitored with $O_2$ intake:$CO_2$ exhaled to calculate respiratory quotient and metabolic rate, calorimetric parameters together with food and water intake. Body weight, temperature, locomotor activity, sleep/awake cycle of mice are monitored and analyzed throughout the experiment. Blood glucose and insulin levels can be measured using techniques generaly known in the art. Mice can then be euthanized and all organs and brain sections can be harvested to assess the distribution of NPG567. Absorption, excretion and distribution of NPG567 can be determined by RP-HPLC. A standard curve for NPG567 or other compound can be generated for HPLC calibration. The samples can be extracted and re-constituted in acetone and used in RP-HPLC.

It can be determined if NPG567 or other compound (e.g. a derivative of NPG567 or other compound described herein) increases GAS5 expression in vivo in the brain. Blood and CSF will be collected to analyze GAS5 levels. Brain tissue will be sliced into sections and collected for histological studies. ISH (in situ hybridization) can be used to analyze bio-distribution of NPG567 or other compound described herein in the brain. The remainder of tissue can be snap-frozen and stored for proteomic and transcriptomic analysis. The genetic profiles of GAS5, IR, Glut4, tau, Aβ and UPF1 can be determined using SYBR Green qPCR. Western blot analysis for phospo-tau, total tau, APP, Aβ total, Aβ1-40, Aβ1-42, pIRS, PI3K, pAKT, SIRT1, mTOR, GSK3β can be performed using techniques generally known in the art. Neurotoxicity with NPG567 or other compound described herein can be evaluated using stereology for NeuN as well as examining hippocampal volume and cell layer thickness (Bachstetter A D, Morganti J M, et al. Fractalkine and CX(3)CR1 regulate hippocampal neurogenesis in adult and aged rats. NeurobiolAging. 2009; and Tajiri N, Acosta S A, et al. Intravenous transplants of human adipose-derived stem cell protect the brain from traumatic brain injury-induced neurodegeneration and motor and cognitive impairments: cell graft biodistribution and soluble factors in young and aged rats. J Neurosci. 2014; 34(1):313-26). Briefly, while sectioning the brain tissue, every $6^{th}$ sagittal section can be about 40 μm thick to allow for stereological analysis. This can allow for the determination if GAS5 modulation in vivo has any neurotoxic effects independent of AD pathology.

Evaluation of Compounds Efficacy in an AD mouse model. Animal models can be useful tools for studying pathogenesis of AD. Rodent models are particularly used as they demonstrate neurobehavioral pathology including plaque formation and cognitive loss. Several transgenic mice overexpressing mutant forms of APP, presenilin or tau proteins in the brain are currently available. For this study, transgenic APPswe/PS1dE9 (aka APP/PS1) and rTg4510 were chosen as data presented in FIG. 18 can show evidence of GAS5 correlation to Alzheimer's pathology in these mouse models. The APP/PS1 mice show increased Aβ42 early in life and onset of plaque pathology at 9 months of age and cognitive loss at 11-12 months. In addition, the compounds can be examined in another model of AD pathology-rTg4510 Tau model, which over-expresses tau carrying a mutation linked to human disease (P301L) in neurons of the forebrain and develops tauopathy, cognitive impairments and neurodegeneration. This allows for the examination of NPG567 to Tau pathology in vivo. The genetic background for the mouse models is complex and appropriate littermate non-Tg controls can be be used. These mouse models have been previously established. The rationale behind choosing at least two mouse models is that it call allow for delineation of the effects of compound NPG567 or other compounds described herein on regulating the AD etiopathology with the distinct biology presented individually by these models and the observed decline in memory, recognition and cognition.

Doses, which can include an optimum dose of NPG567 or other compound described herein as determined by in vitro and/or in vivo efficacy studies can be be given to APP/PS1 and non-Tg littermate control mice using subcutaneous pellets beginning at either 6 months of age (preventive) or 12 months of age (therapeutic) and can be tested for cognitive function at about 14 months or other ages as desired. Mice can be examined for amyloid pathology during the progression of treatment, e.g. 8, 10, 12, 14 months to determine if there is a reduction of progression of pathology from treatment onset or actual reduced levels of amyloid pathology from that present at treatment onset.

The Tg4510 and its non-Tg littermates (due to the difference in pathology onset age) can be treated with or without NPG567 (at varying dosages including those determined to be desirable from in vitro and/or in vivo efficacy studies previously described) using subcutaneous pellets beginning at either 3 months of age (e.g. preventive) or 8 months of age (e.g. therapeutic) and tested for cognitive function at 10 months. Mice can be examined for tau pathology at 4, 6, 8, 10 months to determine if there is reduction post-treatment compared to that at treatment onset. See FIG. 25A for a schematic of the experimental protocol.

Figure 25A:
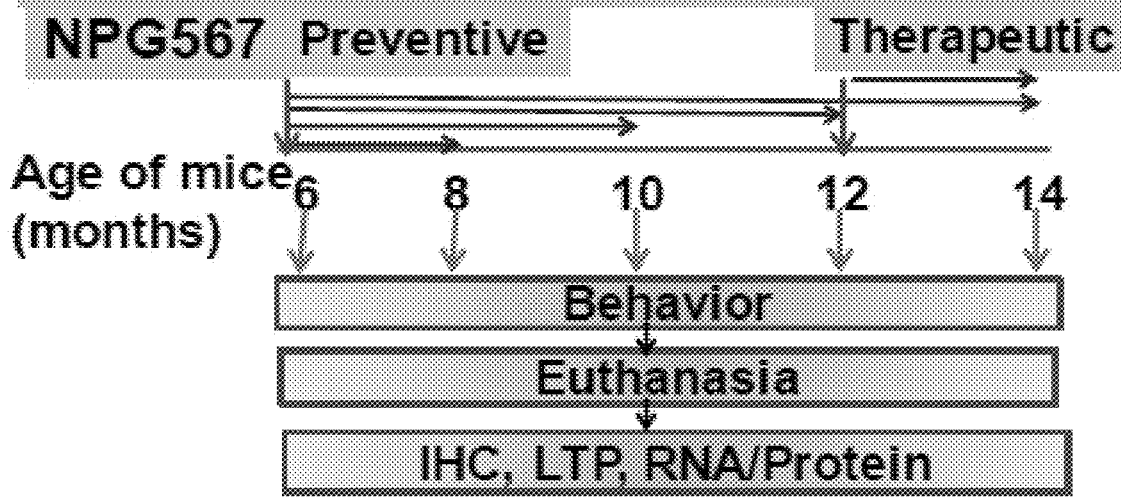
FIGS. 25A-25B shows a schematic of a protocals that can be used to determine preventive and therapeautic efficacy of NPG567 or any other compound described herein as delivered by subcutaneous pellet (FIG. 25A) or intranasal administration (FIG. 25B).
Figure 25B:
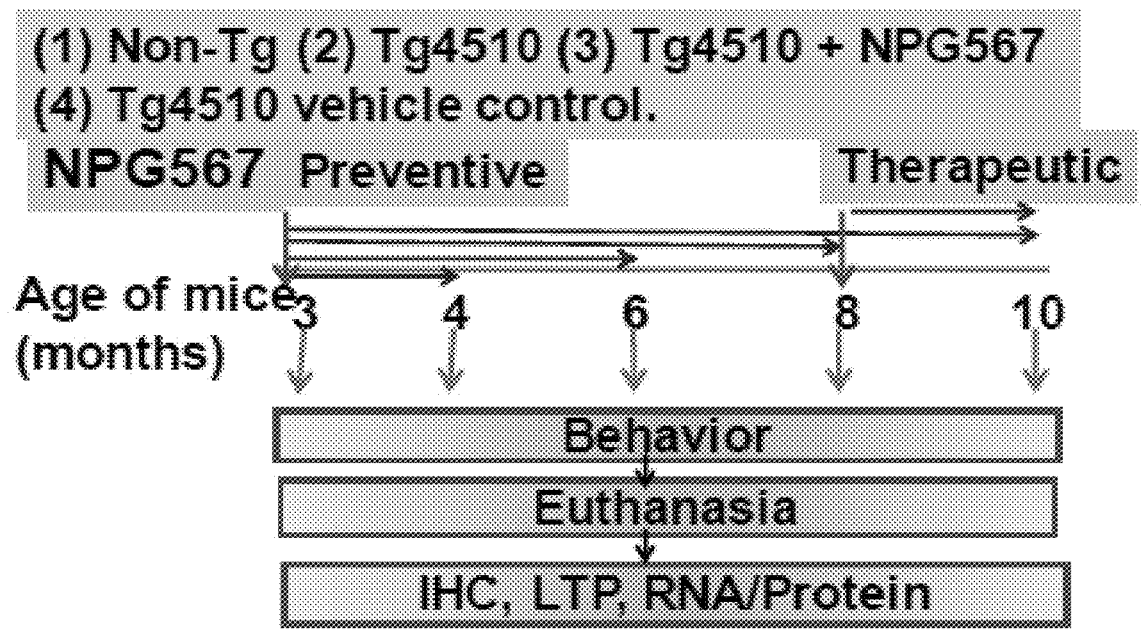
Figure 26:
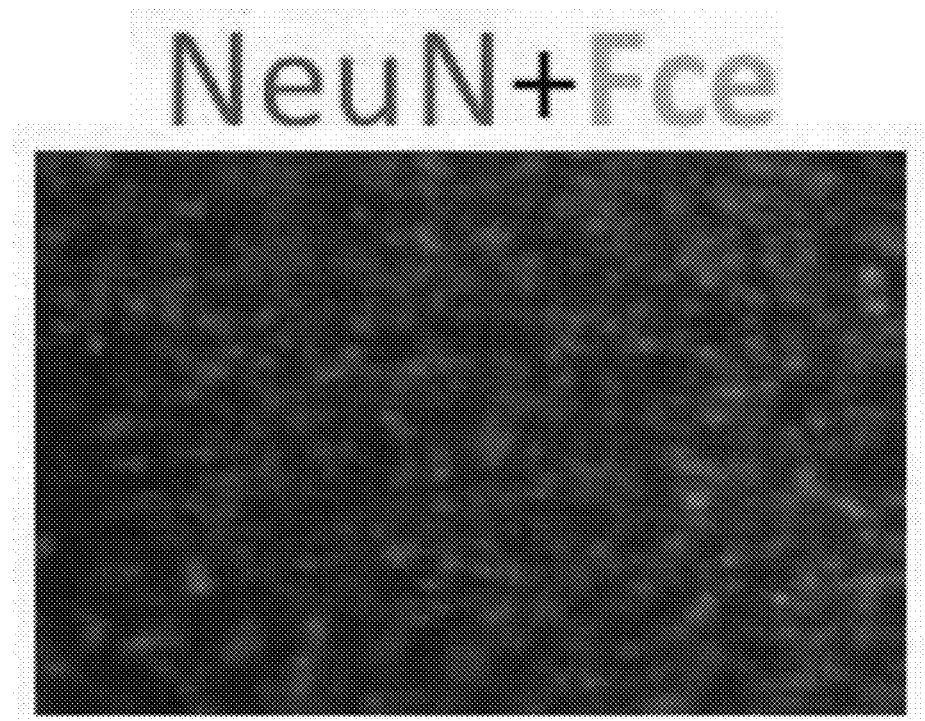
FIG. 26 shows a fluorescent microscopy image that can demonstrate the effect of fluorescein-labeled NPG567 (10 nM in 10 µl total volume, alternating nostrils) administered intranasally to 14 week C57BL/6 mice (n=4). Brain tissue was harvested after about 48 h.
Figure 27:
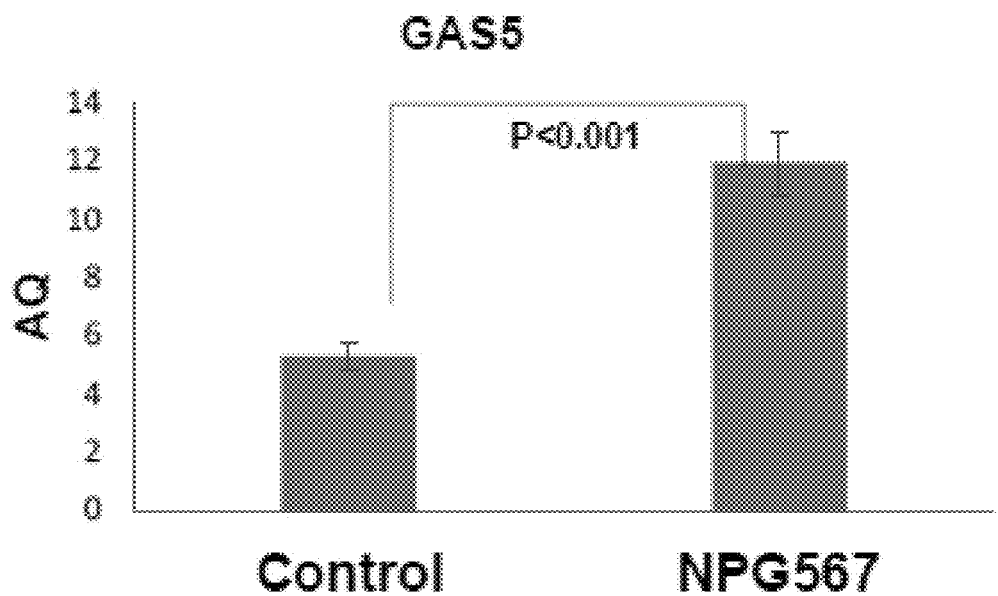
FIG. 27 shows a graph that can demonstrate that NPG567 crossed the blood-brain barrier and taken up by the brain and increased GAS5 levels in the hippocampus.

Separately, NPG567 or other compounds can be administered by intranasal delivery (APP/PS1 beginning at either 6 months of age (preventive) or 12 months of age (therapeutic); dose repeated alternate days; Tg4510 beginning at either 3 months of age (preventive) or 8 months of age (therapeutic); alternate days. See FIG. 25B for a schematic of the experimental protocol. The treatment efficacy for the two modes of delivery at timeframes as shown in FIGS. 25A and 25B and described herein. Intranasal delivery is a noninvasive method that bypasses the blood-brain barrier and delivers the drug to the brain and the spinal cord, thereby avoiding any systemic side effects. FIG. 26 shows that fluorescein-labeled NPG567 (10 nM in 10 μl total volume, alternating nostrils) was administered intranasally to 14 week C57BL/6 mice (n=4). Brain tissue was harvested after about 48 h. Results indicate that NPG567 crossed the blood-brain barrier and taken up by the brain and increased GAS5 levels in the hippocampus (FIG. 27). The results indicated that it was not toxic to the animals.

The mice in the above cohorts for both methods of drug delivery (N=14 male/female APP/PS1 or non-TG with or without NPG567 and separately 14 M/F Tg4510 or non-TG with or without NPG567) can be examined behaviorally in matched sub-cohorts of 20 mice spaced over several months.

Benchmarks. Behavioral Tests: will be rotarod, open field, novel object, novel place, contextual and cued fear conditioning and 6 arm radial arm water maze at 14 months of age. All such methodologies are fully explained in the art and will be appreciate by one of ordinary skill in the art. At the end of the behavioral testing (2 weeks later) mice can be euthanized and split into subgroups of 6-7 mice each for immunohistochemistry or LTP/biochemistry.. For the immunohistochemistry, biochemistry, and LTP, the 6-7 mice per subgroup per outcome (e.g., immunohistochemistry) enables us to detect differences in the order of d=0.67. These effect sizes estimate are conservative and are smaller than those observed by in other studies previously performed (Bachstetter A D, Morganti J M, et al. Fractalkine and CX(3)CR1 regulate hippocampal neurogenesis in adult and aged rats. NeurobiolAging. 2009). Mice for immunohistochemistry can be perfused with 4% paraformaldehyde and mice for LTP and biochemistry can be euthanatized and the brain dissected on ice, for LTP. For electrophysiology studies, the left hippocampus can be used for CA1 NMDAR dependent LTP and LTD (Rogers J T, Morganti J M, et al. CX3CR1 Deficiency Leads to Impairment of Hippocampal Cognitive Function and Synaptic Plasticity. J Neurosci. 2011; 31(45):16241-50) and the rest of the brain is dissected into cortex, hippocampus, cerebellum, striatum, brainstem and right hippocampus.

Immunohistochemistry: Free-floating sections (40 μm sagittal sections) to examine hippocampus and cortex can be immunostained for AR by antibody 4G8, thioflavin-S histochemistry and congo red staining, soluble and insoluble amyloid; pathological tau species: oligomeric, p-tau (AT8, PHF1), cTau. These sections can be stained with NeuN for neuronal cells. To evaluate proliferation of neural progenitors, hippocampal dentate sub granular zone will be stained with Ki67 for proliferation and doublecortin (DCX) to assess newborn neurons undergoing maturation. The sections for amyloid pathology can be scanned and analyzed using Zeiss AxioScan Slide scanner for densitometry analysis. Separate sections can be used in stereological analysis to examine neurogenesis (Ki67 and DCX) and neuronal numbers (NeuN). To evaluate proliferation of neural progenitors, hippocampal dentate sub granular zone can be stained with Ki67 for proliferation and doublecortin (DCX) to assess newborn neurons undergoing maturation, which can allow for determination of efficacy of a compound.

Biochemical analysis: Tissue can be sliced into sections snap-frozen in liquid nitrogen and stored at −80° C. for proteomic and transcriptomic analysis. To assess the systemic effect of NPG567, protein profiling can be performed using LC/MS. For transcriptomic analysis for coding and noncoding RNA, samples can be evaluated using RNAseq (RNA sequencing). For both these analysis, samples can be pooled, differentiated by cohorts, from mice at 14 months (from both modes of delivery). Separately for all time points, the genetic profiles of GAS5, IR, Glut3/4, Aβ and UPF1 can be determined using SYBR Green qPCR. Western blot analysis for p-tau, tau, APP, Aβ total, Aβ1-40, Aβ1-42, PHF1, pIRS, PI3K, pAKT, AKT, PDK1, PKCs, Gluts 1-8, PI3K p110/p85, SIRT1, mTOR, GSK3β can be performed.

Furthermore, detergent-soluble and guanidine-extractable Aβ species can be analyzed by ELISA (47). Efficacy of a compound can be determined based on the ability of the compound to improve insulin signaling, decrease tau phosphorylation and/or aggregation of β-amyloid.

Blood and CSF can be collected to measure APP, AR species, circulating GAS5 levels, glucose and insulin levels. Mice can be euthanized and all organs and brain tissue can be harvested. Additionally, genes involved in inflammation and apoptosis (MCP1, TNFα and IL6 along with additional cytokines (interleukins, NFkB pathway), Bcl2, AKT, PTEN, Bax, Bid, Caspase-3, 8, 9 (as sAD pathology is accompanied by perturbations in these pathways and may be influenced by NPG567), insulin, and genes in the JAK/STAT pathways can be evaluated. Efficacy of a compound can be determined based on the ability of the compound to improve insulin signaling, decrease tau phosphorylation, aggregation of β-amyloid, and/or apoptosis.

Metabolomics: The complete metabolite and biochemical status of NPG567 (or other compound described herein) treated hippocampal neurons can be generated such that the changes in the networks and pathways are deciphered which can provide insights into complete physiological and pathological states post-treatment. Efficacy of a compound can be indicated by a change in the metabolite panel towards a healthier outcome (e.g. a decrease in proteins affecting tau phosphorylation and β-amyloid accumulation).

Animal Numbers. Animal numbers are summarized with n=14 (balanced M/F) for each cohort. For the in vivo safety and efficacy studies the animal number can total 90 C57BL6/6J mice. Mice can be purchased from Jackson labs at 6 months of age. For the evaluation of the compound(s) efficacy in the AD mouse model, mice purchased and maintained in Byrd Alzheimer's, cohorts can be used to determine behaviour followed by IHC and biochemistry and electrophysiology. For APP/PS1 cohort, 14×3 treatments (no treatments, NPG567 (or other compound described herein) and vehicle)×7 time points (treatment initiation 6 mo—collected at 6, 8, 10, 12, 14 months and treatment initiation 12 mo—collected at 14 mo)=294 M/F mice with non-Tg littermates 14×7 time points=98 M/F mice. 2 delivery routes can be used, hence 2×294=588 M/F mice and 2×98=196 non-Tg littermates. The same calculations (14×3×7×2) can apply to Tg4510 (588 M/F mice) and their non-Tg littermates (14×7×2=196 M/F mice).

Example 5. Determination of Insulin Receptor Dependent Molecular Mechanisms by which GAS5 can Mediate sAD Pathology Introduction. Glucose metabolism is crucial for the brain and plays an important role in sAD (Hoyer S. Glucose metabolism and insulin receptor signal transduction in Alzheimer disease. Eur J Pharmacol. 2004; 490(1-3):115-25) Insulin in the brain may be attributed to peripheral origin and crossing the blood brain barrier; more recently it was shown that brain synthesizes insulin. Reduced levels of insulin receptors in the brain are seen in the elderly and in patients with dementia and Alzheimer's disease (Arvanitakis Z, Wilson R S, et al. Diabetes mellitus and risk of Alzheimer disease and decline in cognitive function. Arch Neurol. 2004; 61(5):661-6.). Insulin receptors are expressed throughout the brain with highest concentration in hypothalamus, cerebral cortex, hippocampus and olfactory bulb. As shown in FIG. 8, insulin can bind to the insulin receptors (IR) to initiate the insulin signaling cascade with PI3K→AKT as a crucial node influencing etiopathology of AD. Decreased IR expression can lead to a decrease in PI3K→AKT, which can affect two important pathways: (1) decreases glucose transporters, which can reduce glucose uptake and (2) decreases the phosphorylation of GSK3β, which can lead to its hyperactivation. This increased activity of GSK3β can increase phosphorylation of tau culminating in neurofibrillary tangles as well as accumulation of amyloid-β (Aβ) peptides which form plaques. Furthermore, decreased glucose intake in the brain can decrease Tau O-GlcNAcylation which also promotes hyperphosphorylation of tau. Separately, as insulin is not efficiently taken up due to decreased IR expression, excess extracellular insulin can inhibit insulin degrading enzyme (IDE). IDE also functions to degrade AR and inhibition of IDE results in further accumulation of Aβ. Separately, in events leading to decreased insulin signaling via its receptors, Aβ oligomers can activate TNFα/JNK pathway to phosphorylate IRS1, which can lead to further inhibition of physiological phosphorylation of IRS1. These events taken together can finally culminate in the clinical diagnosis of AD with decreased cognition and neuronal function as its hallmarks.

Figure 9:
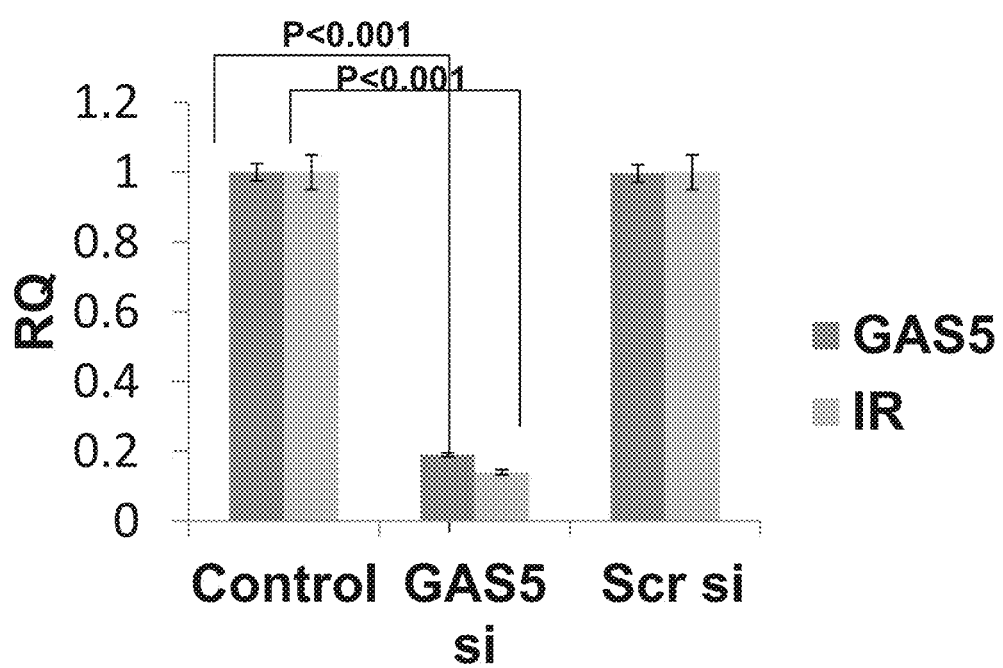
FIG. 9 shows a graph demonstrating the results of a SYBR Green relative qPCR analysis with control NC set as a reference. This was repeated 5 times and similar results were obtained.

Genes involved in glucose metabolism that may be affected by depletion of GAS5 were evaluated. Customized human glucose metabolism array (Qiagen) was used to screen for expression of 84 genes related to the glucose metabolism and insulin resistance. NC were depleted using GAS5 siRNA as above in e.g. Example 4 (FIG. 9). The array results showed that GAS5 depletion resulted in dramatic inhibition of insulin receptor (IR). These results were individually verified using SYBR Green qPCR (FIG. 7B), NC—control set as reference in calculating RQ in qPCR; p<0.001 highly significant using two-tailed Student's t-test). In vivo data from human sAD brain and AD transgenic mice (FIGS. 17-18) show decreased IR expression concurrent with decreased GAS5 levels.

Figure 28:
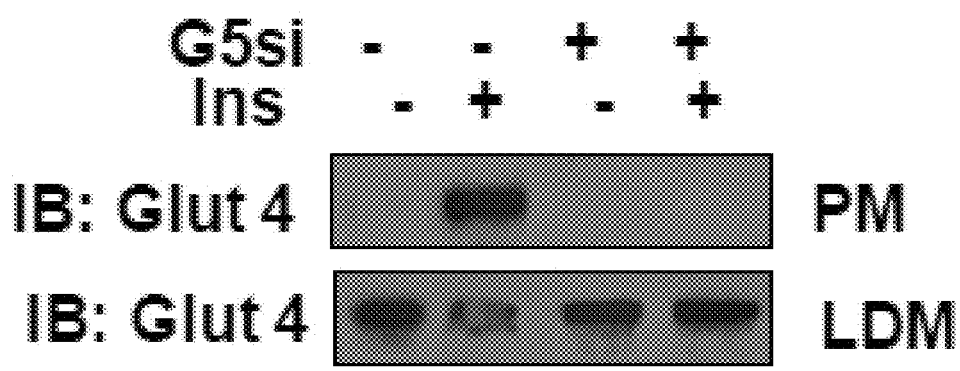
FIG. 28 shows an image of a blot that can demonstrate a depletion of GAS5 can inhibit insulin mediated GLUT4 translocation.

The effect of GAS5 depletion on glucose uptake in NC was evaluated. GAS5 was depleted using siRNA (FIG. 9) and glucose uptake assay was performed. Cells were serum starved, 10 nM insulin was added to cells for 30 minutes and [3H]-deoxy-2-D-Glucose uptake was measured. As shown in FIG. 7B) indicated a decrease in glucose uptake in GAS5 depleted NC (***p<0.001, highly significant using two-tailed students t-test). These results indicate that GAS5 levels influence glucose uptake. In the hippocampus, the primary glucose transporter is GLUT4 (with lower expression of GLUT 3, followed by GLUT1,2,5, and 8). Subcellular fractionation was performed (57, 58) to determine translocation of Glut4 to plasma membrane in GAS5siRNA treated NC. As shown in FIG. 28, results show depletion of GAS5 inhibited insulin mediated GLUT4 translocation.

LncRNAs have structural and spatial features which allow it to bind to DNA, RNA or protein partners thereby regulating transcription of genes. The data showed GAS5 depletion significantly inhibited insulin receptor IR (IR-A predominantly expressed in the brain), we hypothesized that GAS5 may regulate transcription of IR and not alternative splicing or other post-transcriptional mechanism. Hence, a computational analysis using LaserGene™ software was performed to determine whether GAS5 may bind to the promoter region of IR. Our analysis showed that the sequence "aacgtttttat" (SEQ ID NO: 5) on IR promoter region (at −826 bp) is 100% complementary to a sequence on GAS5 DNA binding domain.

Next it was investigated whether GAS5 could bind to IR promoter and sequester RNA polymerase II for transcription initiation. A Chromatin-RNA immunoprecipitation (Ch-RIP) assay in NC was performed. Following chromatin fixation, immunoprecipitations performed with anti-RNA polymerase II (IgG IP serves as control). (i) Immunoprecipitated DNA was analyzed by semi-quantitative PCR using primers amplifying two regions on the IR promoter: −580 to −860 bp; −1480 to −1810 bp. These regions were assessed as putative GAS5 binding regions based on computational analysis for complementary sequence. Input DNA (1:10 of released chromatin) was included in PCRs. (ii) the cross linking was reversed, RNA was isolated from the immunoprecipitated complex and GAS5 was detected using qPCR. These results (FIGS. 10A-10B) indicate that GAS5 binds to the IR promoter between −580 to −860 bp simultaneously in a complex with RNA polymerase II. Additionally, using an IR promoter deletion series with CAT reporter, we show that GAS5 binds to IR promoter at 826 bp and activates its transcription. The data can demonstrate that GAS5 acts as a riboactivator and promotes transcription of insulin receptor (IR). Without being bound to theory, it is hypothesized that GAS5 regulates insulin signaling pathway in neurons, which can promote sAD pathology.

The Effect of GAS5 on tau phosphorylation and Aβ levels via insulin signaling pathways. To determine that GAS5 levels affect tau phosphorylation and AR levels via insulin signaling pathways, GAS5 can be over-expressed (bought from Addgene #46370) or knocked down using GAS siRNA (described above) or treatment with 10-100 nM NPG567 for 24-72 h in HT22 cells. Separately, hippocampal explants from APP/PS1 and Tg4510 along with the respective non-Tg littermates can be incubated with fluorescein labeled NPG567 (10-100 nM) for 24 to 72 h (time and dose response) in SCM (fetal calf serum). Cells can be stained with Tuj1, NeuN and images merged with fluorescent image.

Next, insulin receptor can be depleted using IR siRNA (Ambion 103297, validated, along with scrambled control; 10-50 nM dose curve for 24-72 h) followed by over-expression of GAS5 in HT22 cells. Plasmids can be transiently transfected 1-3 µg for 24-72 hours for optimization using Nucleofector as described above.

Benchmarks: For the above experiments, explants and cells can be analyzed biochemically using qPCR for GAS5, IR, Glut3/4, Aβ and UPF1 and signaling pathways evaluated by western blot analysis for pIRS, PI3K, pAKT, AKT, PDK1, PKCs, Gluts 1-8, PI3K p110/p85, SIRT1, mTOR, GSK3β, APP, Aβ total, Aβ1-40, Aβ1-42, P-tau, PHF1. Additionally, tau phosphorylation will be evaluated using phospho-tag gel analysis (Kinoshita E, Kinoshita-Kikuta E, et al. Two-dimensional phosphate-affinity gel electrophoresis for the analysis of phosphoprotein isotypes. Electrophoresis. 2009; 30(3):550-9; and Abisambra J F, Blair L J, et al. Phosphorylation dynamics regulate Hsp27-mediated rescue of neuronal plasticity deficits in tau transgenic mice. J Neurosci. 2010; 30(46):15374-82. Briefly, cell lysates can be incubated with λ-phosphatase to allow separation of phosphorylated proteins from their non-phosphorylated proteins and immunoblotted.

Glucose uptake assays can be performed on IR depleted HT22 cells with varying concentrations of GAS5 (as described in described relation to FIGS. 7B, 9 and 28). Separately Glucose uptake assays will be performed in cells treated with NPG567. Glut4 translocation to plasma membrane can be evaluated by flow cytometry (Koshy S, Alizadeh P, et al. Quantitative measurement of GLUT4 translocation to the plasma membrane by flow cytometry. Journal of visualized experiments: JoVE. 2010(45)) and correlate to GAS5 levels. Cell proliferation and viability can be evaluated using MTT assays (Roche, per manufacturer's instructions) in the above experiments. BrdU and Propidium iodide (PI) flow cytometry can be conducted to determine if GAS5 affects apoptosis and cell cycle in neurons as previously described (Apostolatos H, Apostolatos A, et al. Vitamin A metabolite, all-trans-retinoic acid, mediates alternative splicing of protein kinase C deltaVIII (PKCdeltaVIII) isoform via splicing factor SC35. J Biol Chem. 2010; 285(34): 25987-95; Apostolatos A, Song S, et al. Insulin promotes neuronal survival via the alternatively spliced protein kinase CdeltaII isoform. J Biol Chem. 2012; 287(12):9299-310; Carter G, Apostolatos A, et al. Dysregulated Alternative Splicing Pattern of PKC during Differentiation of Human Preadipocytes Represents Distinct Differences between Lean and Obese Adipocytes. ISRN Obesity. 2013; 2013:9; Carter G, Patel R S, et al. Protein kinase C delta splice variant modulates senescence via hTERT in adipose derived stem cells. Stem Cell Investigations. 2014; 1(3); and Patel R, Apostolatos A, et al. Protein kinase C delta (PKCdelta) splice variants modulate apoptosis pathway in 3T3L1 cells during adipogenesis: identification of PKCdeltaII inhibitor. J Biol Chem. 2013; 288(37):26834-46).

SmartFlare™ RNA fluorescence can be used to detect GAS5 levels in live cells. This technology (Millipore; our specific probes verified in lab) uses target-specific probes bound to gold nanoparticles with fluorophore (Cy5/Cy3). Upon binding to its target, fluorescence is activated and detected. This is directly proportional to the amount of RNA; 18S probe is added simultaneously as an internal control. The SmartFlare™ probe is taken up by endocytosis by cells. The cells can then be used for flow cytometry, qPCR and western blots as described above. This can elucidate binding of GAS5 to IR promoter in mediating signaling pathways in neurons in AD. A Nikon A1R+ confocal microscope with hybrid scanhead (Galvano and resonant scanners) can be used to capture dynamic 3D images with time lapse and tracking.

The above experiments can be performed in HT22 cells, SH-SY5Y, and primary neuronal cultures from APP/PS1 and Tg4510 mice with non-Tg controls (see Example 4).

These experiments can demonstrate the molecular mechanisms mediating tau phosphorylation and Aβ accumulation via regulation of insulin signaling by noncoding GAS5 in neurons. For translational relevance, this can eb established in neuronal cultures from APP/PS1 and Tg4510 to examine both APP and Tau pathology in isolation. This can support the interpretation of interactions of GAS5 with these molecular pathways independent of each other. Both mice models are available and primary cells are routinely cultured. Lower insulin receptors decrease the individual's sensitivity and cause insulin resistance. This mechanism is separate from insulin-induced internalization and degradation of IR. Several studies are published with neuron specific IR knockout models and its implications in AD; here its role in pre-initiation complex assembly on IR promoter is deciphered.

Example 6

Determination of the Impact of GAS5 on Metabolic Pathways in sAD.

Without being bound to theory, the effect of GAS5 in neurons can be mediated via insulin-independent pathways and the effect of GAS5 on relevant metabolic pathways in the brain can be evaluated as described herein. Without being bound by theory, it is hypothesized that GAS5 can serve as a node to mediate neuronal metabolic pathways both via regulation of insulin receptor expression as well as by mediating SIRT1 and mTOR complexes. This is important because sAD is a multi-faceted disease and decrease in lncRNA GAS5 may affect multiple pathways culminating in tau and amyloid pathology and promoting the onset of sAD pathology.

The mammalian target of rapamycin (mTOR) is a serine/threonine protein kinase known to regulate cell growth and metabolism in response to signals such as neurotrophins, insulin, cytokines, IGF-I, TNF and VEGF. The mTOR pathway can be activated by several signals: PI3K/AKT, mitogenic signals through Ras/MEK/ERK pathway, AMPK or by hypoxia. mTOR signaling plays a central role in the aging brain (Baar E L, Carbajal K A, et al. Sex- and tissue-specific changes in mTOR signaling with age in C57BL/6J mice. Aging cell. 2016; 15(1):155-66; Lamming D W, Ye L, et al. Rapalogs and mTOR inhibitors as anti-aging therapeutics. J Clin Invest. 2013; 123(3):980-9; and Johnson S C, Rabinovitch P S, et al. mTOR is a key modulator of ageing and age-related disease. Nature. 2013; 493(7432):338-45. In AD, mTOR signaling is compromised with increased amyloid plaque formation and defects in the autophagy process (Li Q, Liu Y, et al. Autophagy and Alzheimer's Disease. Cellular and molecular neurobiology. 2017; 37(3):377-88; and Ma Y Q, Wu D K, et al. mTOR and tau phosphorylated proteins in the hippocampal tissue of rats with type 2 diabetes and Alzheimer's disease. Mol Med Rep. 2013; 7(2):623-7). mTOR is central to two large multi-protein complexes mTOR complex 1 and 2 (mTORC1 and mTORC2). mTORC1 mediated activation of S6 kinase (S6K), subsequently causes phosphorylation and degradation of insulin receptor substrates 1 and 2. On the other hand, mTORC2 activation results in increased AKT mediated glucose transporter translocation into the cellular membrane.

Silent information regulator factor 2-related enzyme1 (Sirt1) is a nicotinamide adenine dinucleotide-dependent class III histone deacetylase that is involved in an array of functions such as cell longevity, genomic stability and gene silencing. Sirt1 is important for neuronal plasticity, cognitive functions and protects against aging-associated neuronal degeneration and cognitive decline. Decrease in Sirt1 in neurons is associated with increased AR accumulation (Ibani D, Polito L, et al. Sirtuins as novel targets for Alzheimer's disease and other neurodegenerative disorders: experimental and genetic evidence. Journal of Alzheimer's disease: JAD. 2010; 19(1):11-26; and Donmez G, Wang D, et al. SIRT1 suppresses beta-amyloid production by activating the alpha-secretase gene ADAM10. Cell. 2010; 142(2)). Sirt1 also mediates mTOR signaling (Qiang L, Wang H, et al. Adiponectin secretion is regulated by SIRT1 and the endoplasmic reticulum oxidoreductase Ero1-L alpha. Molecular and Cellular Biochemistry. 2007; 27(13):4698-707; Costa Cdos S, Rohden F, et al. Resveratrol upregulated SIRT1, FOXO1, and adiponectin and downregulated PPARgamma1-3 mRNA expression in human visceral adipocytes. Obesity surgery. 2011; 21(3):356-61; Blagosklonny M V. TOR-centric view on insulin resistance and diabetic complications: perspective for endocrinologists and gerontologists. Cell death & disease. 2013; 4:e964; and Chong Z Z, Maiese K. Mammalian target of rapamycin signaling in diabetic cardiovascular disease. Cardiovascular diabetology. 2012; 11:45). Sirt1 has been shown to inhibit the function of mTORC1 by an upstream activation of the TSC1/TSC2 complex that further inhibits Rheb, an activator of mTORC1. Furthermore, the downregulation of Sirt1 results in downregulation of the mTORC2 complex since it controls the expression of Rictor, a component of the mTORC2 complex, by interacting with NRF1 on the NRF1-binding sites of Rictor promotor region. We evaluated the levels of Sirt1 upon GAS5 depletion.

GAS5 siRNA was transfected (as described above) in NC and SYBR Green qPCR was used to evaluate SIRT1 levels. The results show decrease in Sirt1 in GAS5 depleted NC (FIG. 11A). Separately, cell lysates were immunoprecipitated with mTOR and immunoblotted with Rictor (component of mTORC2). Our results show decreased association of mTOR with Rictor in GAS5 depleted NC (FIG. 11B). Similar results obtained with HT22 and SHSY5Y cell lines.

The mechanisms of GAS5 via insulin dependent and independent mechanisms can be delinated by evaluating pathways in response to GAS5 with and without depletion of insulin receptor (IR). These experiments can be carried out in HT22 cells, SH-SY5Y, and primary neuronal cultures from WT and APP/PS1 (amyloid only) and Tg4510 (tau only) mice (see Example 4).

Inhibitors to known signaling cascades can be used to identify other pathways affected by GAS5. In these experiments, inhibitors (ranging from 1-50 nM) can be added 1 hour prior to manipulating GAS5 levels (over-expression and knockdown as previously described). LY294002 (PI3K inhibitor), PD153035 (tyrosine kinase inhibitor), AG490 (Jak2 inhibitor) and U0126 (MEK1/2 inhibitor) can be used in this assay. Separately, cells will be treated with NPG567 (ranging from 1-100 nM for 24-72 h) to evaluate its effect on signaling pathways. An efficacious compound can result in an increase or decrease of activation of the signaling pathways discussed above. It will be apparent to those of ordinary skill in the art which pathways are up and down regulated in response to an efficacious compound in view of this disclosure.

To determine the impact of GAS5 levels on metabolic pathways independent of IR, HT22 cells can be be depleted of IR as described above. GAS5 can be over-expressed as above in these IR-depleted HT22 cells. It can be evaluated if GAS5 level causes a preferential shift in mTORC2 formation over mTORC1 thereby affecting kinase signaling pathway. Protein lysates can be immunoprecipitated with mTOR and immunoblotted with Raptor, PRAS40 (mTORC1 specific components) and Rictor, mSIN1, Protor 1/2 (mTORC2 specific components). An efficacious compound can result in an increase or decrease of activation of the metabolic pathways discussed above. It will be apparent to those of ordinary skill in the art which pathways are up and down regulated in response to an efficacious compound in view of this disclosure.

Decrease in Sirt1 in neurons is associated with increased AR accumulation. The data shows depletion of GAS5 decreased Sirt1. To evaluate the role of GAS5 mediated AR accumulation, Sirt1 can be depleted using siRNA (Ambion 136457, validated, along with scrambled control; 10-50 nM dose curve for 24-72 h) to evaluate if GAS5 alone affects AR accumulation or it is via SIRT1.

Benchmarks: For the experiments described above, whole cell lysates and conditioned media will be used in western blot analysis for phospo-tau, total tau, PHF1, APP, Aβ total, Aβ1-40, Aβ1-42, γ-secretase, p-IRS, IRS, p-AKT, AKT, PDK1, PKCs, Gluts 1-8, PI3K p110/p85, JAK/STAT, AMPK, MAPK, GSK3β. RNA can be isolated and SYBR Green Real-time qPCR can be performed for IR, GAS5, SIRT1, TAU, mTOR. An efficactious compound can result in an increase or decrease of activation of the signaling pathways discussed above. It will be apparent to those of ordinary skill in the art which pathways are up and down regulated in response to an efficacious compound in view of this disclosure.

Statistical analysis: Experiments are repeated 5 times. Each sample will be analyzed 3-5 times to control for analytical impression and will ensure reproducibility of results. PRISM™ and SPSS software will be used for analysis of statistical significance (Student's t-test, ANOVA) with $p<0.05$ considered significant.

Methods in brief: Cell culture: Immortalized clonal mouse hippocampal cell line (HT22) (obtained from Salk Institute) and cultured in DMEM+10% FBS. Primary neuronal culture from hippocampus of APP/PS1 and its non-transgenic littermate and from Tg4510 and non-Tg littermate will be established as described previously. The hippocampus can be dissected, minced into small pieces using a scalpel and trypsinized to remove extracellular matrix. After incubation, the tissue is dissociated by trituration and single cell suspension is obtained. The cells are checked for viability and counted and plated into T-25 flasks in neurobasal media with B27 supplement. After approximately 7 days, neurons can be verified using anti-tubulin antibody and NeuN. The cell cultures can be tested using short tandem repeat profiling. It will be sent to Idexx BioResearch for authentication. Transient transfection: HT22 cells or primary neurons can transfected in dishes using Nucleofector 4D (AD1 mix, Program E158) Other methods are described previously (Apostolatos H, Apostolatos A, et al. Vitamin A metabolite, all-trans-retinoic acid, mediates alternative splicing of protein kinase C deltaVIII (PKCdeltaVIII) isoform via splicing factor SC35. J Biol Chem. 2010; 285(34):25987-95; Apostolatos A, Song S, et al. Insulin promotes neuronal survival via the alternatively spliced protein kinase CdeltaII isoform. J Biol Chem. 2012; 287(12):9299-310; Carter G, Apostolatos A, et al. Dysregulated Alternative Splicing Pattern of PKC during Differentiation of Human Preadipocytes Represents Distinct Differences between Lean and Obese Adipocytes. ISRN Obesity. 2013; 2013:9; Carter G, Patel R S, et al. Protein kinase C delta splice variant modulates senescence via hTERT in adipose derived stem cells. Stem Cell Investigations. 2014; 1(3); and Patel R, Apostolatos A, et al. Protein kinase C delta (PKCdelta) splice variants modulate apoptosis pathway in 3T3L1 cells during adipogenesis: identification of PKCdeltaII inhibitor. J Biol Chem. 2013; 288(37): 26834-46).

Example 7

Introduction. Diabetes Mellitus comprises a group of metabolic diseases characterized by hyperglycemia, impaired insulin action and/or secretion. Type 1 Diabetes Mellitus is juvenile onset diabetes in which the insulin producing pancreatic β cells are destroyed (insulin-dependent). Type 2 Diabetes Mellitus (T2DM) is commonly diagnosed in middle aged individuals and is frequently associated with insulin resistance and impaired insulin signal transduction; with less than 15% insulin sensitive. T2DM is polygenic; insulin-receptor double knockouts can cause T2DM[1, 2]. While the underlying genetics of T2DM has been extensively studied, the emphasis has been on genes encoding transcribed and translated messages. However, it is becoming increasingly clear that noncoding transcripts play an important role in disease manifestation.

Long noncoding (lnc) RNAs are orchestrators of essential biological networks with varied mechanisms including regulation of signaling, molecular decoys, scaffolding and guiding ribonucleoprotein complexes. Multiple lines of evidence link regulatory lncRNAs to human diseases[3-6]. The lncRNA growth-arrest specific transcript 5 (GAS5) is a 5'-terminal oligopyrimidine class of gene shown to regulate cell growth, proliferation and survival[7, 8]. The biogenesis of GAS5 is established. GAS5 gene transcribes several snoRNAs as well as four splice variants of GAS5 mRNA. However, due to presence of STOP codon, none of the transcripts are transcribed into protein and degrade via the nonsense-mediated decay (NMD) pathway when translation is initiated. The RNA levels of GAS5 are regulated by its degradation instead of regulation at its transcriptional level [9]. GAS5 is encoded at 1q25, a locus displaying abnormalities in a number of cancers[10] and associated with retinopathy and CHD[11]. GAS5 inhibits actions of rapamycin which is an mTOR inhibitor and this affects both leukemic and untransformed human T-lymphocytes[12]. It is down-regulated in breast cancer[13]. GAS5 acts as a riborepressor by repressing transcription of glucocorticoid receptor[14]. However, the role of GAS5 in T2DM is unknown.

Adipose tissue (AT) is an important endocrine regulator of energy homeostasis and glucose metabolism. AT is a primary organ for glucose uptake and storage of excess energy. Insulin increases the rate of glucose transport across the membrane and increases glycolysis. AT also secretes metabolites such as leptin, adiponectin, free fatty acids, inflammatory cytokines which impact glucose metabolism in the body. AT plays a central role in the development of insulin resistance and subsequently of T2DM. The importance of AT in T2DM is underscored by its impact through lipodystrophy and obesity in the development of insulin resistance.

AT was evaluated to understand the role of GAS5 in glucose metabolism. A strategy for a small molecule targeted to GAS5 transcript was designed such that it inhibited UPF1-mediated turnover. Formula 16 (also referred to herein as YS-D-67 or NPG567 in neurons shows specificity and is not toxic to cells and may be developed as a therapy to modulate complications with diabetes mellitus.

Results.

GAS5 is decreased in adipocytes from diabetic patients. Previously, a transcriptomics approach was used to screen lncRNA levels in serum of patients with or without T2DM. A marked decrease in GAS5 expression was observed in type 2 diabetic (T2DM) samples compared to non-diabetic while the other lncRNAs did not change significantly (REF). It was demonstrated that individuals with serum GAS5<10 ng/µl have almost twelve times higher odds of having T2DM (Exact Odds Ratio [OR]=11.79 (95% CI: 3.97, 37.26), p<0.001) (REF). As such, evaluating the role of GAS5 in T2DM was focused on.

Here, the expression of GAS5 in abdominal omental AT from nondiabetic and T2DM patients (IRB20295) was determined; all lean patients with BMI 22.1±2; 6 non-diabetic patients HbA1c 5.4±0.7; 6 T2DM patients HbA1c 8±0.7; both groups nonsmokers, no cancers, other criteria matched). Omental AT was digested with collagenase and purified to obtain adipocytes (free from other cells and macrophages). Adipocytes were maintained in culture for 48 hours (adipocyte media from ZenBio™) and conditioned media (CM) was collected to analyze its secretome. Using SYBR Green absolute qPCR for GAS5 we show that T2DM patients have significantly decreased expression of GAS5 in adipocytes and its secretome compared to non-diabetic.

High glucose was not observed to affect GAS5 levels: To address whether GAS5 levels changed due to T2DM or GAS5 levels contributed to metabolic changes which ultimately result in T2DM, we incubated non-diabetic adipocytes (isolated as described above from patients) with 25 mM glucose for 1-5 days. The real time qPCR results indicated that hyperglycemia did not influence the levels of GAS5. This can indicate that decrease in GAS5 levels is not a consequence of T2DM.

Depletion of GAS5 decreases glucose uptake: Adipose tissue is the primary target for insulin-mediated glucose uptake. Hence, we sought to evaluate the effect of GAS5 depletion on glucose uptake. To maintain reproducibility over a larger number of experiments, adipose stem cells derived from normal or diabetic patients were purchased from Zenbio (BMI 20-24, Nondiabetic HbA1C 5.9 (hereafter referred as NDM); T2DM HbA1c 8.5 (hereafter referred as DM)). The adipose stem cells (ASC) were differentiated in vitro to mature adipocytes and used in experiments. GAS5 siRNA (10 nM, Ambion 332778, validated; scrambled siRNA as control) was transfected in NDM pre-adipocytes for 48 h, differentiated to mature NDM adipocytes for 8 days and knockdown confirmed by GAS5 SYBR Green qPCR. We determined the effect of GAS5 depletion on glucose uptake by NDM adipocytes. Cells were serum starved, 10 nM insulin was added to cells for 30 minutes and [$^3$H]-deoxy-2-D-Glucose uptake was measured. Results indicated a decrease in glucose uptake in GAS5 depleted NDM adipocytes ***p<0.001, highly significant using two-tailed students t-test. These results indicate that GAS5 influences glucose uptake.

Depletion of GAS5 inhibits Glut4 translocation in adipocytes: Following insulin receptor (IR) binding and signal transduction, glucose transporters are recruited from the intracellular pool to the plasma membrane, exposing functional glucose transporters to the extracellular medium containing glucose. In adipose tissue, the primary glucose transporter is GLUT4 (with GLUT1 to a lesser extent). Hence, subcellular fractionation was performed[15, 16] to determine translocation of Glut4 from cytosol to plasma membrane in GAS5 siRNA treated NDM adipocytes (as above). The results show depletion of GAS5 inhibited insulin mediated GLUT4 translocation.

GAS5 regulates expression of insulin receptor: As the data showed that GAS5 depletion decreased glucose uptake, the genes involved in glucose metabolism that may be affected by depletion of GAS5 was evaluated. Customized human diabetes array (Qiagen) was used to screen for expression of 84 genes related to the onset, development, and progression of diabetes. The array results showed that GAS5 depletion resulted in dramatic inhibition of insulin receptors (IR-α and IR-β). These results were individually verified using SYBR Green qPCR (NDM set as reference in calculating RQ in qPCR; inset shows silver-stained PCR products).

GAS5 binds to the promoter of insulin receptor: LncRNAs have structural and spatial features which allow it to bind to DNA, RNA or protein partners thereby regulating transcription of genes. As the data showed GAS5 depletion significantly inhibited both insulin receptors IR-A and IR-B, it suggested that GAS5 may regulate transcription of IR and not alternative splicing or other post-transcriptional mechanism. A computational analysis using LaserGene™ software was performed to determine whether GAS5 may bind to the promoter region of IR. Our analysis showed that the sequence "aacgttttat" (SEQ ID NO: 5) on IR promoter region (at −826 bp) is 100% complementary to a sequence on GAS5 DNA binding domain.

It was next investigated whether GAS5 could bind to IR promoter and sequester RNA polymerase II for transcription initiation. We performed the Chromatin-RNA immunoprecipitation (Ch-RIP) assay in NDM adipocytes. Following chromatin fixation, immunoprecipitations performed with anti-RNA polymerase II (IgG IP serves as control). (i) Immunoprecipitated DNA was analyzed by semi-quantitative PCR using primers amplifying two regions on the IR promoter: −580 to −860 bp; −1480 to −1810 bp. These regions were assessed as putative GAS5 binding regions based on computational analysis for complementary sequence. Input DNA (1:10 of released chromatin) was included in PCRs. (ii) the cross linking was reversed, RNA was isolated from the immunoprecipitated complex and GAS5 was detected using qPCR. These results indicate that GAS5 binds to the IR promoter between −580 to −860 bp simultaneously in a complex with RNA polymerase II. The results demonstrate that GAS5 acts as a rioactivator and promotes transcription of IR.

Binding of GAS5 to promoter of insulin receptor activates transcription: It was investigated whether GAS5 binding to IR promoter could increase transcription of IR. IR promoter deletion plasmid series with a CAT reporter (REF) was used. GAS5 was over-expressed GAS5 (from Addgene #46370) by transfection in NDM preadipocytes for 48 hours followed by transfection of human IR promoter deletion plasmid series with CAT reporter: pIRC1 (-1823), pIRC 3 (-1311) or pIRC5 (-746). pBLCAT8+, the parental vector served as control. Chloramphenicol acetyl transferase (CAT) gene expression was measured using real-time qPCR (REF). Results showed depletion of GAS5 decreases expression of CAT reporter gene in pIR1 and pIRC3 but this is abolished in pIRC5 indicating that GAS5 binding site was deleted.

GAS5 depletion inhibits insulin signaling pathway: Since the results demonstrated that GAS5 regulates the expression of insulin receptor, we sought to evaluate its role in insulin signaling. About 10 nM insulin was added to NDM adipocytes for 24 hours. Real-time qPCR analysis showed an increase in GAS5 levels. Separately, GAS5 was depleted in NDM adipocytes using GAS5 siRNA as described above to evaluate the insulin receptor mediated PI3K→AKT pathway. Whole cell lysates were evaluated by western blot analysis using antibodies against p-AKT and total AKT. Results demonstrate decrease in phosphorylation of AKT with depletion of GAS5 while the total AKT levels remained constant.

Drug design to stabilize GAS5 levels: The data shows that depleted GAS5 levels affect glucose metabolism and insulin signaling which are critical components attributed to metabolic syndrome and T2DM. The hallmark of T2DM is the development of insulin resistance. While in a normal state, improving insulin sensitivity would promote obesity; in a diabetic state, reducing insulin resistance would revert glucose homeostasis to its normal functioning. Current treatment regiments in diabetes aim at reducing insulin resistance and improving glucose metabolism. Hence it was sought to develop a drug that could stabilize GAS5 levels in vivo. The goal of the drug is not to boost insulin sensitivity in adipocytes to higher levels, but to bring it back to its pre-diseased conditions, and thus to normal physiological functioning.

The levels of GAS5 are regulated by its degradation instead of regulation at its transcriptional level[9]. Gas5 transcript has a premature termination codon which renders greater susceptibility for nonsense mediated RNA decay. It was demonstrated that GAS5 levels were increased when UPF1, an essential component of nonsense mediated RNA decay, was depleted[17]. This demonstrated an inverse relationship of UPF1 and GAS5. GAS5 and UPF1 levels were measured in NDM and DM adipocytes. The data indicated that GAS5 levels were low in DM adipocytes concurrent with increased expression of UPF1 compared to NDM adipocytes.

It is not advisable to inhibit UPF1 since it is integral to nonsense mediated decay, a crucial surveillance mechanism to reduce errors in gene expression. Additionally in humans, UPF1 is required for S phase progression and genome stability[18, 19]. Hence, we designed a novel strategy to disrupt the binding of UPF1 to GAS5 thereby inhibiting GAS5 turnover. GAS5 has premature stop codons UAA upstream of the poly(A) tail. UPF1 binds to this region and tags it for nonsense mediated decay[17]. Hence, we sought to disrupt the interaction between UPF1 and GAS5. A γ-AA-peptide based one-bead-one-compound (OBOC) combinatorial library has been developed[20]. The γ-AApeptide is a peptidomimetic with side chains for chemical diversity and are resistant to proteolytic cleavage. Using this library, he has successfully screened and developed a drug which interrupts STAT3-DNA interaction[21].

A fluorescein tagged oligonucleotide was synthesized (Eurofin), which spanned 30 nucleotides on either side of the UAA sequences on GAS5. This is at the 3' end of the transcript (near poly(A) tail) and does not interfere with 5' DNA binding domain of GAS5 through which it interacts with the insulin receptor. The length of oligonucleotide was required to maintain stem loop structure to specifically bind to GAS5. Further, we modeled the oligonucleotide (RNAfold software) to evaluate its folding and verified absence of any unwanted secondary structures. The backbone is modified by 2'-MOE which protects it from degradation and a fluorescein tag was attached to the 5'end to aid in screening. The oligonucleotide was used to screen 160,000 molecules in the combinatorial library using tRNA as control (as tRNA has similar stem loop secondary structures).

To Identify ligands for GAS5 lncRNA from the library, we incubated the beads with GAS5 (20 nM) and t-RNA (competitors to minimize non-specific interaction) in Tris buffer. The beads emitting green fluorescence were picked up as positive hits. Followed by the on-bead cleavage and the sequence analysis, four positive beads were identified which demonstrated the stringent conditions and high specificity of binding. These compounds have a synthesized RNA-binding domain which is complementary to GAS5-specific oligonucleotide. These compounds were tested in vitro for their ability to disrupt binding of UPF1 to GAS5 thereby protecting it from turnover via nonsense mediated decay. These series of experiments identified our lead compound NPG5-C86 (also referred to herein as Formula 3). The compound and its FITC-labeled derivative were resynthesized, purified by HPLC. The binding affinity of the compound to GAS5 was determined to be about 153 nM by fluorescence polarization.

GAS5 stabilizing compound NPG5-C86 binds to lncRNA GAS5: Since, the compound(s) was designed bind to GAS5 (such that it would disrupt binding to UPF1), its binding to GAS5 was examined. RNA-EMSA as previously described was performed. Briefly, GAS5 was cloned in TOPO vector which has the T7 promoter. In vitro transcription assay was performed with biotin-label using RiboScribe kit using T7 RNA polymerase at 37° C. for 2 h in the presence of nucleotides, RNase inhibitor, and 5× transcription buffer. 0.1 nM of transcribed, biotin-labeled GAS5 was incubated with 10 nM NPG5-C86 in presence of 10U yeast tRNA and 10 units of RNase inhibitor in a final volume of 10 μl of RNA shift buffer for 20 min at room temperature and detected using Biotin Chromogenic Detection kit (ThermoFisher). The results with RNA-EMSA demonstrate that NPG5-C86 bound to GAS5 transcript.

Compound NPG5-C86 can increase GAS5 levels in diabetic adipocytes: Next, it was evaluated whether NPG5-C86 could stabilize GAS5 in diabetic adipocytes. Diabetic adipocytes (DM adipocytes obtained by in vitro differentiation as described above) were treated with NPG5-C86 (20 nM) for 24 hours. GAS5 levels were measured using SYBR Green qPCR. The results show that NPG5-C86 can substantially increases GAS5 levels in DM adipocytes. Further, NPG5-C86 increased GAS5 without causing cellular toxicity.

GAS5 compound NPG5-C86 increases GAS5 levels in diabetic adipose explants: Subcutaneous and omental adipose tissue were obtained from type 2 diabetic patients (IRB20295; n=3; BMI 25.1±3; T2DM patients HbA1c 8±0.7; nonsmokers, no cancers, other criteria matched as described above) and incubated in adipocyte medium (AM medium; ZenBio); treated with or without NPG5-C86 (20 nM) for 48 h. The tissue was homogenized and total RNA was extracted. GAS5 levels were measured using SYBR Green qPCR. The results show NPG5-C86 substantially increases GAS5 levels in diabetic adipose tissue from subcutaneous and omental depots.

REFERENCES FOR EXAMPLE 7

1. Bluher M, Michael M D, Peroni O D, et al. Adipose tissue selective insulin receptor knockout protects against obesity and obesity-related glucose intolerance. Developmental cell. 2002; 3(1):25-38. PubMed PMID: 12110165.
2. Kitamura T, Kahn C R, Accili D. Insulin receptor knockout mice. Annual review of physiology. 2003; 65:313-32. doi: 10.1146/annurev.physiol.65.092101.142540. PubMed PMID: 12471165.
3. Zhu M, Chen Q, Liu X, et al. lncRNA H19/miR-675 axis represses prostate cancer metastasis by targeting TGFBI. The FEBS journal. 2014; 281(16):3766-75. doi: 10.1111/febs.12902. PubMed PMID: 24988946.
4. Zhao Q, Li T, Qi J, et al. The miR-545/374a cluster encoded in the Ftx lncRNA is overexpressed in HBV-related hepatocellular carcinoma and promotes tumorigenesis and tumor progression. PloS one. 2014; 9(10):e109782. doi: 10.1371/journal.pone.0109782. PubMed PMID: 25299640; PubMed Central PMCID: PMC4192320.
5. Schmidt L H, Gorlich D, Spieker T, et al. Prognostic impact of Bcl-2 depends on tumor histology and expression of MALAT-1 lncRNA in non-small-cell lung cancer. Journal of thoracic oncology: official publication of the International Association for the Study of Lung Cancer. 2014; 9(9):1294-304. doi: 10.1097/JTO.0000000000000243. PubMed PMID: 25036876.
6. Qin X, Yao J, Geng P, et al. LncRNA TSLC1-AS1 is a novel tumor suppressor in glioma. International journal of clinical and experimental pathology. 2014; 7(6):3065-72. PubMed PMID: 25031725; PubMed Central PMCID: PMC4097230.
7. Coccia E M, Cicala C, Charlesworth A, et al. Regulation and expression of a growth arrest-specific gene (gas5) during growth, differentiation, and development. Molecular and Cellular Biochemistry. 1992; 12(8):3514-21. Epub 1992/08/01. PubMed PMID: 1630459; PubMed Central PMCID: PMC364604.
8. Smith C M, Steitz J A. Classification of gas5 as a multi-small-nucleolar-RNA (snoRNA) host gene and a member of the 5'-terminal oligopyrimidine gene family reveals common features of snoRNA host genes. Molecular and Cellular Biochemistry. 1998; 18(12):6897-909. Epub 1998/11/20. PubMed PMID: 9819378; PubMed Central PMCID: PMC109273.
9. Raho G, Barone V, Rossi D, et al. The gas 5 gene shows four alternative splicing patterns without coding for a protein. Gene. 2000; 256(1-2):13-7. Epub 2000/10/31. PubMed PMID: 11054530.
10. Smedley D, Sidhar S, Birdsall S, et al. Characterization of chromosome 1 abnormalities in malignant melanomas. Genes, chromosomes & cancer. 2000; 28(1):121-5. Epub 2000/03/30. PubMed PMID: 10738310.
11. Qi L, Qi Q, Prudente S, et al. Association between a genetic variant related to glutamic acid metabolism and coronary heart disease in individuals with type 2 diabetes. JAMA. 2013; 310(8):821-8. doi: 10.1001/jama.2013.276305. PubMed PMID: 23982368; PubMed Central PMCID: PMC3858847.
12. Williams G T, Mourtada-Maarabouni M, Farzaneh F. A critical role for non-coding RNA GAS5 in growth arrest and rapamycin inhibition in human T-lymphocytes. Biochem Soc Trans. 2011; 39(2):482-6. Epub 2011/03/25. doi: 10.1042/BST0390482. PubMed PMID: 21428924.
13. Mourtada-Maarabouni M, Pickard M R, Hedge V L, et al. GAS5, a non-protein-coding RNA, controls apoptosis and is downregulated in breast cancer. Oncogene(s). 2009; 28(2):195-208. Epub 2008/10/07. doi: 10.1038/onc.2008.373. PubMed PMID: 18836484.
14. Kino T, Hurt D E, Ichijo T, et al. Noncoding RNA gas5 is a growth arrest- and starvation-associated repressor of the glucocorticoid receptor. Science signaling. 2010; 3(107):ra8. Epub 2010/02/04. doi: 10.1126/scisignal.2000568. PubMed PMID: 20124551; PubMed Central PMCID: PMC2819218.
15. Kleiman E, Carter G, Ghansah T, et al. Developmentally spliced PKCbetaII provides a possible link between mTORC2 and Akt kinase to regulate 3T3-L1 adipocyte insulin-stimulated glucose transport. Biochem Biophys Res Commun. 2009; 388(3):554-9. Epub 2009/08/19. doi: 10.1016/j.bbrc.2009.08.063. PubMed PMID: 19686698; PubMed Central PMCID: PMC3033743.
16. Elmendorf J S. Fractionation analysis of the subcellular distribution of GLUT-4 in 3T3-L1 adipocytes. Methods in molecular medicine. 2003; 83:105-11. Epub 2003/03/07. doi: 10.1385/1-59259-377-1:105. PubMed PMID: 12619721.
17. Tani H, Torimura M, Akimitsu N. The RNA degradation pathway regulates the function of GAS5 a non-coding RNA in mammalian cells. PloS one. 2013; 8(1):e55684. Epub 2013/02/06. doi: 10.1371/journal.pone.0055684. PubMed PMID: 23383264; PubMed Central PMCID: PMC3559549.
18. Azzalin C M, Lingner J. The human RNA surveillance factor UPF1 is required for S phase progression and genome stability. Curr Biol. 2006; 16(4):433-9. doi: 10.1016/j.cub.2006.01.018. PubMed PMID: 16488880.
19. Azzalin C M. UPF1: a leader at the end of chromosomes. Nucleus. 2012; 3(1):16-21. PubMed PMID: 22156744.
20. Wu H, Li Y, Bai G, et al. gamma-AApeptide-based small-molecule ligands that inhibit Abeta aggregation. Chemical communications. 2014; 50(40):5206-8. doi: 10.1039/c3cc46685j. PubMed PMID: 24158240.

21. Teng P, Zhang X, Wu H, et al. Identification of novel inhibitors that disrupt STAT3-DNA interaction from a gamma-AApeptide OBOC combinatorial library. Chemical communications. 2014; 50(63):8739-42. doi: 10.1039/c4cc03909b. PubMed PMID: 24964402; PubMed Central PMCID: PMC4128407.

22. Tani H, Imamachi N, Salam K A, et al. Identification of hundreds of novel UPF1 target transcripts by direct determination of whole transcriptome stability. RNA biology. 2012; 9(11):1370-9. doi: 10.4161/rna.22360. PubMed PMID: 23064114; PubMed Central PMCID: PMC3597577.

We claim:

1. A method of treating Alzheimer's disease, diabetes, or diabetes and Alzheimer's disease in a subject in need thereof, the method comprising:
   administering a therapeutically effective amount of a compound having a structure of formula 1

Formula 1

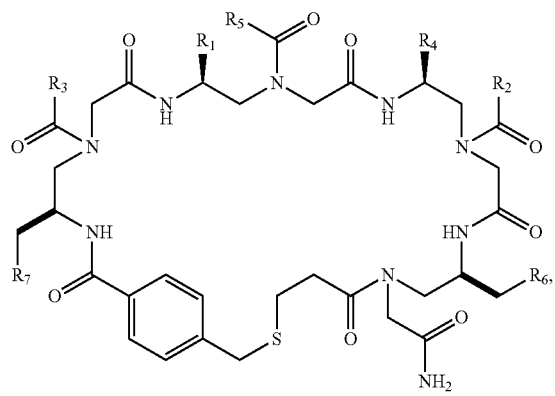

wherein $R_1$ is a methyl, an isobutane, a phenyl, an indole, or a butanamine, wherein $R_2$ is an ethylbenzene, an ethylcyclohexane, an isopentane, a phenyl, a propanamine, or a methylcyclopropane, wherein $R_3$ is a methylcyclopropane, a propionic acid, an ethylbenzene, or a propanamine wherein $R_4$ is a butanamine, a propionic acid, or a phenyl, wherein $R_5$ is a methylcyclopropane, a propionic acid, or an ethylbenzene, wherein $R_6$ is a phenyl, a propionic acid, an isobutene, and wherein $R_7$ is a phenyl, a propionic acid, a butanamine, or a methyl;

or a pharmaceutical formulation thereof, to the subject in need thereof.

2. The method of claim 1, wherein the compound has a structure according to any one of Formulas 3-4, 6-19, Formula 3

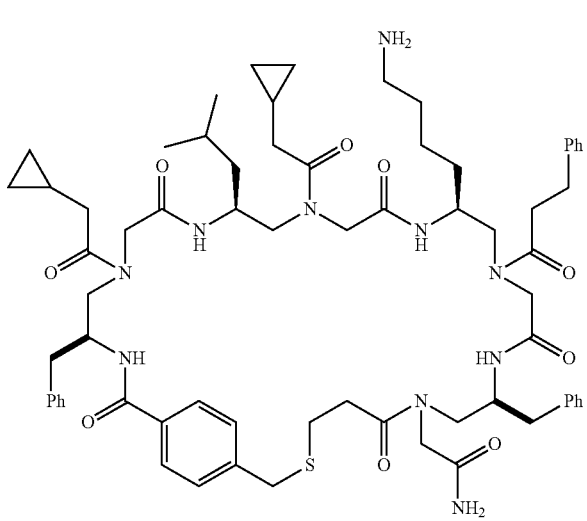

-continued
Formula 4
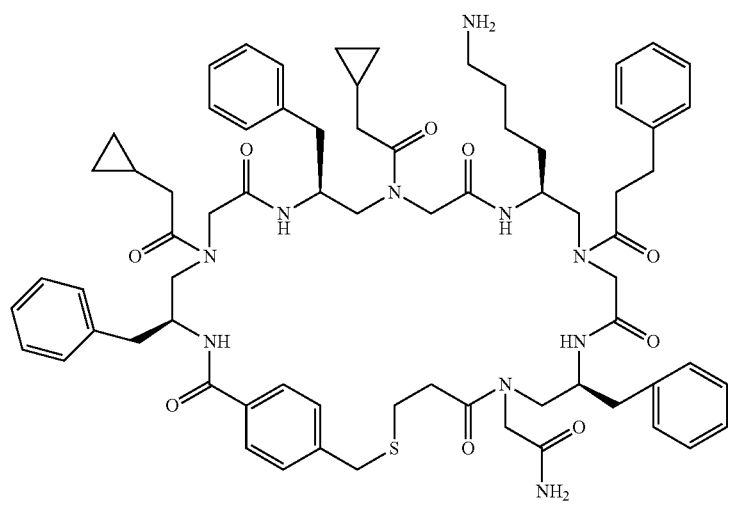
Formula 6
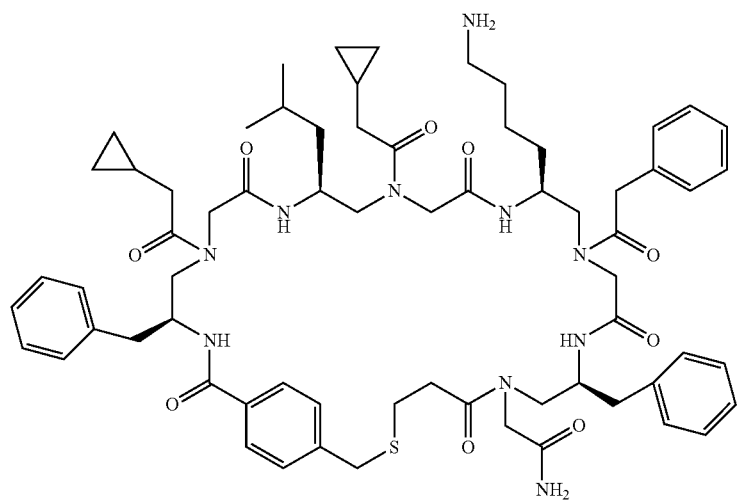
Formula 7
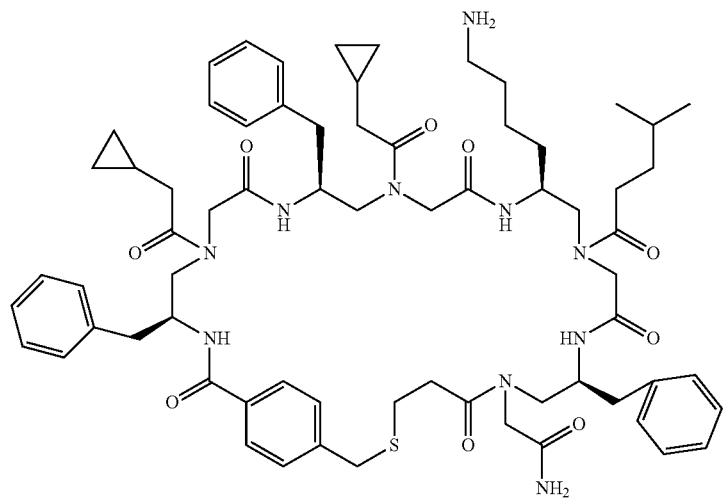

Formula 8
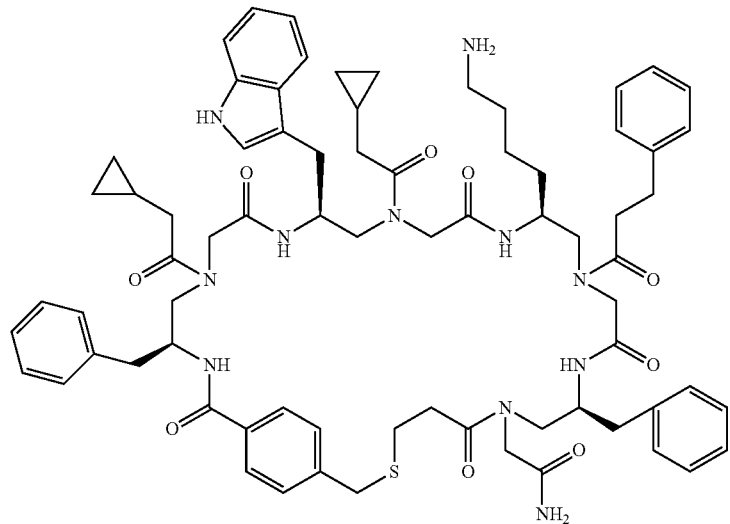
Formula 9
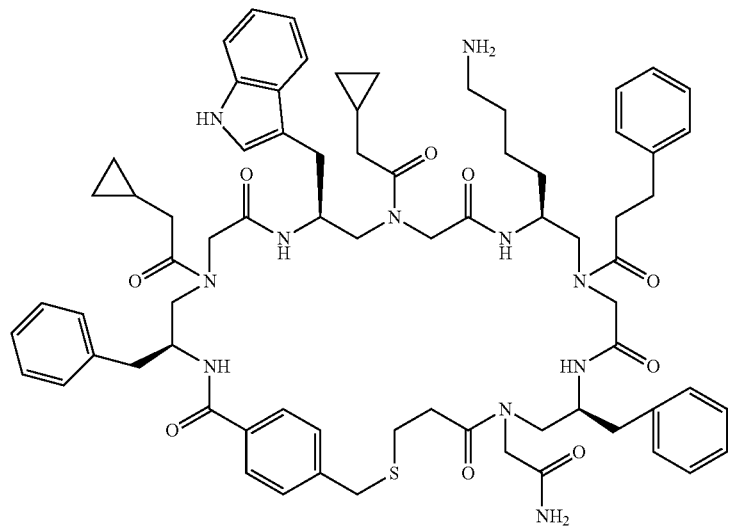
Formula 10
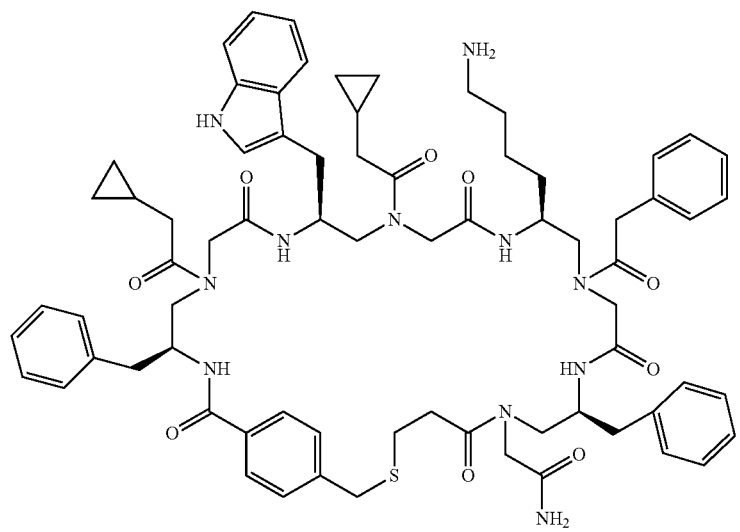

Formula 11
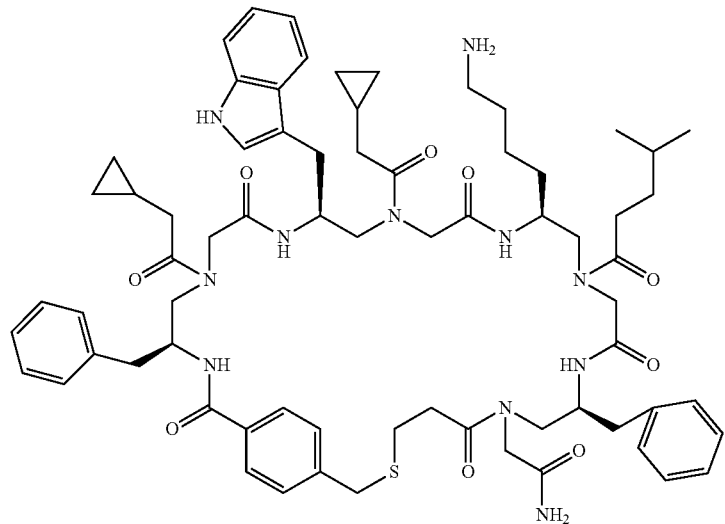
Formula 12
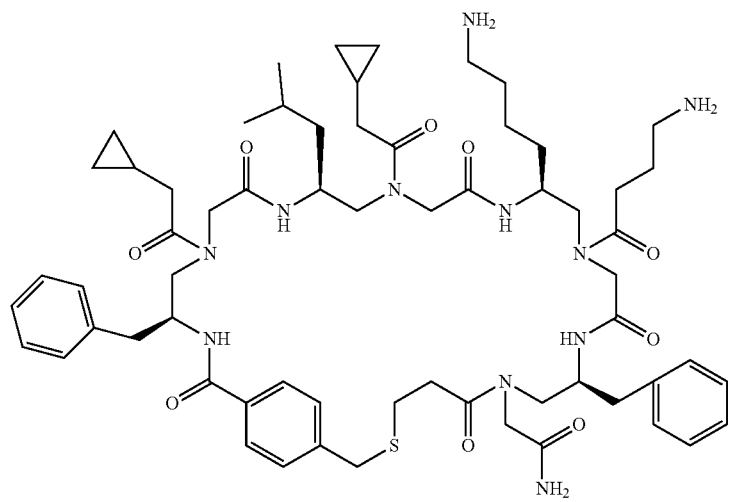
Formula 13
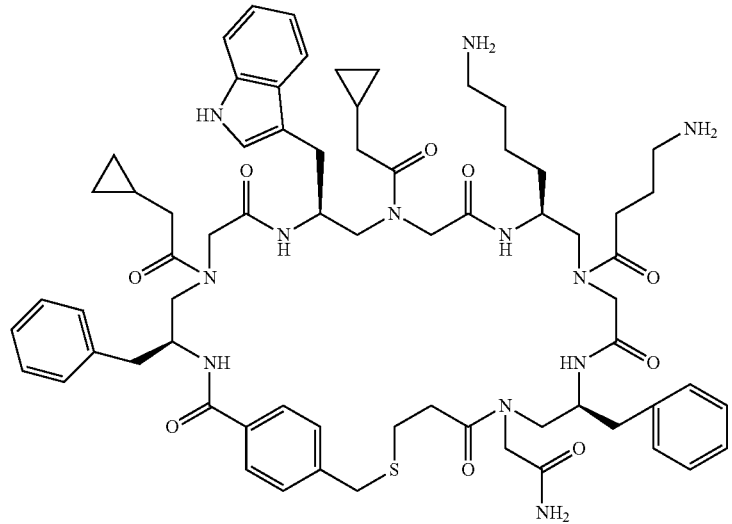

Formula 14
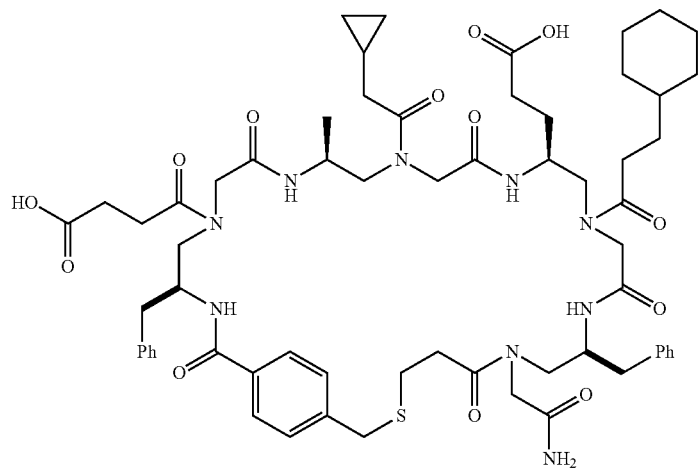
Formula 15
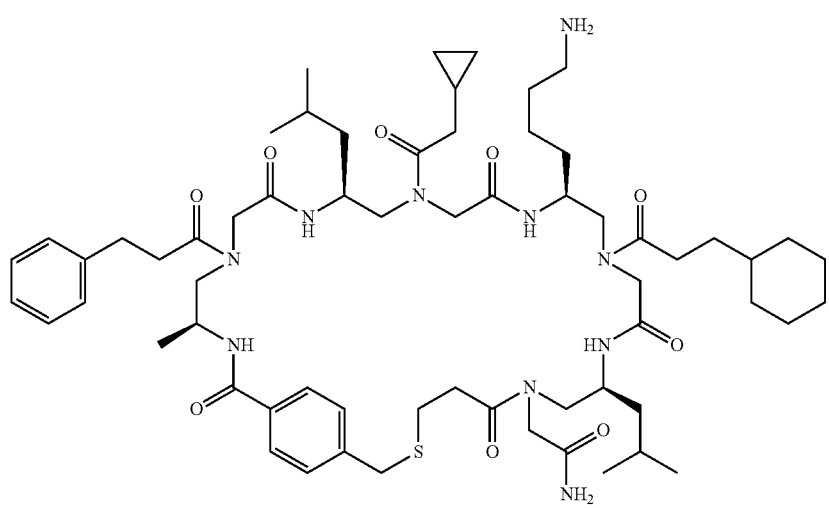
Formula 16
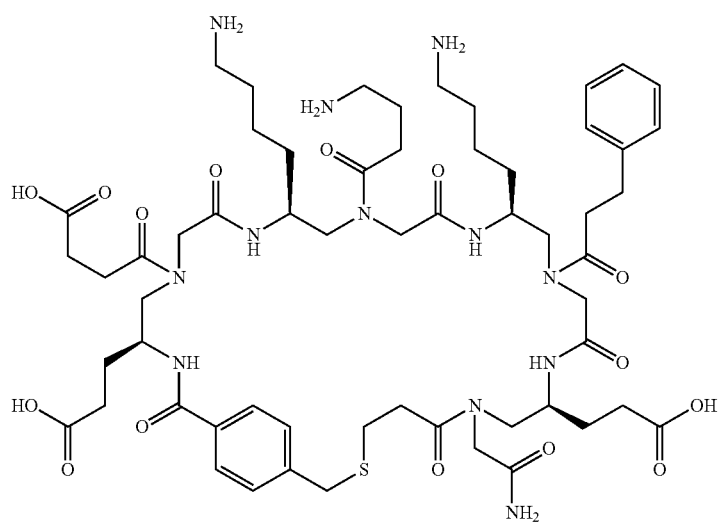

Formula 17
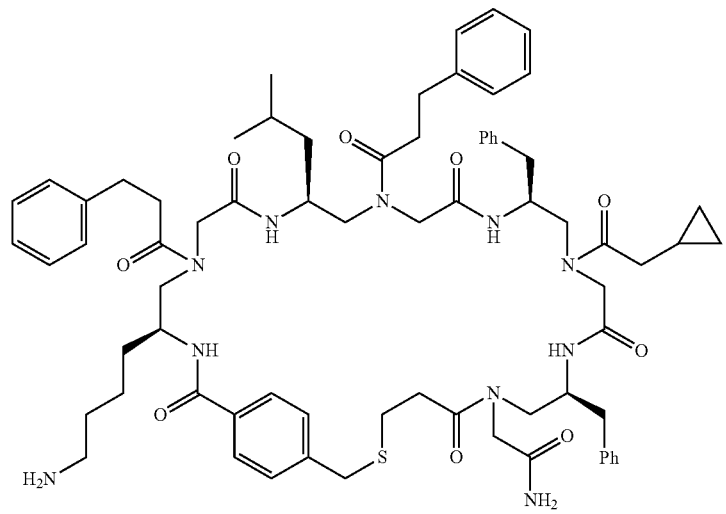
Formula 18
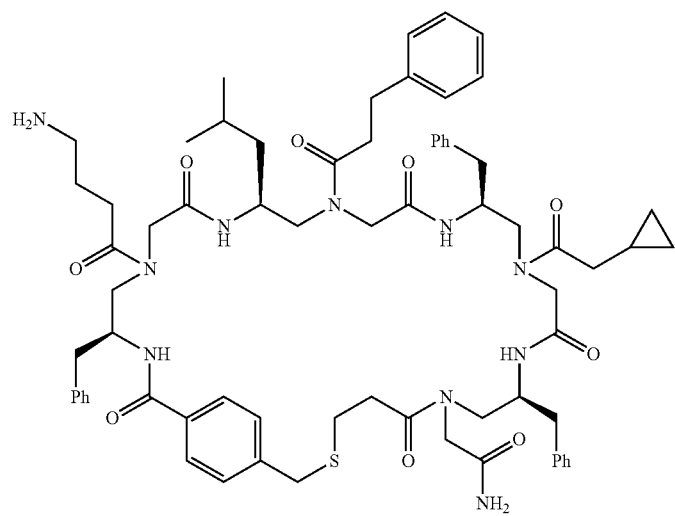

Formula 19

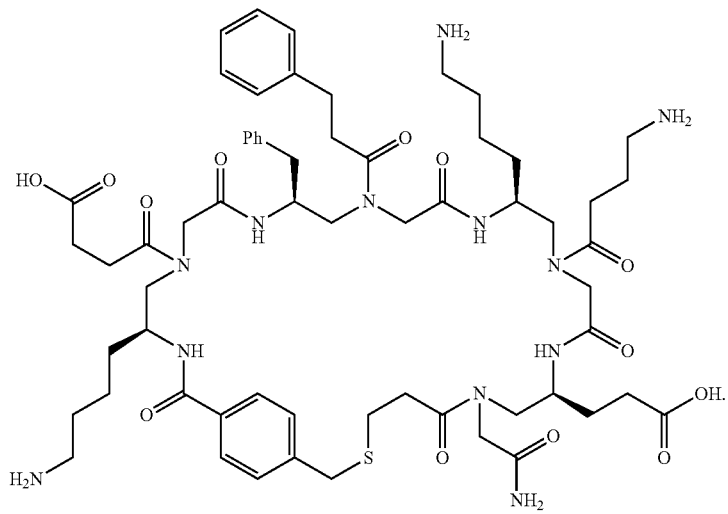

3. The method of claim 2, wherein the compound is capable of binding a GAS5 long non-coding RNA.

4. The method of claim 3, wherein the GAS5 long non-coding RNA has a sequence that is 90%-100% identical to SEQ ID NO: 1.

5. The method of claim 2, wherein administering occurs via oral, rectal, intraocular, inhaled, intranasal, topical, vaginal, parenteral, subcutaneous, intramuscular, intravenous, or intradermal administration.

6. The method of claim 1, wherein the compound is capable of binding a GAS5 long non-coding RNA.

7. The method of claim 6, wherein the GAS5 long non-coding RNA has a sequence that is 90%-100% identical to SEQ ID NO: 1.

8. The method of claim 1, wherein a pharmaceutical formulation is administered to the subject in need thereof and the pharmaceutical formulation further comprises an agent selected from the group consisting of: antisense or RNA interference molecules, chemotherapeutics, antineoplastic agents, hormones, antibiotics, antivirals, immunomodulating agents, antinausea, pain modifying agents, anti-inflammatory agents, antipyretics, antibiotics, antibodies, antibody fragments, and any combination thereof.

9. The method of claim 1, further comprising contacting a sample from the subject in need thereof or component thereof with a capture molecule, wherein the capture molecule is configured to specifically bind to a biomarker, wherein the biomarker is gas5 (SNHG2); and detecting specific binding of the biomarker to the capture molecule.

10. The method of claim 9, wherein the step of detecting specific binding of the biomarker to the capture molecule is performed using a method comprising a technique selected from the group consisting of: array polymerase chain reaction (PCR), quantitative PCR (qPCR), real-time PCR, real-time qPCR, reverse-transcription PCR (RT-PCR), real-time RT-PCR, RT-qPCR, real-time RT-qPCR, digital PCR (dPCR), RNA flare, (LATE)-PCR, RNA flow cytometry, nucleotide sequencing, cell-based RNA detection assays, in situ hybridization, northern blot analysis, and any combination thereof.

11. The method of claim 9, wherein the capture molecule has a sequence that is 95%-100% identical to any one of SEQ ID NOs.: 2-3.

12. The method of claim 1, wherein the subject is greater than 45 years of age.

13. The method of claim 1, wherein the subject is less than 45 years of age.

14. The method of claim 1, wherein the subject has or is suspected of having diabetes.

* * * * *

SEQUENCE LISTING

<160> NUMBER OF SEQ ID NOS: 5

<210> SEQ ID NO 1
<211> LENGTH: 591
<212> TYPE: DNA
<213> ORGANISM: Artificial Sequence
<220> FEATURE:
<223> OTHER INFORMATION: Gas5 lncRNA

<400> SEQUENCE: 1

```
tggatagcac cttatggaca gttgtgtccc caaggaagga tgagaatagc tactgaagtc    60
ctaaagagca agcctaactc aagccattgg cacacaggca ttagacagaa agctggaagt   120
tgaaatggtg gagtccaact tgcctggacc agcttaatgg ttctgctcct ggtaacgttt   180
ttatccatgg atgacttgct tgggtaagga catgaagaca gttcctgtca tacctttaa    240 aggtatggag agtcggcttg actacactgt gtggagcaag ttttaaagaa gcaaaggact   300
cagaattcat gattgaagaa atgcaggcag acctgttatc ctaaactagg gttttaatg    360 accacaacaa gcaagcatgc agcttactgc ttgaaagggt cttgcctcac ccaagctaga   420
gtgcagtggc ctttgaagct tactacagcc tcaaacttct gggctcaagt gatcctcagc   480
ctcccagtgg tctttgtaga ctgcctgatg gagtctcatg gcacaagaag attaaaacag   540
tgtctccaat tttaataaat ttttgcaatc caaaaaaaaa aaaaaaaaa a             591
```

<210> SEQ ID NO 2
<211> LENGTH: 18
<212> TYPE: DNA
<213> ORGANISM: Artificial Sequence
<220> FEATURE:
<223> OTHER INFORMATION: GAS5 sense primer

<400> SEQUENCE: 2

```
agctggaagt tgaaatgg                                                   18
```

<210> SEQ ID NO 3
<211> LENGTH: 18
<212> TYPE: DNA
<213> ORGANISM: Artificial Sequence
<220> FEATURE:
<223> OTHER INFORMATION: GAS 5 anti-sense primer

<400> SEQUENCE: 3

```
agctggaagt tgaaatgg                                                   18
```

<210> SEQ ID NO 4
<211> LENGTH: 111
<212> TYPE: DNA
<213> ORGANISM: Artificial Sequence
<220> FEATURE:
<223> OTHER INFORMATION: This sequence is a portion of the GAS5 lncRNA.
     This is a sequence within SEQ ID NO: 1 and corresponds to
     nucleotides 541 to 651 of SEQ ID NO: 1

<400> SEQUENCE: 4

```
ctcccagtgg tctttgtaga ctgcctgatg gagtctcatg gcacaagaag attaaaacag    60
tgtctccaat tttaataaat ttttgcaatc caaaaaaaaa aaaaaaaaa a              111
```

```
<210> SEQ ID NO 5
<211> LENGTH: 11
<212> TYPE: DNA
<213> ORGANISM: Artificial Sequence
<220> FEATURE:
<223> OTHER INFORMATION: Sequence begining at -826 bp of insuliin
      receptor gene promoter region

<400> SEQUENCE: 5 aacgtttttta t                                                            11
```